(12) United States Patent
Niitsu et al.

(10) Patent No.: US 10,632,653 B2
(45) Date of Patent: Apr. 28, 2020

(54) FINE HOLLOW PROTRUSION MANUFACTURING METHOD

(71) Applicant: KAO CORPORATION, Tokyo (JP)

(72) Inventors: Takatoshi Niitsu, Utsunomiya (JP); Hideo Kobayashi, Mooka (JP); Satoshi Ueno, Utsunomiya (JP); Ryosuke Manabe, Oyama (JP)

(73) Assignee: KAO CORPORATION, Tokyo (JP)

( * ) Notice: Subject to any disclaimer, the term of this patent is extended or adjusted under 35 U.S.C. 154(b) by 497 days.

(21) Appl. No.: 15/519,440

(22) PCT Filed: Oct. 6, 2015

(86) PCT No.: PCT/JP2015/078372
§ 371 (c)(1),
(2) Date: Apr. 14, 2017

(87) PCT Pub. No.: WO2016/060020
PCT Pub. Date: Apr. 21, 2016

(65) Prior Publication Data
US 2017/0239855 A1  Aug. 24, 2017

(30) Foreign Application Priority Data

Oct. 17, 2014 (JP) ................................ 2014-212564
Aug. 17, 2015 (JP) ................................ 2015-160727
(Continued)

(51) Int. Cl.
*B29C 43/02* (2006.01)
*B29C 59/02* (2006.01)
(Continued)

(52) U.S. Cl.
CPC ....... *B29C 43/021* (2013.01); *A61M 37/0015* (2013.01); *B29C 35/0261* (2013.01);
(Continued)

(58) Field of Classification Search
CPC .............. B29C 43/021; B29C 35/0261; A61M 37/0015
See application file for complete search history.

(56) References Cited

U.S. PATENT DOCUMENTS 6,256,533 B1   7/2001 Yuzhakov et al.
6,312,612 B1 * 11/2001 Sherman ........... A61M 37/0015
                                                    216/11
(Continued)

FOREIGN PATENT DOCUMENTS

JP        1-110929 A    4/1989
JP    2003-501161 A    1/2003
(Continued)

OTHER PUBLICATIONS

International Search Report, issued in PCT/JP2015/078372, PCT/ISA/210, dated Dec. 15, 2015.

*Primary Examiner* — Jacob T Minskey
*Assistant Examiner* — Yung-Sheng M Tsui
(74) *Attorney, Agent, or Firm* — Birch, Stewart, Kolasch & Birch, LLP

(57) ABSTRACT

A method for manufacturing a fine hollow protruding article (1) according to the invention involves: a protrusion forming step of bringing a projecting mold part (11) that includes a heating means into contact from one surface (2D) side of a base sheet (2) including a thermoplastic resin, and, while softening, with heat, a contact section (TP) in the base sheet (2) where the projecting mold part (11) contacts the base sheet (2), inserting the projecting mold part (11) into the base sheet (2), to form a protrusion (3) that protrudes from the other surface (2U) side of the base sheet (2); a cooling step of cooling the protrusion (3) in a state where the projecting mold part (11) is inserted in an interior of the protrusion (3); and a release step of withdrawing the pro- (Continued)

jecting mold part (11) from the interior of the protrusion (3) after the cooling step, to form the fine hollow protruding article (1).

22 Claims, 24 Drawing Sheets

(30) Foreign Application Priority Data

| Aug. 17, 2015 | (JP) | 2015-160728 |
|---|---|---|
| Aug. 17, 2015 | (JP) | 2015-160729 |
| Sep. 8, 2015 | (JP) | 2015-176375 |
| Sep. 8, 2015 | (JP) | 2015-176376 |
| Sep. 8, 2015 | (JP) | 2015-176377 |

(51) Int. Cl.
*A61M 37/00* (2006.01)
*B29C 35/02* (2006.01)
B29C 35/16 (2006.01)
B29K 101/12 (2006.01)
B29L 31/00 (2006.01)

(52) U.S. Cl.
CPC ..... *B29C 59/022* (2013.01); *A61M 2037/003* (2013.01); *A61M 2037/0046* (2013.01); *A61M 2037/0053* (2013.01); *B29C 59/025* (2013.01); *B29C 2035/1658* (2013.01); *B29C 2043/025* (2013.01); *B29K 2101/12* (2013.01); *B29K 2905/00* (2013.01); *B29L 2031/753* (2013.01)

(56) References Cited

U.S. PATENT DOCUMENTS

| 6,379,324 | B1 | 4/2002 | Gartstein et al. |
|---|---|---|---|
| 6,451,240 | B1 | 9/2002 | Sherman et al. |
| 6,565,532 | B1 | 5/2003 | Yuzhakov et al. |
| 6,652,478 | B1 | 11/2003 | Gartstein et al. |
| 6,931,277 | B1 | 8/2005 | Yuzhakov et al. |
| 2002/0020688 | A1 | 2/2002 | Sherman et al. |
| 2004/0164454 | A1 | 8/2004 | Gartstein et al. |
| 2005/0178760 | A1 | 8/2005 | Chang et al. |
| 2005/0209565 | A1 | 9/2005 | Yuzhakov et al. |
| 2008/0088066 | A1* | 4/2008 | Ferguson ............... B29C 45/561 264/443 |
| 2010/0004608 | A1 | 1/2010 | Hamamoto et al. |
| 2012/0041337 | A1 | 2/2012 | Ferguson et al. |

FOREIGN PATENT DOCUMENTS

| JP | 2003-501162 A | 1/2003 |
|---|---|---|
| JP | 2006-69076 A | 3/2006 |
| JP | 2006-518675 A | 8/2006 |
| JP | 2010-68840 A | 4/2010 |
| JP | 2011-72695 A | 4/2011 |
| JP | 2012-523270 A | 10/2012 |
| JP | 2013-172833 A | 9/2013 |
| JP | 2014-141002 A | 8/2014 |
| JP | 2017-38781 A | 2/2017 |
| JP | 2017-51325 A | 3/2017 |
| WO | WO 2008/093679 A1 | 8/2008 |
| WO | WO 2010/137319 A1 | 12/2010 |

* cited by examiner

Fig. 28
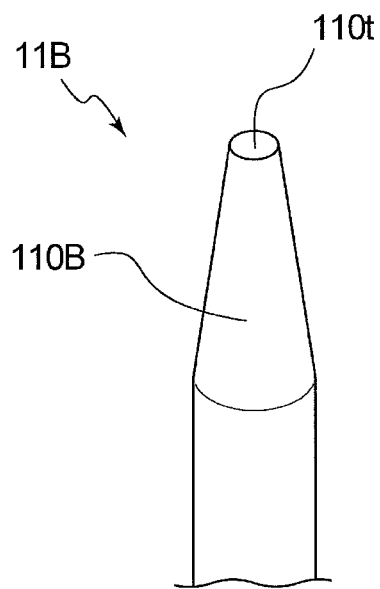
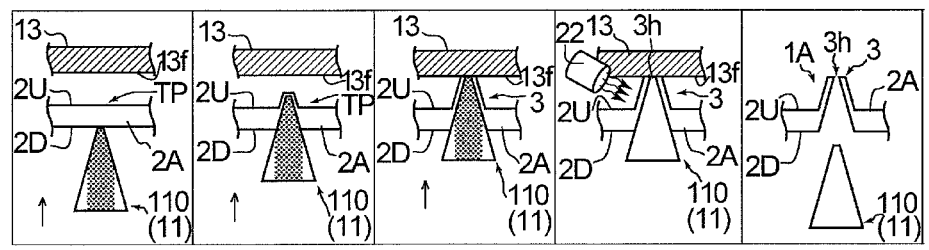
Fig.29(a) Fig.29(b) Fig. 29(c) Fig.29(d) Fig.29(e)

FINE HOLLOW PROTRUSION MANUFACTURING METHOD

TECHNICAL FIELD

The present invention relates to a method for manufacturing a fine hollow protruding article having a hollow interior.

The present invention relates to a method for manufacturing a fine hollow protruding article having a through hole.

BACKGROUND ART

Delivery of agents with microneedles is receiving attention in recent years, because the same performance as delivering agents with syringes can be achieved without harming the skin and with less pain. Among microneedles, hollow microneedles, in particular, can widen the range of choices of agents to be provided in the hollow portion.

Other than hollow microneedles, there are, in general, self-dissolving-type needles in which the needle itself is made of a dissolvable agent, and coating-type needles in which the needle surface is coated with an agent. In both types, however, the amount of delivery of an agent (the amount of agent held) depends on the shape of the needle. In contrast, hollow-type needles are advantageous in that a large amount of agent can be delivered, irrespective of needle shape.

Such microneedles can be manufactured according to manufacturing methods disclosed in Patent Literature 1 or 2, for example. In the manufacturing method disclosed in Patent Literature 1, a resin body is arranged on an elastic body, and while heating the resin body from the back-surface side of the elastic body, a fine needle is caused to penetrate the resin body to manufacture a fine nozzle. Thus, there is no need to use a mold that includes a fine depression having an inverted shape of the outer shape of the nozzle, and a disposable fine nozzle can be manufactured from a resin.

Patent Literature 2 describes that a hollow microneedle array can be manufactured using a pre-formed mold.

Patent Literature 3 discloses a method for manufacturing microneedles by: arranging a base sheet so as to bridge rod-shaped protrusions; heating the entire base sheet; and causing the sheet to deform into the shape of the rod-shaped protrusions.

Further, delivery of agents with microneedles is receiving attention in recent years in the field of medical care or cosmetics. Microneedles can achieve the same performance as delivering agents with syringes without causing any pain by piercing only the outer layers of the skin. Among microneedles, microneedles having a through hole are particularly advantageous in that they can widen the range of choices of agents to be provided inside the microneedle. However, the use of a microneedle having a through hole, particularly in the field of medical care or cosmetics, calls for precision in microneedle height and precision of the through hole.

Microneedles having through holes can be manufactured according to the manufacturing methods disclosed in Patent Literatures 1 to 3, for example. Patent Literature 1 describes a method for manufacturing a fine nozzle by: arranging a resin body on an elastic body; and, while heating the resin body from the back-surface side of the elastic body, causing a fine needle to penetrate the resin body and causing the resin body to flow between the elastic body and the fine needle.

Patent Literature 2 describes a method wherein a hollow microneedle array is manufactured by molding by using a mold having a plurality of pre-formed depressions and a mold having a plurality of pre-formed projections, and inserting the projections into the respective depressions.

Patent Literature 4 describes a method for manufacturing a fine microneedle having a fine through hole by reproducing a fine microneedle on a substrate by thermal imprinting, and then forming a through hole by a short-pulse laser method.

CITATION LIST

Patent Literature

Patent Literature 1: JP 2013-172833A
Patent Literature 2: US 2012041337 (A1)
Patent Literature 3: U.S. Pat. No. 6,312,612 (B1)
Patent Literature 4: JP 2011-72695A

SUMMARY OF INVENTION

In the fine nozzle manufacturing method described in Patent Literature 1, the entire resin body arranged on the elastic body is heated from the back-surface side of the elastic body by employing, for example, an electrically heated plate; thus, it takes time to heat the entire resin body, making it difficult to improve productivity. Further, because it is necessary to heat the entire resin body arranged on the elastic body, it is difficult to manufacture fine nozzles consecutively.

In the method for manufacturing a fine-through-hole molded product as described in Patent Literature 2, the molds used for molding are expensive, leading to increased costs. Further, there is a low degree of flexibility in microneedle shape and in materials that can be chosen.

In the method described in Patent Literature 3, the entire base sheet is heated; thus, it takes time to heat the entire resin body, making it difficult to improve productivity. Further, at the time of forming the fine needles in an array, it is considered that sections other than where the fine needles are formed are also likely to undergo thermal deformation, making it difficult to control the distance from the bottom of the sheet to the needle's tip end.

The present invention provides a fine hollow protruding article manufacturing method capable of overcoming the drawbacks of the aforementioned conventional art.

Further, in the manufacturing method described in Patent Literature 1, the entire resin body arranged on the elastic body is heated from the back-surface side of the elastic body by employing, for example, an electrically heated plate; thus, it takes time to heat the entire resin body, making it difficult to mass-produce fine nozzles at low cost. Further, Patent Literature 1 describes nothing in terms of adjusting the height of the microneedle and adjusting the size of the through hole formed in the microneedle.

In the manufacturing method described in Patent Literature 2, the molds used for molding are expensive, leading to increased costs. Further, there is a low degree of flexibility in the shape of the microneedle being manufactured and in materials that can be chosen as materials for the microneedle, making it difficult to mass-produce a hollow microneedle array at low cost. Further, Patent Literature 2 describes nothing in terms of adjusting the height of the microneedle and adjusting the size of the through hole formed in the microneedle.

In the manufacturing method described in Patent Literature 4, the through hole in the microneedle is formed by employing a short-pulse laser method as post-processing. This increases facility burden, and it is difficult to mass-produce fine microneedles having through holes at low cost. Further, in the manufacturing method described in Patent Literature 4, the through hole in the microneedle is formed by employing a short-pulse laser method; thus, previously formed microneedles may get damaged, making it difficult to produce fine microneedles having through holes with high quality. Further, Patent Literature 4 describes nothing in terms of adjusting the height of the microneedle and adjusting the size of the through hole formed in the microneedle.

The present invention provides a method for manufacturing a fine hollow protruding article having a through hole with which it is possible to overcome the drawbacks of the aforementioned conventional art.

The invention (first invention) relates to a method for manufacturing a fine hollow protruding article having a hollow interior. The manufacturing method of the invention (first invention) involves: a protrusion forming step of bringing a projecting mold part that includes a heating means into contact from one-surface side of a base sheet including a thermoplastic resin, and, while softening, with heat, a contact section in the base sheet where the projecting mold part contacts the base sheet, inserting the projecting mold part into the base sheet, to form a protrusion that protrudes from another-surface side of the base sheet; a cooling step of cooling the protrusion in a state where the projecting mold part is inserted in an interior of the protrusion; and a release step of withdrawing the projecting mold part from the interior of the protrusion after the cooling step, to form the fine hollow protruding article.

The invention (second invention) relates to a method for manufacturing a fine hollow protruding article having a through hole. The manufacturing method of the invention (second invention) involves: a protrusion forming step for forming a protrusion, the protrusion forming step involving a protrusion precursor forming step of bringing a projecting mold part that includes a heating means into contact from one-surface side of a base sheet including a thermoplastic resin, and, while softening, with heat, a contact section in the base sheet where the projecting mold part contacts the base sheet, inserting the projecting mold part into the base sheet, to form a hollow protrusion precursor that protrudes from another-surface side of the base sheet and that has a through hole that penetrates the tip end on the other-surface side of the base sheet, and a protrusion elongating step of further inserting the projecting mold part into the base sheet in a state where the projecting mold part is inserted in the interior of the protrusion precursor while softening, with heat, the contact section in the base sheet, to form a protrusion that further protrudes from the other surface of the base sheet; a cooling step of cooling the protrusion in a state where the projecting mold part is inserted in the interior of the protrusion; and a release step of withdrawing the projecting mold part from the interior of the protrusion after the cooling step, to form the fine hollow protruding article having a through hole.

The invention (third invention) relates to a method for manufacturing a fine hollow protruding article. The manufacturing method of the invention (third invention) involves: a protrusion forming step of bringing a projecting mold part that includes a heating means into contact from one-surface side of a base sheet including a thermoplastic resin, and, while softening, with heat, a contact section in the base sheet where the projecting mold part contacts the base sheet, inserting the projecting mold part into the base sheet toward another-surface side of the base sheet, to form a protrusion that protrudes from the other-surface side of the base sheet; a cooling step of cooling the protrusion in a state where the projecting mold part is inserted in the interior of the protrusion; and a release step of withdrawing the projecting mold part from the interior of the protrusion after the cooling step, to form the fine hollow protruding article. The protrusion forming step employs a receiving member arranged at a distance from the other surface of the base sheet; and in the protrusion forming step, a through hole is formed in the protrusion by the projecting mold part coming into contact with the receiving member.

BRIEF DESCRIPTION OF DRAWINGS

FIG. 28 is a perspective view of a single projecting mold of a projecting mold part provided to the manufacturing device illustrated in FIG. 27.

FIGS. 29(a) to 29(e) are diagrams illustrating steps for manufacturing a fine hollow protruding article having a through hole by employing the manufacturing device illustrated in FIG. 27.

DESCRIPTION OF EMBODIMENTS

The invention (first invention) is described below according to a preferred first embodiment thereof with reference to the drawings.

Figure 1:
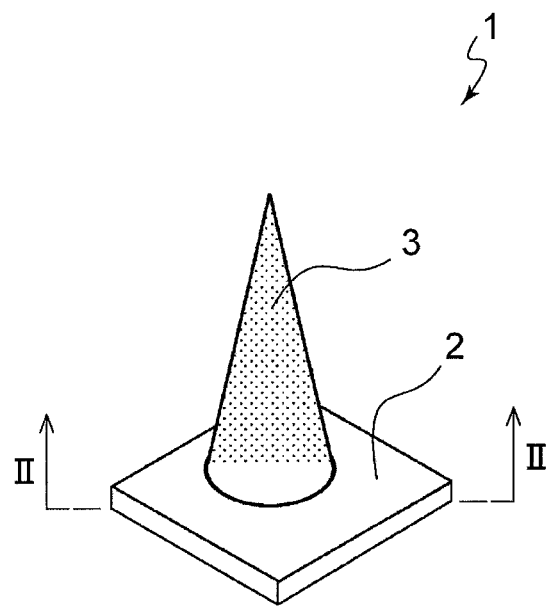
FIG. 1 is a schematic perspective view of an example of a fine hollow protruding article manufactured by a method for manufacturing a fine hollow protruding article of the invention (first invention).
Figure 2:
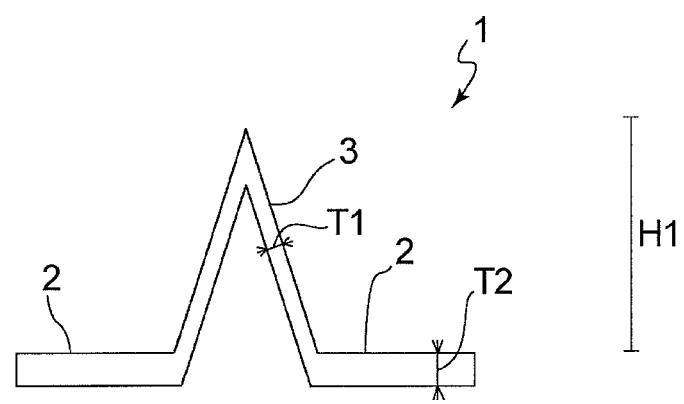
FIG. 2 is a cross-sectional view taken along line II-II illustrated in FIG. 1.

A manufacturing method of the invention (first invention) is a method for manufacturing a fine hollow protruding article having a hollow interior. FIG. 1 illustrates a fine hollow protruding article 1 of an embodiment manufactured according to a method for manufacturing a fine hollow protruding article of a first embodiment. The fine hollow protruding article 1 includes: a sheet-like basal portion 2; and a single circular-conic protrusion 3 provided so as to stand up on the upper surface of the basal portion 2. As illustrated in FIG. 2, the fine hollow protruding article 1 is formed so as to have a hollow interior. More specifically, a hollow space is formed so as to extend up to the interior of the protrusion 3, penetrating the basal portion 2. In the fine hollow protruding article 1, the interior space of the protrusion 3 is formed in a circular-conic shape corresponding to the outer shape of the protrusion 3. It should be noted that, although the protrusion 3 in this fine hollow protruding article 1 is circular-conic, the protrusion may have a shape other than a circular-conic shape, such as the shape of a truncated circular cone, a circular cylinder, a prism, a pyramid, or a truncated pyramid.

In cases where the fine hollow protruding article 1 is to be used as a microneedle, in order for the tip end thereof to reach, for example, the stratum corneum, which is the outermost layer, or the dermis, which is a deeper layer, the protrusion height H1 of the fine hollow protruding article 1 is preferably 0.01 mm or greater, more preferably 0.02 mm or greater, and preferably 10 mm or less, more preferably 5 mm or less, and more specifically, preferably from 0.01 to 10 mm, more preferably from 0.02 to 5 mm. The average thickness T1 of the protrusion 3 is preferably 0.005 mm or greater, more preferably 0.01 mm or greater, and preferably 1.0 mm or less, more preferably 0.5 mm or less, and more specifically, preferably from 0.005 to 1.0 mm, more preferably from 0.01 to 0.5 mm. The thickness T2 of the basal portion 2 is preferably 0.01 mm or greater, more preferably 0.02 mm or greater, and preferably 1.0 mm or less, more preferably 0.7 mm or less, and more specifically, preferably from 0.01 to 1.0 mm, more preferably from 0.02 to 0.7 mm.

The tip end size, in diameter, of the fine hollow protruding article 1 is preferably 0.001 mm or greater, more preferably 0.005 mm or greater, and preferably 0.5 mm or less, more preferably 0.3 mm or less, and more specifically, preferably from 0.001 to 0.5 mm, more preferably from 0.005 to 0.3 mm. The tip end diameter of the fine hollow protruding article 1 is measured as follows.

{Measurement of Tip End Diameter of Fine Hollow Protruding Article 1}

Figure 3:
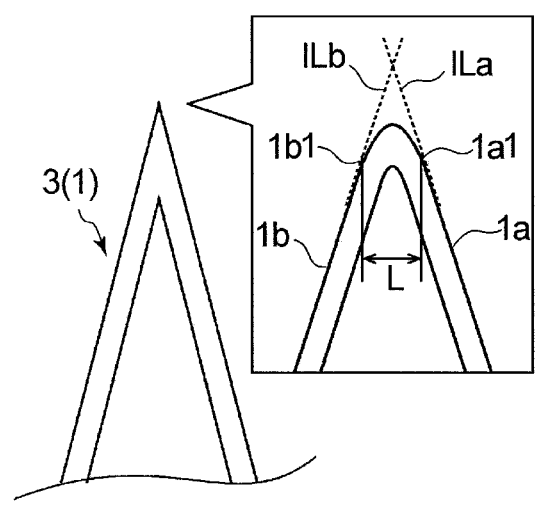
FIG. 3 is an explanatory diagram illustrating a method for measuring the tip end diameter of a hollow protrusion.

The tip end portion of the hollow protruding article 1 is observed in an enlarged state under a predetermined magnification using a scanning electron microscope (SEM) or a microscope, as in the SEM image illustrated in FIG. 3, for example. Next, as illustrated in FIG. 3, an imaginary straight line ILa is extended along the straight-line portion of one lateral side 1a of the two lateral sides 1a, 1b. Also, an imaginary straight line ILb is extended along the straight-line portion of the other lateral side 1b. The point where the lateral side 1a separates from the imaginary straight line ILa on the tip end side is defined as a first tip end point 1a1, and the point where the other lateral side 1b separates from the imaginary straight line ILb is defined as a second tip end point 1b1. The length L of a straight line that connects the first tip end point 1a1 and the second tip end point 1b1 defined as above is measured using a scanning electron microscope (SEM) or a microscope, and the measured length of the straight line is defined as the tip end diameter of the fine hollow protruding article 1.

Figure 4:
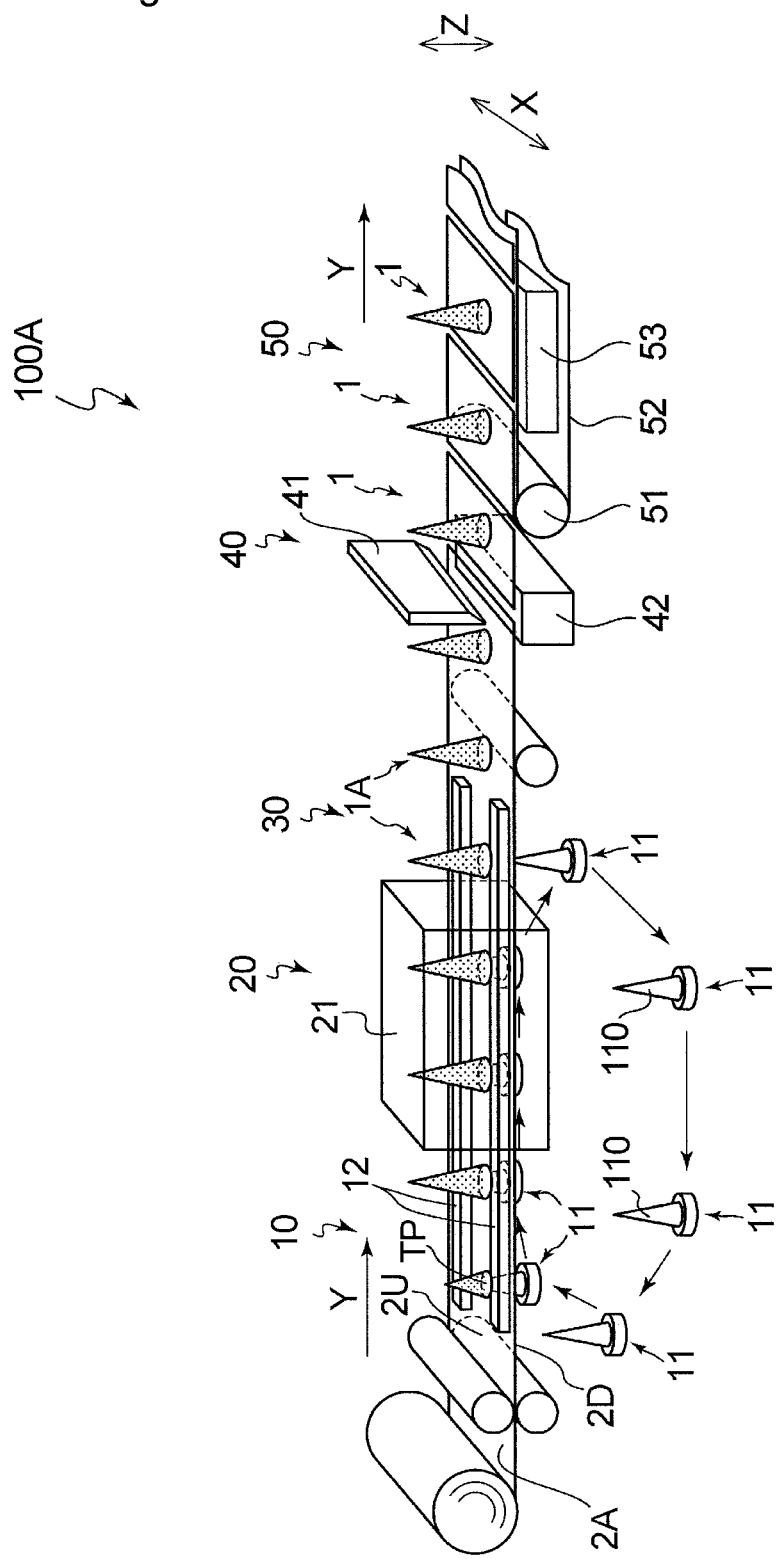
FIG. 4 is a diagram illustrating an overall configuration of a first embodiment of a manufacturing device for manufacturing the fine hollow protruding article illustrated in FIG. 1.

Next, a method for manufacturing a fine hollow protruding article of the invention (first invention) is described with reference to FIGS. 4 to 6, taking a method for manufacturing the aforementioned fine hollow protruding article 1 as an example. FIG. 4 illustrates an overall configuration of a manufacturing device 100A according to the first embodiment used for implementing the manufacturing method of the first embodiment. It should be noted that, the fine hollow protruding article 1 is actually very small as described above, but for the sake of explanation, the fine hollow protruding article 1 is illustrated very large in FIG. 4.

The manufacturing device 100A of the first embodiment illustrated in FIG. 4 includes, from the upstream side toward the downstream side: a protrusion forming section 10 for forming a protrusion 3 in a base sheet 2A; a cooling section 20; a release section 30 where the later-described projecting mold part 11 is withdrawn; a cutting section 40 where each fine hollow protruding article 1 is cut; and a re-pitching section 50 where the interval between the fine hollow protruding articles 1 is adjusted. In the following description, the direction in which the base sheet 2A is transported (the longitudinal direction of the base sheet 2A) is referred to as the Y direction, the direction orthogonal to the transporting direction, which is the width direction of the base sheet 2A being transported, is referred to as the X direction, and the thickness direction of the base sheet 2A being transported is referred to as the Z direction. In the present Specification, the projecting mold part 11 is a member including a projecting mold 110 which is a section that is inserted into the base sheet, and in the present embodiment, the projecting mold part 11 is structured such that the projecting mold 110 is provided on a disk-shaped foundation. The projecting mold part's structure, however, is not limited thereto, and the projecting mold part may consist only of the projecting mold 110, or the projecting mold part 11 may include a plurality of projecting molds 110 arranged on a platform-like support, as in embodiments described further below.

As illustrated in FIG. 4, the protrusion forming section 10 includes projecting mold parts 11 each including a heating means (not illustrated). In the manufacturing device 100A of the first embodiment, no other heating means is provided except for the heating means (not illustrated) of each projecting mold part 11. It should be noted that, in this Specification, "no other heating means is provided except for the heating means of the projecting mold part 11" not only refers to cases where other heating means are completely eliminated, but also refers to cases where a means for heating to a temperature below the softening temperature of the base sheet 2A, or to a temperature below the glass transition temperature, is provided. Note, however, that it is preferable to completely eliminate all other heating means. In the manufacturing device 100A of the first embodiment, the heating means (not illustrated) of the projecting mold part 11 is a heating heater device. In the first embodiment, first, a continuous base sheet 2A is paid out from a material roll of a base sheet 2A including a thermoplastic resin, and is transported in the Y direction. Then, the projecting mold part 11 is brought into contact from one surface 2D side of the continuous base sheet 2A, which is being transported in the Y direction, and, while softening, with heat, a contact section TP in the base sheet 2A where the projecting mold part contacts the base sheet, the projecting mold part 11 is inserted into the base sheet 2A, to form a protrusion 3 that protrudes from the other surface 2U side of the base sheet 2A (protrusion forming step). More specifically, the projecting mold part 11 has a circular-conic section with a sharp tip end, to correspond to the outer shape of the circular-conic protrusion 3 of the fine hollow protruding article 1 being manufactured. In the manufacturing device 100A of the first embodiment, the projecting mold part 11 is arranged so that the tip end thereof faces upward, and is movable at least vertically in the thickness direction (Z direction). More specifically, in the manufacturing device 100A of the first embodiment, the projecting mold part 11 can move vertically in the thickness direction (Z direction) by an electric actuator (not illustrated), and can travel together with the base sheet 2A in the transporting direction (Y direction). The operation of the projecting mold part 11 is controlled by a control means (not illustrated) provided to the manufacturing device 100A of the first embodiment. As described above, the manufacturing device 100A of the first embodiment is a device including a protrusion forming section 10 of the so-called "box-motion-type" which follows an endless track. Heating of the heating means (not illustrated) of the projecting mold part 11 is also controlled by the control means (not illustrated) provided to the manufacturing device 100A of the first embodiment.

The base sheet 2A is a sheet that constitutes the basal portion 2 of the fine hollow protruding article 1 being manufactured, and includes a thermoplastic resin. Examples of the thermoplastic resin include poly-fatty acid esters, polycarbonate, polypropylene, polyethylene, polyester, polyamide, polyamide imide, polyether ether ketone, polyetherimide, polystyrene, polyethylene terephthalate, polyvinyl chloride, nylon resin, acrylic resin, and combinations thereof. From the viewpoint of biodegradability, poly-fatty acid esters are preferably used. Concrete examples of poly-fatty acid esters include polylactic acid, polyglycolic acid, and combinations thereof. Note that the base sheet 2A may be formed of a mixture including, for example, hyaluronic acid, collagen, starch, cellulose, etc., in addition to thermoplastic resin. The thickness of the base sheet 2A is substantially the same as the thickness T2 of the basal portion 2 of the fine hollow protruding article 1 being manufactured.

The shape of the projecting mold part 11 on the tip-end side only needs to be shaped so as to correspond to the outer shape of the protrusion 3 of the fine hollow protruding article 1 being manufactured. The height H2 of the projecting mold 110 of the projecting mold part 11 is equal to or slightly higher than the height H1 of the fine hollow protruding article 1 being manufactured, and is preferably 0.01 mm or greater, more preferably 0.02 mm or greater, and preferably 30 mm or less, more preferably 20 mm or less, and more specifically, preferably from 0.01 to 30 mm, more preferably from 0.02 to 20 mm. The tip end diameter D1 (cf. FIG. 5) of the projecting mold 110 of the projecting mold part 11 is preferably 0.001 mm or greater, more preferably 0.005 mm or greater, and preferably 1 mm or less, more preferably 0.5 mm or less, and more specifically, preferably from 0.001 to 1 mm, more preferably from 0.005 to 0.5 mm. The tip end diameter D1 of the projecting mold 110 of the projecting mold part 11 is measured as follows.

The base diameter D2 of the projecting mold 110 of the projecting mold part 11 is preferably 0.1 mm or greater, more preferably 0.2 mm or greater, and preferably 5 mm or less, more preferably 3 mm or less, and more specifically, preferably from 0.1 to 5 mm, more preferably from 0.2 to 3 mm. From the viewpoint of easily achieving sufficient strength, the tip end angle α of the projecting mold 110 of the projecting mold part 11 is preferably 1 degree or greater, more preferably 5 degrees or greater. From the viewpoint of obtaining a protrusion 3 having an appropriate angle, the tip end angle α is preferably 60 degrees or less, more preferably 45 degrees or less, and more specifically, preferably from 1 to 60 degrees, more preferably from 5 to 45 degrees. The tip end angle α of the projecting mold part 11 is measured as follows.

{Measurement of Tip End Diameter of Projecting Mold 110 of Projecting Mold Part 11}

The tip end portion of the projecting mold 110 of the projecting mold part 11 is observed in an enlarged state under a predetermined magnification using a scanning electron microscope (SEM) or a microscope. Next, as illustrated in FIG. 5, an imaginary straight line ILc is extended along the straight-line portion of one lateral side 11a of the two lateral sides 11a, 11b. Also, an imaginary straight line ILd is extended along the straight-line portion of the other lateral side 11b. The point where the lateral side 11a separates from the imaginary straight line ILc on the tip end side is defined as a first tip end point 11a1, and the point where the other lateral side 11b separates from the imaginary straight line ILd is defined as a second tip end point 11b1. The length D1 of a straight line that connects the first tip end point 11a1 and the second tip end point 11b1 defined as above is measured using a scanning electron microscope (SEM) or a microscope, and the measured length of the straight line is defined as the tip end diameter of the projecting mold 110.

{Measurement of Tip End Angle α of Projecting Mold 110 of Projecting Mold Part 11}

Figure 5:
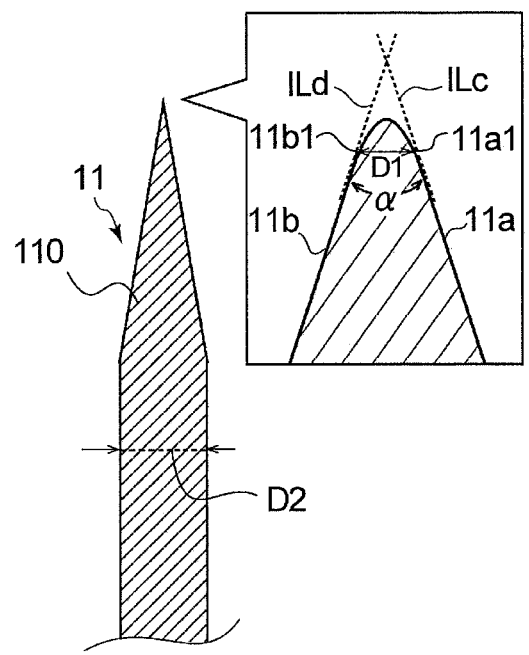
FIG. 5 is an explanatory diagram illustrating a method for measuring the tip end angle of a projecting mold part.

The tip end portion of the projecting mold 110 of the projecting mold part 11 is observed in an enlarged state under a predetermined magnification using a scanning electron microscope (SEM) or a microscope, as in the SEM image illustrated in FIG. 5, for example. Next, as illustrated in FIG. 5, an imaginary straight line ILc is extended along the straight-line portion of one lateral side 11a of the two lateral sides 11a, 11b. Also, an imaginary straight line ILd is extended along the straight-line portion of the other lateral side 11b. The angle formed between the imaginary straight line ILc and the imaginary straight line ILd is measured using a scanning electron microscope (SEM) or a microscope, and the measured angle is defined as the tip end angle α of the projecting mold 110 of the projecting mold part 11.

The projecting mold part 11 is formed of a high-strength material that is hard to bend/break. Examples of materials for the projecting mold part 11 include metals, such as steel, stainless steel, aluminum, aluminum alloy, nickel, nickel alloy, cobalt, cobalt alloy, copper, copper alloy, beryllium copper, and beryllium copper alloy, and ceramics.

In the manufacturing device 100A of the first embodiment, as illustrated in FIG. 4, the protrusion forming section 10 includes a support 12 that supports the base sheet 2A when the projecting mold part 11 is inserted into the base sheet 2A. The support 12 is arranged on the other surface 2U side of the base sheet 2A, and serves to make the base sheet 2A less likely to warp/bend when the projecting mold part 11 is inserted from the one surface 2D side. Thus, the support 12 is arranged in a region, of the base sheet 2A, other than a region where the projecting mold part 11 is inserted into the base sheet 2A. In the manufacturing device 100A of the first embodiment, the support 12 is constituted by a pair of plate-like members extending parallel to the transporting direction (Y direction) on the base sheet 2A's respective lateral sides along the transporting direction (Y direction). The supports 12 extend from the protrusion forming section 10, through the cooling section 20, and up to a position where the release section 30 terminates.

The material constituting the support 12 may be the same as the material of the projecting mold part 11, and may be formed of a synthetic resin, for example.

As illustrated in FIG. 4, in the protrusion forming step of the first embodiment, the pair of supports 12, 12—which is arranged on the other surface 2U side (upper surface side) of the continuous base sheet 2A paid out from the material roll and being transported in the Y direction—supports the base sheet 2A's respective lateral sides along the transporting direction (Y direction). Then, by using the box-motion-type protrusion forming section 10, the projecting mold part 11 is brought into contact from the one surface 2D side (lower surface side) in a section, of the base sheet 2A, that is not supported by the supports 12—i.e., in a central section of the base sheet 2A between the pair of supports 12, 12. That is, in the protrusion forming step, the other surface 2U side (upper surface side) corresponding to the contact section TP of the base sheet 2A in contact with the projecting mold part 11 is in a free floating state, without being provided with a depression, etc., into which the projecting mold part 11 is fitted to form a protruding article.

Figures 6A, 6B, 6C, 6D:
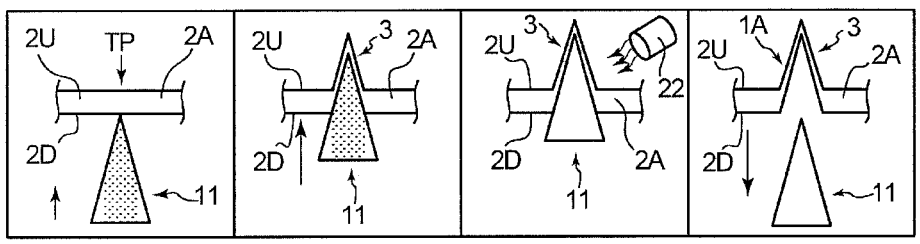
FIGS. 6(a) to 6(d) are diagrams illustrating steps for manufacturing a fine hollow protruding article by employing the manufacturing device illustrated in FIG. 4.

Then, as illustrated in FIG. 6(a), in the first embodiment, the projecting mold part 11 is heated by the heating heater device at the contact section TP, and the contact section TP is softened by generating heat in the contact section TP. Then, as illustrated in FIG. 6(b), while softening the contact section TP, the projecting mold part 11 is raised from the one surface 2D side (lower surface side) of the base sheet 2A toward the other surface 2U side (upper surface side) and is inserted into the base sheet 2A, to form a protrusion 3 that protrudes from the other surface 2U side (upper surface side) of the base sheet 2A.

From the viewpoint of forming the protrusion 3, the heating temperature of the base sheet 2A by the projecting mold part 11 is preferably equal to or higher than the glass transition temperature of the base sheet 2A being used to below the melting temperature thereof, and more preferably, equal to or higher than the softening temperature of the base sheet 2A to below the melting temperature thereof. More specifically, the heating temperature is preferably 30° C. or higher, more preferably 40° C. or higher, and preferably 300° C. or lower, more preferably 250° C. or lower, and more specifically, preferably from 30 to 300° C., more preferably from 40 to 250° C. When a heating heater device is used as in the first embodiment, the heating temperature of the projecting mold part 11 simply needs to be adjusted within the aforementioned range. In cases where the base sheet 2A is heated by using an ultrasonic vibration device in the first embodiment, the heating temperature is employed as the temperature range of a section of the base sheet 2A that comes into contact with the projecting mold 110. It should be noted that the glass transition temperature (Tg) is measured according to the following measurement method, and the softening temperature is measured according to JIS K-7196 "Testing method for softening temperature of thermoplastic film and sheeting by thermomechanical analysis".

Note that the "glass transition temperature (Tg) of the base sheet" refers to the glass transition temperature (Tg) of the resin constituting the base sheet. In cases where there are a plurality of types of constituent resins and the plurality of glass transition temperatures (Tg) are different from each other, the heating temperature of the base sheet by the heating means is preferably at least equal to or higher than the lowest glass transition temperature (Tg) among the plurality of glass transition temperatures (Tg), and more preferably equal to or higher than the highest glass transition temperature (Tg) among the plurality of glass transition temperatures (Tg).

The same applies to the "softening temperature of the base sheet", as with the glass transition temperature (Tg). In cases where there are a plurality of types of constituent resins in the base sheet and the plurality of softening temperatures are different from each other, the heating temperature of the base sheet by the heating means is preferably at least equal to or higher than the lowest softening temperature among the plurality of softening temperatures, and more preferably equal to or higher than the highest softening temperature among the plurality of softening temperatures.

In cases where the base sheet includes two or more types of resins having different melting points, the heating temperature of the base sheet by the heating means is preferably below the lowest melting point among the plurality of melting points.

{Method for Measuring Glass Transition Temperature (Tg)}

The glass transition temperature is determined by measuring the heat quantity by using a DSC measurement device. More specifically, the measurement device used is a differential scanning calorimeter (Diamond DSC) from Perkin Elmer. A 10 mg test piece is sampled from the base sheet. As for the measurement conditions, the temperature is kept constant at 20° C. for 5 minutes, and then the temperature is raised from 20° C. to 320° C. at a rate of 5° C./minute, to obtain a DSC curve wherein the horizontal axis indicates temperature and the vertical axis indicates heat quantity. The glass transition temperature Tg is determined from the DSC curve.

If the insertion speed for inserting the projecting mold part 11 into the base sheet 2A is too slow, the resin will get heated and softened excessively, whereas if the insertion speed is too fast, heating and softening will be insufficient. Thus, from the viewpoint of forming the protrusion 3 efficiently, the insertion speed is preferably 0.1 mm/s or greater, more preferably 1 mm/s or greater, and preferably 1000 mm/s or less, more preferably 800 mm/s or less, and more specifically, preferably from 0.1 to 1000 mm/s, more preferably from 1 to 800 mm/s. The softening time is the time until the projecting mold part/protrusion is transported to the next step (cooling step) after stopping the elevation of the heated-state projecting mold part 11 while keeping the projecting mold part 11 inserted in the interior of the protrusion 3. Although a too-long softening time will result in excessive heating, from the viewpoint of supplementing insufficient heating, the softening time is preferably 0 seconds or longer, more preferably 0.1 seconds or longer, and preferably 10 seconds or less, more preferably 5 seconds or less, and more specifically, preferably from 0 to 10 seconds, more preferably from 0.1 to 5 seconds.

From the viewpoint of forming the protrusion 3 efficiently, the insertion height of the projecting mold part 11 inserted into the base sheet 2A is preferably 0.01 mm or greater, more preferably 0.02 mm or greater, and preferably 10 mm or less, more preferably 5 mm or less, and more specifically, preferably from 0.01 to 10 mm, more preferably from 0.02 to 5 mm. Herein, "insertion height" refers to the distance between the apex of the projecting mold part 11 and the other surface 2U (upper surface) of the base sheet 2A in a state where the projecting mold part 11 is inserted furthest in the base sheet 2A. So, the insertion height in the protrusion forming step refers to the distance measured in the perpendicular direction from the other surface 2U to the apex of the projecting mold part 11 in a state where the projecting mold part 11 has been inserted furthest in the protrusion forming step and the projecting mold part 11 has emerged from the other surface 2U of the base sheet 2A.

Next, in the manufacturing device 100A of the first embodiment, as illustrated in FIG. 4, the cooling section 20 is provided downstream of the protrusion forming section 10. As illustrated in FIG. 4, the cooling section 20 includes a cold air blowing device 21. In the first embodiment, after the protrusion forming step, cooling is performed by using this cold air blowing device 21 in a state where the projecting mold part 11 is inserted in the interior of the protrusion 3 (cooling step). More specifically, the cold air blowing device 21 covers the entirety of the other surface 2U side (upper surface side) and the one surface 2D side (lower surface side) of the continuous base sheet 2A being transported, and the continuous base sheet 2A is transported inside the cold air blowing device 21 along the transporting direction (Y direction). An air vent 22 (cf. FIG. 6(c)) for blowing cold air is provided inside the tunnel of the cold air blowing device 21 on the other surface 2U side (upper surface side) of the base sheet 2A, and cooling is performed by blowing cold air from the air vent 22. Note that the cooling temperature of the cold air blowing device 21 and the cooling time are controlled by the control means (not illustrated) provided to the manufacturing device 100A of the first embodiment.

In the cooling step of the first embodiment, as illustrated in FIG. 4, the box-motion-type protrusion forming section 10 is employed for transporting the base sheet 2A parallel to the transporting direction (Y direction) into the tunnel of the cold air blowing device 21 in a state where the projecting mold part 11 is inserted in the interior of the protrusion 3, and, as illustrated in FIG. 6(c), the protrusion 3 is cooled by blowing cold air from the air vent 22 arranged on the other surface 2U side (upper surface side) of the base sheet 2A inside the tunnel, with the projecting mold part 11 still inserted in the interior of the protrusion 3. Note that, during cooling, heating of the projecting mold part 11 with the heating heater device may be continued or stopped.

In cases where the heating means (not illustrated) of the projecting mold part 11 is a heating heater device as in the first embodiment, cooling may be performed naturally in the cooling section 20 provided downstream of the protrusion forming section 10. Active cooling, however, is preferable, and it is preferable to provide the cold air blowing device 21.

From the viewpoint of formation of the protrusion 3, the temperature of the cold air to be blown is preferably −50° C. or higher, more preferably −40° C. or higher, and preferably 26° C. or lower, more preferably 10° C. or lower, and more specifically, preferably from −50 to 26° C., more preferably from −40 to 10° C. From the viewpoint of balancing moldability and processing time, the cooling time for cooling by blowing the cold air is preferably 0.01 seconds or longer, more preferably 0.5 seconds or longer, and preferably 60 seconds or less, more preferably 30 seconds or less, and more specifically, preferably from 0.01 to 60 seconds, more preferably from 0.5 to 30 seconds.

Next, in the manufacturing device 100A of the first embodiment, as illustrated in FIG. 4, the release section 30 is provided downstream of the cooling section 20. In the first embodiment, the projecting mold part 11 is withdrawn from the interior of the protrusion 3 after the cooling step by using the box-motion-type protrusion forming section 10, to form a precursor 1A of the fine hollow protruding article 1 (release step). More specifically, in the release step of the first embodiment, as illustrated in FIG. 6(d), the projecting mold part 11 is lowered from the one surface 2D side (lower surface side) of the base sheet 2A by using the box-motion-type protrusion forming section 10, and the projecting mold part 11 is withdrawn from the state where the projecting mold part 11 is inserted in the interior of the protrusion 3, to form a precursor 1A of a continuous fine hollow protruding article, which ultimately becomes a fine hollow protruding article 1 having a hollow interior.

Next, in the manufacturing device 100A of the first embodiment, as illustrated in FIG. 4, the cutting section 40 is provided downstream of the release section 30. In the manufacturing device 100A of the first embodiment, the cutting section 40 includes a cutter part 41 having a cutter blade at its tip end, and an anvil part 42. The cutter blade of the cutter part 41 is formed so as to have a wider width than the entire width (length in the X direction) of the precursor 1A of the continuous fine hollow protruding article. In the first embodiment, after the release step, the precursor 1A of the continuous fine hollow protruding article is transported between the pair of the cutter part 41 and the anvil part 42, and each section between protrusions 3, 3 adjacent to one another in the transporting direction (Y direction) is cut with the cutter blade of the cutter part 41, to continuously manufacture pieces of fine hollow protruding articles 1.

Cutting of the precursor 1A of the continuous fine hollow protruding article only needs to be performed so as to extend along the width direction of each fine hollow protruding article 1, and for example, can be performed in a straight line along the width direction of each fine hollow protruding article 1. Alternatively, cutting may be performed such that the cutting line depicts a curve. In either case, it is preferable to employ a cutting pattern that does not give rise to trimmed parts as a result of cutting.

Next, in the manufacturing device 100A of the first embodiment, as illustrated in FIG. 4, the re-pitching section 50 is provided downstream of the cutting section 40. In the manufacturing device 100A of the first embodiment, the re-pitching section 50 includes: a plurality of rollers 51 arranged such that their rotation axes are parallel to one another; and an endless transporting belt 52 that bridges the rollers 51. A suction box 53 is provided inside the transporting belt 52. The transporting belt 52 is provided with a plurality of penetrating holes (not illustrated) for sucking air from the exterior of the circulating track toward the interior thereof by activating the suction box 53. Note that the transportation speed of the transporting belt 52 is faster than the transportation speed of the base sheet 2A up to the cutting section 40.

In the first embodiment, the pieces of fine hollow protruding articles 1 are continuously moved onto the fast transporting belt 52 while being sucked by the suction box 53 through the penetrating holes (not illustrated), and the distance between consecutive fine hollow protruding articles 1, 1 adjacent to one another in the transporting direction (Y direction) is widened, thereby rearranging the fine hollow protruding articles 1 with predetermined distances therebetween.

As described above, according to the manufacturing method of the first embodiment wherein fine hollow protruding articles 1 are manufactured by using the manufacturing device 100A of the first embodiment, the fine hollow protruding articles 1 can be manufactured by simple steps, and the fine hollow protruding articles 1 can be manufactured continuously and efficiently while suppressing an increase in cost.

Further, as described above, in the first embodiment, as illustrated in FIG. 6(a), the projecting mold part 11 is heated by the heating heater device only at the contact section TP of the base sheet 2A in contact with the projecting mold part 11 and thereby the contact section TP is softened. Thus, fine hollow protruding articles 1 can be manufactured continuously and efficiently while saving energy. In contrast, in cases where the entire resin needs to be heated to the same temperature as the projecting mold part, not only is energy efficiency poor, but also various other problems may arise—such as pitch discrepancies between protrusions, distortion of the sheet, and difficulty in continuously transporting the sheet—due to the entire sheet getting soft. The present invention (first invention), on the other hand, is advantageous in that heat due to heating by the projecting mold part 11 is transmitted efficiently to the contact section TP, and peripheral sections thereof are in an environment where heating can be left only to natural progression; thus, the aforementioned problems are prevented because only the section to be processed (the contact section) is heated.

Further, as described above, in the manufacturing device 100A of the first embodiment, the control means (not illustrated) controls the operations of the projecting mold parts 11, the heating condition of the heating means (not illustrated) of the projecting mold part 11, the cooling temperature of the cold air blowing device 21, and the cooling time. Thus, by controlling, for example, the insertion height of the projecting mold part 11 in the protrusion forming step with the control means (not illustrated), the insertion amount of the projecting mold part 11 into the base sheet 2A can be changed easily, and the protrusion height H1 of the fine hollow protruding article 1 to be manufactured can be controlled. Further, the thickness T1 of the protrusion 3 constituting the fine hollow protruding article 1, etc., can be controlled freely by controlling at least one of the heating condition of the projecting mold part 11, the softening time of the contact section TP of the base sheet 2A, and the insertion speed of the projecting mold part 11 into the base sheet 2A. Stated differently, the shape of the fine hollow protruding article 1 can be controlled freely by controlling at least one condition selected from a condition of the heating means (not illustrated) of the projecting mold part 11, the insertion height of the projecting mold part 11 into the base sheet 2A in the protrusion forming step, the softening time of the contact section TP of the base sheet 2A, the insertion speed of the projecting mold part 11 into the base sheet 2A, the shape of the projecting mold part 11, and a cooling condition in the cooling step.

Further, as described above, in the first embodiment, as illustrated in FIG. 4, the pair of supports 12, 12—which is arranged on the other surface 2U side (upper surface side) of the base sheet 2A—is used to support the base sheet 2A's respective lateral sides along the transporting direction (Y direction), and the projecting mold part 11 is brought into contact from the one surface 2D side (lower surface side) in the base sheet 2A's central section which is in a free floating state between the pair of supports 12, 12 (i.e., in a non-supported state that is not supported by the pair of supports 12, 12), to thereby soften the contact section TP with heat and form a protrusion 3. Because there is no need to provide a depression, etc., into which the projecting mold part 11 is fitted to form the protrusion, it is possible to suppress an increase in cost, and to precisely and efficiently form the protrusion 3 of the fine hollow protruding article 1 to be manufactured.

Next, the invention (first invention) will be described according to a second embodiment with reference to FIG. 7. Note that the following description mainly focuses on features that are different from those of the foregoing first embodiment.

In the manufacturing device 100A of the first embodiment used in the foregoing first embodiment, the heating means (not illustrated) of the projecting mold part 11 is a heating heater device. In the manufacturing device 100A of the second embodiment used in the second embodiment, an ultrasonic vibration device is used instead.

Figures 7A, 7B, 7C, 7D:
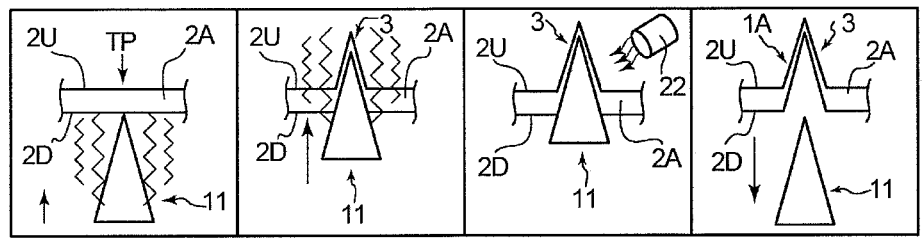
FIGS. 7(a) to 7(d) are diagrams illustrating steps for manufacturing a fine hollow protruding article by employing a manufacturing device of a second embodiment.

In cases where the heating means (not illustrated) of the projecting mold part 11 is an ultrasonic vibration device as in the manufacturing device 100A of the second embodiment, the contact section TP is softened by causing ultrasonic vibration of the projecting mold part 11 by the ultrasonic vibration device and generating heat in the contact section TP by friction, as illustrated in FIG. 7(a). Then, as illustrated in FIG. 7(b), while softening the contact section TP, the projecting mold part 11 is raised from the one surface 2D side (lower surface side) of the base sheet 2A toward the other surface 2U side (upper surface side) and is inserted into the base sheet 2A, to form a protrusion 3 that protrudes from the other surface 2U side (upper surface side) of the base sheet 2A. When the protrusion 3 has protruded to its set height, elevation of the projecting mold part 11 is stopped, and the protrusion 3 is transported to the next step in a state where the projecting mold part 11 is inserted in the interior of the protrusion 3. Ultrasonic vibration of the projecting mold part 11 by the ultrasonic vibration device is performed from immediately before the projecting mold part 11 comes into contact with the base sheet 2A until immediately before reaching the cooling section 20 in the next step (cooling step).

As regards the ultrasonic vibration of the projecting mold part 11 by the ultrasonic vibration device, from the viewpoint of forming the protrusion 3, the frequency is preferably 10 kHz or greater, more preferably 15 kHz or greater, and preferably 50 kHz or less, more preferably 40 kHz or less, and more specifically, preferably from 10 to 50 kHz, more preferably from 15 to 40 kHz. Further, from the viewpoint of forming the projecting mold part 11, the amplitude of the ultrasonic vibration of the projecting mold part 11 by the ultrasonic vibration device is preferably 1 μm or greater, more preferably 5 μm or greater, and preferably 60 μm or less, more preferably 50 μm or less, and more specifically, preferably from 1 to 60 μm, more preferably from 5 to 50 μm.

As described above, in the manufacturing device 100A of the second embodiment, the cooling section 20 includes a cold air blowing device 21 for active cooling. However, because the heating means (not illustrated) of the projecting mold part 11 is an ultrasonic vibration device, the cold air blowing device 21 does not necessarily have to be provided, and cooling can be achieved by simply turning off the vibration of the ultrasonic vibration device. From this viewpoint, using ultrasonic vibration as the heating means is preferable in terms that the device can be simplified and fine hollow protruding articles can be manufactured easily at high speed. Further, heat is less likely to be transmitted to sections of the base sheet 2A that are not in contact with the projecting mold part 11 and cooling is performed efficiently by stopping the application of ultrasonic vibration; this is advantageous in that deformation is less likely to occur in sections other than the section being molded.

The invention (second invention) is described below according to preferred embodiments thereof with reference to the drawings.

Figure 11:
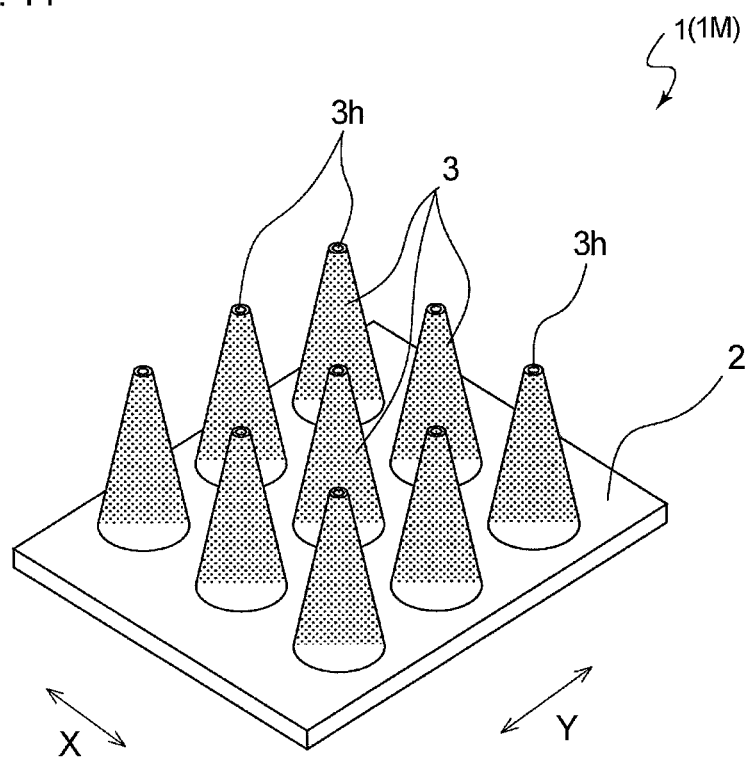
FIG. 11 is a schematic perspective view of an example of a fine hollow protruding article in which protrusions each having a through hole are arranged in an array, the fine hollow protruding article being manufactured by a method for manufacturing a fine hollow protruding article having a through hole according to the invention (second invention).

A manufacturing method of the invention (second invention) is a method for manufacturing a fine hollow protruding article having through holes. FIG. 11 illustrates a perspective view of a microneedle array 1M, which is a fine hollow protruding article 1 of an embodiment, manufactured according to a method for manufacturing a fine hollow protruding article 1 of a first embodiment. The microneedle array 1M of the present embodiment includes: a sheet-like basal portion 2; and a plurality of protrusions 3. The number of protrusions 3, the arrangement of the protrusions 3, and the shape of the protrusion 3 are not particularly limited, but preferably in the microneedle array 1M of the present embodiment, nine truncated circular-conic protrusions 3 are provided in an array (matrix) on the upper surface of the sheet-like basal portion 2. The nine protrusions 3 arranged in an array (matrix) are arranged in three rows along the Y direction, which is the direction in which the later-described base sheet 2A is transported (i.e., the longitudinal direction of the base sheet 2A), and in three columns along the X direction, which is the direction orthogonal to the transporting direction and which is the lateral direction of the base sheet 2A being transported. Note that FIG. 12 is a perspective view of the microneedle array 1M, focusing on a single protrusion 3 among the protrusions 3 arranged in an array (matrix) in the microneedle array 1M, and FIG. 13 is a cross-sectional view taken along line illustrated in FIG. 12.

Figure 12:
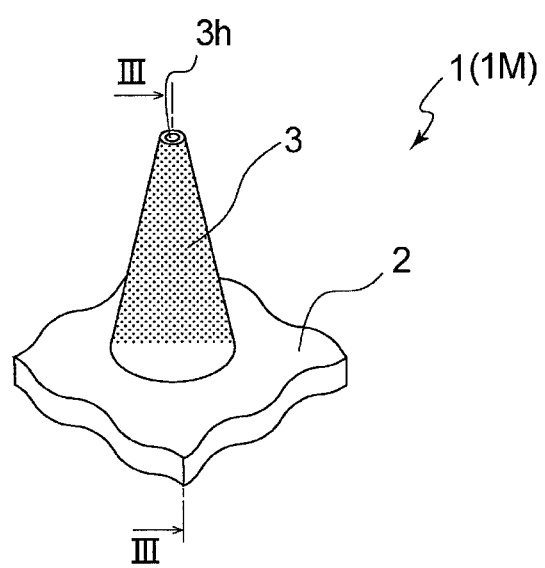
FIG. 12 is a perspective view of the fine hollow protruding article illustrated in FIG. 11, focusing on a single protrusion.
Figure 13:
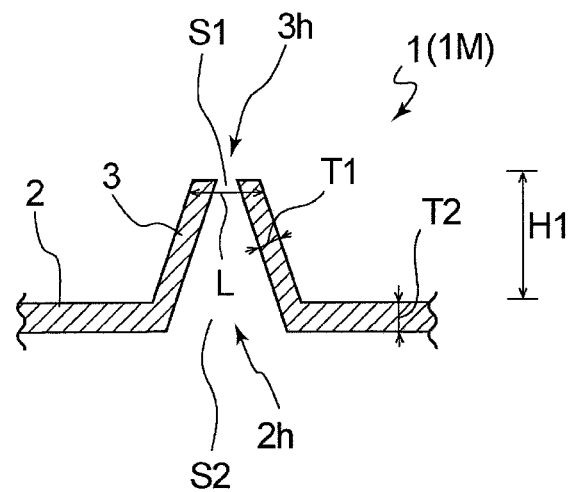
FIG. 13 is a cross-sectional view taken along line illustrated in FIG. 12.

As illustrated in FIG. 12, the microneedle array 1M has through holes 3h. Preferably, in the present embodiment, as illustrated in FIG. 13, in the microneedle array 1M, a space extending from the basal portion 2 to each through hole 3h is formed in the interior of each protrusion 3, and a through hole 3h is formed in the tip end of each protrusion 3. In the microneedle array 1M, the interior space of each protrusion 3 is formed in a shape corresponding to the outer shape of the protrusion 3, and in the present embodiment, is formed in a truncated circular-conic shape corresponding to the outer shape of the truncated circular-conic protrusion 3. It should be noted that, although the protrusion 3 in the present embodiment is truncated circular-conic, the protrusion may have a shape other than a truncated circular-conic shape, such as the shape of a circular cylinder, a prism, or a truncated pyramid.

In order for the tip end of each protrusion 3 to reach, for example, the stratum corneum, which is the outermost layer, or the dermis, which is a deeper layer, the protrusion height H1 of each protrusion 3 in the microneedle array 1M is preferably 0.01 mm or greater, more preferably 0.02 mm or greater, and preferably 10 mm or less, more preferably 5 mm or less, and more specifically, preferably from 0.01 to 10 mm, more preferably from 0.02 to 5 mm.

The average thickness T1 of each protrusion 3 is preferably 0.005 mm or greater, more preferably 0.01 mm or greater, and preferably 1.0 mm or less, more preferably 0.5 mm or less, and more specifically, preferably from 0.005 to 1.0 mm, more preferably from 0.01 to 0.5 mm.

The thickness T2 of the basal portion 2 is preferably 0.01 mm or greater, more preferably 0.02 mm or greater, and preferably 1.0 mm or less, more preferably 0.7 mm or less, and more specifically, preferably from 0.01 to 1.0 mm, more preferably from 0.02 to 0.7 mm.

The tip end size L, in diameter, of each protrusion 3 of the microneedle array 1M is preferably 1 μm or greater, more preferably 5 μm or greater, and preferably 500 μm or less, more preferably 300 μm or less, and more specifically, preferably from 1 to 500 μm, more preferably from 5 to 300 μm. The tip end diameter L of the fine hollow protruding article 1 is the length at the widest position at the tip end of each protrusion 3. By setting the tip end diameter within the aforementioned range, the microneedle array 1M hardly causes any pain when it is inserted into the skin.

As illustrated in FIG. 13, the fine hollow protruding article 1 has: a through hole 3h located at the tip end section of each protrusion 3; and a basal-side through hole 2h located at the lower surface of the basal portion 2 corresponding to each protrusion 3. In the microneedle array 1M of the present embodiment, the through hole 3h and the basal-side through hole 2h are formed concentrically.

The opening area S1 of the through hole 3h is preferably 0.7 μm² or greater, more preferably 20 μm² or greater, and preferably 200000 μm² or less, more preferably 70000 μm² or less, and more specifically, preferably from 0.7 to 200000 μm², more preferably from 20 to 70000 μm².

The opening area S2 of the basal-side through hole 2h is preferably 0.007 mm² or greater, more preferably 0.03 mm² or greater, and preferably 20 mm² or less, more preferably 7 mm² or less, and more specifically, preferably from 0.007 to 20 mm², more preferably from 0.03 to 7 mm².

The nine protrusions 3 arranged in an array (matrix) on the upper surface of the sheet-like basal portion 2 are preferably arranged such that the center-to-center distance in the longitudinal direction (Y direction) is uniform and the center-to-center distance in the lateral direction (X direction) is uniform, and preferably, the center-to-center distance in the longitudinal direction (Y direction) is the same as the center-to-center distance in the lateral direction (X direction). Preferably, the center-to-center distance in the longitudinal direction (Y direction) between the protrusions 3 is preferably 0.01 mm or greater, more preferably 0.05 mm or greater, and preferably 10 mm or less, more preferably 5 mm or less, and more specifically, preferably from 0.01 to 10 mm, more preferably from 0.05 to 5 mm. The center-to-center distance in the lateral direction (X direction) between the protrusions 3 is preferably 0.01 mm or greater, more preferably 0.05 mm or greater, and preferably 10 mm or less, more preferably 5 mm or less, and more specifically, preferably from 0.01 to 10 mm, more preferably from 0.05 to 5 mm.

Figure 14:
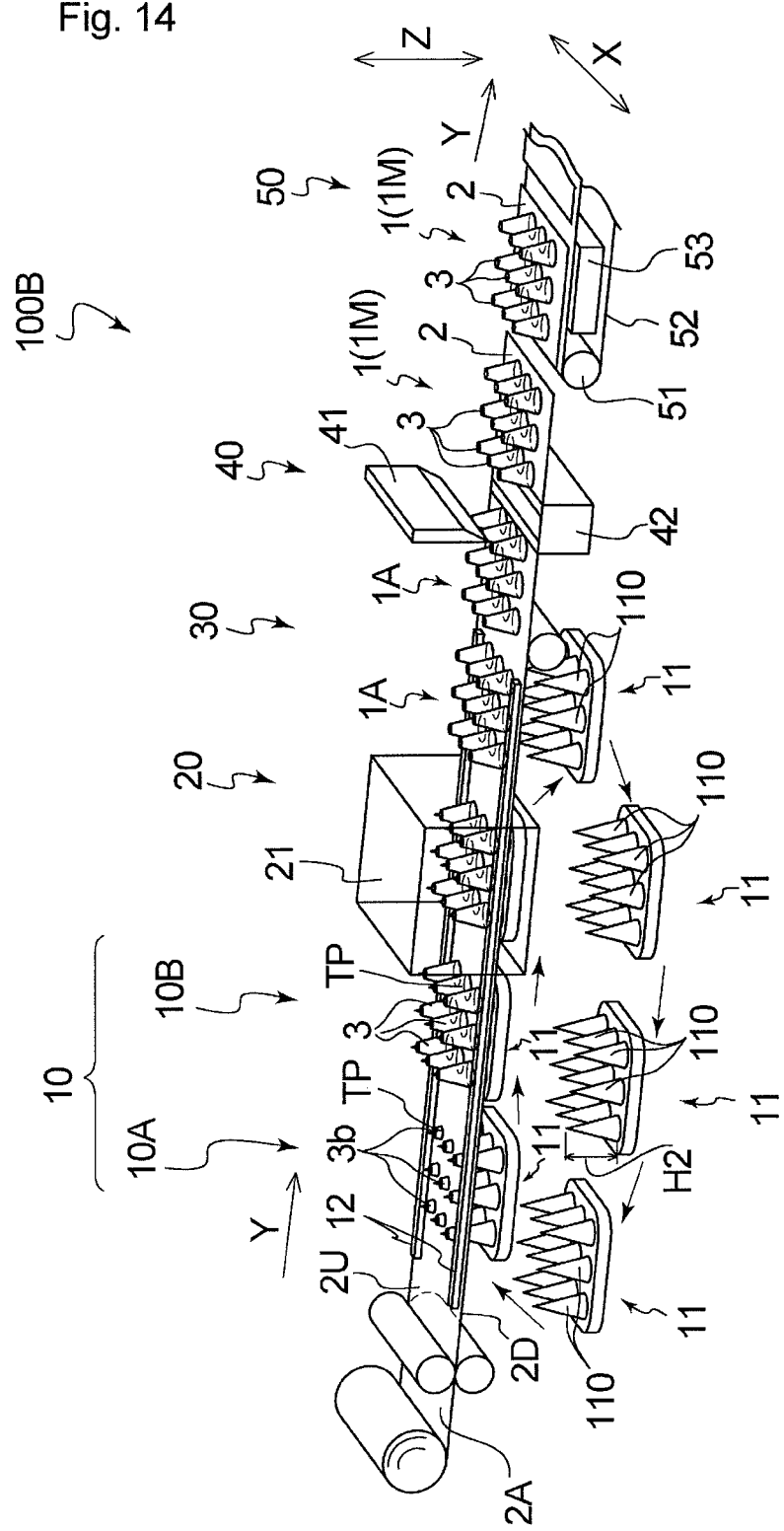
FIG. 14 is a diagram illustrating an overall configuration of a first embodiment of a manufacturing device for manufacturing the fine hollow protruding article illustrated in FIG. 11.
Figure 15:
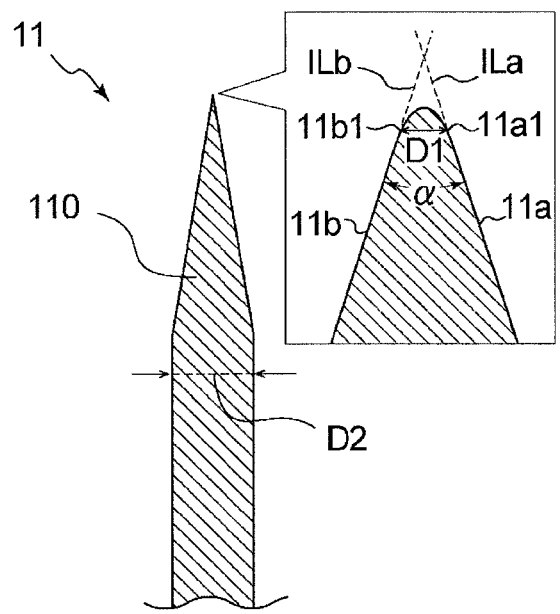
FIG. 15 is an explanatory diagram illustrating a method for measuring the tip end diameter and the tip end angle of a projecting mold of a projecting mold part.

Next, a method for manufacturing a fine hollow protruding article of the invention (second invention) is described with reference to FIGS. 14 to 16, taking, as an example, a method for manufacturing the aforementioned microneedle array 1M serving as a fine hollow protruding article 1. FIG. 14 illustrates an overall configuration of a manufacturing device 100B according to the first embodiment used for implementing the manufacturing method of the first embodiment. It should be noted that, each protrusion 3 of the microneedle array 1M is actually very small as described above, but for the sake of explanation, each protrusion 3 of the microneedle array 1M is illustrated very large in FIG. 14.

The manufacturing device 100B of the first embodiment illustrated in FIG. 14 includes, from the upstream side toward the downstream side: a protrusion precursor forming section 10A for forming hollow protrusion precursors 3b in a base sheet 2A; a protrusion elongating section 10B for forming protrusions 3 in the base sheet 2A; a cooling section 20; a release section 30 where the later-described projecting mold part 11 is withdrawn; a cutting section 40 where each microneedle array 1M is cut; and a re-pitching section 50 where the interval between the microneedle arrays 1M is adjusted. It should be noted that the manufacturing device 100B includes a protrusion forming section 10 that is for forming the protrusions 3 and that includes the protrusion precursor forming section 10A and the protrusion elongating section 10B, and in the present invention (second invention), the step from the protrusion precursor forming step using the protrusion precursor forming section 10A up to the protrusion elongating step using the protrusion elongating section 10B is referred to as the protrusion forming step.

In the following description, the direction in which the base sheet 2A is transported (the longitudinal direction of the base sheet 2A) is referred to as the Y direction, the direction orthogonal to the transporting direction, which is the lateral direction of the base sheet 2A being transported, is referred to as the X direction, and the thickness direction of the base sheet 2A being transported is referred to as the Z direction.

As illustrated in FIG. 14, the protrusion precursor forming section 10A and the protrusion elongating section 10B of the protrusion forming section 10 include projecting mold parts 11 each including a heating means (not illustrated). The projecting mold part 11 includes projecting molds 110 corresponding to the number and arrangement of the protrusions 3 on the microneedle array 1M to be manufactured and substantially to the outer shape of each protrusion 3. In the manufacturing device 100B of the first embodiment, nine circular-conic projecting molds 110 are provided corresponding to the nine truncated circular-conic protrusions 3.

In the manufacturing device 100B of the first embodiment, the heat quantity applied from the projecting mold part 11 to the base sheet 2A in the protrusion elongating section 10B is greater than the heat quantity applied from the projecting mold part 11 to the base sheet 2A in the protrusion precursor forming section 10A. Herein, the "heat quantity applied to the base sheet 2A" refers to the heat quantity per unit insertion height applied to the base sheet 2A. More specifically, in order to make the heat quantity applied from the projecting mold part 11 to the base sheet 2A in the protrusion elongating section 10B greater than the heat quantity applied from the projecting mold part 11 to the base sheet 2A in the protrusion precursor forming section 10A, at least one of the following conditions is satisfied: (a) as regards the insertion speed for inserting the projecting mold part 11 into the base sheet 2A, the insertion speed in the protrusion elongating section 10B is slower than the insertion speed in the protrusion precursor forming section 10A; (b) in cases where the heating means (not illustrated) of the projecting mold part 11 is an ultrasonic vibration device, the frequency of the ultrasonic vibration of the projecting mold part 11 in the protrusion elongating section 10B is higher than the frequency of the ultrasonic vibration of the projecting mold part 11 in the protrusion precursor forming section 10A; (c) in cases where the heating means (not illustrated) of the projecting mold part 11 is an ultrasonic vibration device, the amplitude of the ultrasonic vibration of the projecting mold part 11 in the protrusion elongating section 10B is greater than the amplitude of the ultrasonic vibration of the projecting mold part 11 in the protrusion precursor forming section 10A; and (d) in cases where the heating means (not illustrated) of the projecting mold part 11 is a heating heater, the heater temperature of the projecting mold part 11 in the protrusion elongating section 10B is higher than the heater temperature of the projecting mold part 11 in the protrusion precursor forming section 10A. It should be noted that, in the manufacturing device used for the method for manufacturing a fine hollow protruding article of the present invention (second invention), no other heating means is provided except for the heating means (not illustrated) of each projecting mold part 11. It should be noted that, in this Specification, "no other heating means is provided except for the heating means of the projecting mold part 11" not only refers to cases where other heating means are completely eliminated, but also refers to cases where a means for heating to a temperature below the softening temperature of the base sheet 2A, or to a temperature below the glass transition temperature, is provided. Note, however, that it is preferable to completely eliminate all other heating means.

In the manufacturing device 100B of the first embodiment, the heating means (not illustrated) of the projecting mold part 11 is an ultrasonic vibration device. In the first embodiment, first, a continuous base sheet 2A is paid out from a material roll of a base sheet 2A including a thermoplastic resin, and is transported in the Y direction. Then, the projecting mold part 11 is brought into contact from the one surface 2D side of the continuous base sheet 2A being transported in the Y direction, and, while softening, with heat, a contact section TP in the base sheet 2A where the projecting mold part contacts the base sheet, the projecting mold part 11 is inserted into the base sheet 2A, to form a hollow protrusion precursor 3b that protrudes from the other surface 2U of the base sheet 2A and that has a through hole 3h that penetrates the tip end on the other surface 2U side of the base sheet 2A (protrusion precursor forming step). Preferably, in the manufacturing device 100B of the first embodiment, nine circular-conic projecting molds 110 with a sharp tip end are arranged in the projecting mold part 11 so that their tip ends face upward, and the projecting mold part 11 is movable at least vertically in the thickness direction (Z direction). More preferably, in the manufacturing device 100B of the first embodiment, the projecting mold part 11 can move vertically in the thickness direction (Z direction) by an electric actuator (not illustrated), and can travel together with the base sheet 2A in the transporting direction (Y direction). The operation (electric actuator) of the projecting mold part 11 is controlled by a control means (not illustrated) provided to the manufacturing device 100B of the first embodiment. As described above, the manufacturing device 100B of the first embodiment is a device including projecting mold parts 11 of the so-called "box-motion-type" which follow an endless track. Heating of the heating means (not illustrated) of the projecting mold part 11 is also controlled by the control means (not illustrated) provided to the manufacturing device 100B of the first embodiment.

The base sheet 2A is a sheet that constitutes the basal portion 2 of the microneedle array 1M being manufactured, and includes a thermoplastic resin. Examples of the thermoplastic resin include poly-fatty acid esters, polycarbonate, polypropylene, polyethylene, polyester, polyamide, polyamide imide, polyether ether ketone, polyetherimide, polystyrene, polyethylene terephthalate, polyvinyl chloride, nylon resin, acrylic resin, and combinations thereof. From the viewpoint of biodegradability, poly-fatty acid esters are preferably used. Concrete examples of poly-fatty acid esters include polylactic acid, polyglycolic acid, and combinations thereof. Note that the base sheet 2A may be formed of a mixture including, for example, hyaluronic acid, collagen, starch, cellulose, etc., in addition to thermoplastic resin. The thickness of the base sheet 2A is substantially the same as the thickness T2 of the basal portion 2 of the microneedle array 1M being manufactured.

The outer shape of the projecting mold 110 of the projecting mold part 11 has a sharper shape than the outer shape of the protrusion 3 of the microneedle array 1M. The height H2 (cf. FIG. 14) of the projecting mold 110 of the projecting mold part 11 is formed higher than the height H1 of the microneedle array 1M being manufactured, and is preferably 0.01 mm or greater, more preferably 0.02 mm or greater, and preferably 30 mm or less, more preferably 20 mm or less, and more specifically, preferably from 0.01 to 30 mm, more preferably from 0.02 to 20 mm. The tip end diameter D1 (cf. FIG. 15) of the projecting mold 110 of the projecting mold part 11 is preferably 0.001 mm or greater, more preferably 0.005 mm or greater, and preferably 1 mm or less, more preferably 0.5 mm or less, and more specifically, preferably from 0.001 to 1 mm, more preferably from 0.005 to 0.5 mm. The tip end diameter D1 of the projecting mold 110 of the projecting mold part 11 is measured as follows.

The base diameter D2 (cf. FIG. 15) of the projecting mold 110 of the projecting mold part 11 is preferably 0.1 mm or greater, more preferably 0.2 mm or greater, and preferably 5 mm or less, more preferably 3 mm or less, and more specifically, preferably from 0.1 to 5 mm, more preferably from 0.2 to 3 mm.

From the viewpoint of easily achieving sufficient strength, the tip end angle α (cf. FIG. 15) of the projecting mold 110 of the projecting mold part 11 is preferably 1 degree or greater, more preferably 5 degrees or greater. From the viewpoint of obtaining a protrusion 3 having an appropriate angle, the tip end angle α is preferably 60 degrees or less, more preferably 45 degrees or less, and more specifically, preferably from 1 to 60 degrees, more preferably from 5 to 45 degrees. The tip end angle α of the projecting mold 110 of the projecting mold part 11 is measured as follows.

{Measurement of Tip End Diameter of Projecting Mold 110 of Projecting Mold Part 11}

The tip end portion of the projecting mold 110 of the projecting mold part 11 is observed in an enlarged state under a predetermined magnification using a scanning electron microscope (SEM) or a microscope. Next, as illustrated in FIG. 15, an imaginary straight line ILa is extended along the straight-line portion of one lateral side 11a of the two lateral sides 11a, 11b. Also, an imaginary straight line ILb is extended along the straight-line portion of the other lateral side 11b. The point where the lateral side 11a separates from the imaginary straight line ILa on the tip end side is defined as a first tip end point 11a1, and the point where the other lateral side 11b separates from the imaginary straight line ILb is defined as a second tip end point 11b1. The length D1 of a straight line that connects the first tip end point 11a1 and the second tip end point 11b1 defined as above is measured using a scanning electron microscope (SEM) or a microscope, and the measured length of the straight line is defined as the tip end diameter of the projecting mold 110.

{Measurement of Tip End Angle α of Projecting Mold 110 of Projecting Mold Part 11}

The tip end portion of the projecting mold 110 of the projecting mold part 11 is observed in an enlarged state under a predetermined magnification using a scanning electron microscope (SEM) or a microscope. Next, as illustrated in FIG. 15, an imaginary straight line ILa is extended along the straight-line portion of one lateral side 11a of the two lateral sides 11a, 11b. Also, an imaginary straight line ILb is extended along the straight-line portion of the other lateral side 11b. The angle formed between the imaginary straight line ILa and the imaginary straight line ILb is measured using a scanning electron microscope (SEM) or a microscope, and the measured angle is defined as the tip end angle α of the projecting mold 110 of the projecting mold part 11.

The projecting mold part 11 is formed of a high-strength material that is hard to bend/break. Examples of materials for the projecting mold part 11 include metals, such as steel, stainless steel, aluminum, aluminum alloy, nickel, nickel alloy, cobalt, cobalt alloy, copper, copper alloy, beryllium copper, and beryllium copper alloy, and ceramics.

In the manufacturing device 100B of the first embodiment, as illustrated in FIG. 14, the protrusion precursor forming section 10A includes a support 12 that supports the base sheet 2A when the projecting mold part 11 is inserted into the base sheet 2A. The support 12 is arranged on the other surface 2U side of the base sheet 2A, and serves to make the base sheet 2A less likely to warp/bend when the projecting mold part 11 is inserted from the one surface 2D side. Thus, the support 12 is arranged in a section, of the base sheet 2A, other than a region where the projecting mold part 11 is inserted into the base sheet 2A. In the manufacturing device 100B of the first embodiment, the support 12 is constituted by a pair of plate-like members extending parallel to the transporting direction (Y direction) on the base sheet 2A's respective lateral sides along the transporting direction (Y direction). The supports 12 extend from the protrusion precursor forming section 10A, through the protrusion elongating section 10B and the cooling section 20, and up to a position where the release section 30 terminates.

The material constituting the support 12 may be the same as the material of the projecting mold part 11, and may be formed of a synthetic resin, for example.

As illustrated in FIG. 14, in the protrusion precursor forming step of the first embodiment, the pair of supports 12, 12—which is arranged on the other surface 2U side (upper surface side) of the continuous base sheet 2A paid out from the material roll and being transported in the Y direction—supports the base sheet 2A's respective lateral sides along the transporting direction (Y direction). Then, by using the box-motion-type projecting mold part 11, the tip end portion of each projecting mold 110 of the projecting mold part 11 is brought into contact from the one surface 2D (lower surface) in a section, of the base sheet 2A, that is not supported by the supports 12—i.e., in a central region of the base sheet 2A between the pair of supports 12, 12. That is, in the protrusion precursor forming step, the other surface 2U (upper surface) corresponding to the contact section TP of the base sheet 2A in contact with each projecting mold 110 of the projecting mold part 11 is in a free floating state, without being provided with a depression, etc., into which the projecting mold part 11 is fitted to form a protruding article.

Figures 16A, 16B, 16C, 16D, 16E:
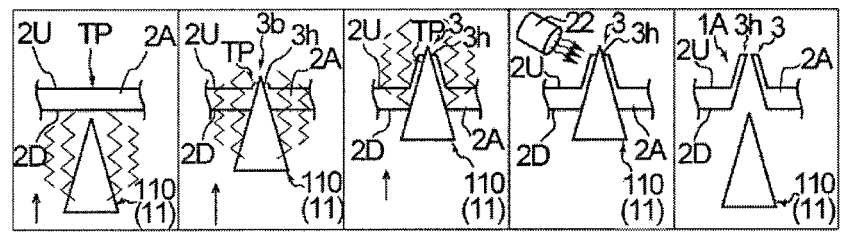
FIGS. 16(a) to 16(e) are diagrams illustrating steps for manufacturing a fine hollow protruding article having a through hole by employing the manufacturing device illustrated in FIG. 14.

Then, as illustrated in FIG. 16(a), in the first embodiment, the ultrasonic vibration device causes ultrasonic vibration of the projecting mold part 11 at each of the contact sections TP, and the contact sections TP are softened by generating heat in the contact sections TP by friction. Then, in the protrusion precursor forming step of the first embodiment, as illustrated in FIG. 16(b), while softening the contact section TP, the projecting mold part 11 is raised from the one surface 2D (lower surface) of the base sheet 2A toward the other surface 2U (upper surface) and the tip end portion of each projecting mold 110 is inserted into the base sheet 2A, to form a hollow protrusion precursor 3b that protrudes from the other surface 2U (upper surface) of the base sheet 2A and that has a penetrating through hole 3h.

In the protrusion precursor forming step of the first embodiment, as regards the ultrasonic vibration of the projecting mold part 11 by the ultrasonic vibration device, from the viewpoint of forming the protrusion precursor 3b having a through hole 3h, the vibration frequency (referred to hereinafter as "frequency") is preferably 10 kHz or greater, more preferably 15 kHz or greater, and preferably 50 kHz or less, more preferably 40 kHz or less, and more specifically, preferably from 10 to 50 kHz, more preferably from 15 to 40 kHz.

Further, from the viewpoint of forming the protrusion precursor 3b having a through hole 3h, the amplitude of the ultrasonic vibration of the projecting mold part 11 by the ultrasonic vibration device is preferably 1 μm or greater, more preferably 5 μm or greater, and preferably 60 μm or less, more preferably 50 μm or less, and more specifically, preferably from 1 to 60 μm, more preferably from 5 to 50 μm. In cases of using an ultrasonic vibration device as in the first embodiment, in the protrusion precursor forming step, the frequency and the amplitude of the ultrasonic vibration of the projecting mold part 11 simply need to be adjusted to fall within the aforementioned ranges.

In the protrusion precursor forming step of the first embodiment, if the insertion speed for inserting the projecting mold part 11 into the base sheet 2A is too slow, the resin will get softened excessively and the through hole 3h will become too large, whereas if the insertion speed is too fast, softening will be insufficient and no through hole 3h will be formed. Thus, from the viewpoint of efficiently forming the protrusion precursor 3b having a through hole 3h, the insertion speed is preferably 0.1 mm/s or greater, more preferably 1 mm/s or greater, and preferably 1000 mm/s or less, more preferably 800 mm/s or less, and more specifically, preferably from 0.1 to 1000 mm/s, more preferably from 1 to 800 mm/s.

In the protrusion precursor forming step of the first embodiment, from the viewpoint of efficiently forming the protrusion precursor 3b having a through hole 3h, the insertion height of the projecting mold part 11 inserted into the base sheet 2A is preferably 0.001 mm or greater, more preferably 0.01 mm or greater, and preferably 2 mm or less, more preferably 1 mm or less, and more specifically, preferably from 0.001 to 2 mm, more preferably from 0.01 to 1 mm. Herein, "insertion height" refers to the distance between the apex of the projecting mold 110 of the projecting mold part 11 and the other surface 2U of the base sheet 2A in a state where the projecting mold 110 of the projecting mold part 11 is inserted in the base sheet 2A. So, the insertion height in the protrusion precursor forming step refers to the distance measured in the perpendicular direction from the other surface 2U to the apex of the projecting mold 110 in a state where the projecting mold 110 has been inserted furthest in the protrusion precursor forming step and the projecting mold 110 has emerged from the other surface 2U of the base sheet 2A.

Next, in the manufacturing device 100B of the first embodiment, as illustrated in FIG. 14, a protrusion elongating section 10B is provided downstream of the protrusion precursor forming section 10A. In the first embodiment, after the protrusion precursor forming step, the projecting mold part 11 is further inserted into the base sheet 2A in a state where the projecting mold part 11 is inserted in the interior of the protrusion precursor 3b while softening, with heat, the contact section TP in the base sheet 2A, to form a protrusion 3 that further protrudes by a longer distance from the other surface 2U of the base sheet 2A (protrusion elongating step). Preferably, in the manufacturing device 100B of the first embodiment, the projecting molds 110 of the projecting mold part 11 are further inserted into the base sheet 2A by further moving the box-motion-type projecting mold part 11 upward in the thickness direction (Z direction) by the electric actuator (not illustrated) while further softening the respective contact sections TP in the base sheet 2A by causing ultrasonic vibration of the projecting mold part 11 by the ultrasonic vibration device and generating heat in the contact sections TP by friction in a state where the projecting molds 110 of the projecting mold part 11 are inserted in the interior of the respective protrusion precursors 3b, to form respective protrusions 3 that further protrude from the other surface 2U of the base sheet 2A. Also, by using the box-motion-type projecting mold part 11, the protrusions 3—which are arranged in an array and in which the respective projecting molds 110 of the projecting mold part 11 are inserted—are moved parallel to the transporting direction (Y direction) of the base sheet 2A. Note that, in the protrusion forming step of the first embodiment, as illustrated in FIG. 14, the pair of supports 12, 12—which is arranged on the other surface 2U side (upper surface side) of the continuous base sheet 2A being transported in the Y direction—supports the base sheet 2A's respective lateral sides along the transporting direction (Y direction).

In the protrusion elongating step of the first embodiment, as illustrated in FIG. 16(c), the frequency and amplitude of the ultrasonic vibration of the projecting mold part 11 by the ultrasonic vibration device are the same as the frequency and amplitude of the ultrasonic vibration in the protrusion precursor forming step. Note that the opening area of the through hole 3h of each protrusion 3 formed in the protrusion elongating step is equal to or greater than the opening area S1 of the through hole 3h of the protrusion precursor 3b formed in the protrusion precursor forming step, but is preferably the same as the opening area S1.

In the protrusion elongating step of the first embodiment, the insertion speed for inserting the projecting mold part 11 into the base sheet 2A is slower than the insertion speed for inserting the projecting mold part 11 into the base sheet 2A in the protrusion precursor forming step. In the protrusion elongating step of the first embodiment, if the insertion speed for inserting the projecting mold part 11 into the base sheet 2A is too slow, the resin will get softened excessively and the size of the through hole 3h will change too greatly, whereas if the insertion speed is too fast, softening will be insufficient and the height of the protrusion 3 is likely to become insufficient. Thus, from the viewpoint of efficiently forming the protrusion 3 having a through hole 3h, the insertion speed is preferably 0.1 mm/s or greater, more preferably 1 mm/s or greater, and preferably 1000 mm/s or less, more preferably 800 mm/s or less, and more specifically, preferably from 0.1 to 1000 mm/s, more preferably from 1 to 800 mm/s.

The softening time is the time until the projecting mold part/protrusion is transported to the next step (cooling step) after stopping the elevation of the heated-state projecting mold part 11 while keeping the projecting molds 110 of the projecting mold part 11 inserted in the interior of the respective protrusions 3. In the protrusion elongating step of the first embodiment, although a too-long softening time will result in excessive softening of the respective contact sections TP in the base sheet 2A, from the viewpoint of supplementing insufficient softening, the softening time is preferably 0 seconds or longer, more preferably 0.1 seconds or longer, and preferably 10 seconds or less, more preferably 5 seconds or less, and more specifically, preferably from 0 to 10 seconds, more preferably from 0.1 to 5 seconds.

In the protrusion elongating step of the first embodiment, from the viewpoint of efficiently forming the protrusion 3 having a through hole 3h, the insertion height of the projecting mold part 11 inserted into the base sheet 2A is preferably 0.01 mm or greater, more preferably 0.02 mm or greater, and preferably 10 mm or less, more preferably 5 mm or less, and more specifically, preferably from 0.01 to 10 mm, more preferably from 0.02 to 5 mm.

As described above, in the first embodiment, the condition of the heating means (not illustrated) of the projecting mold part 11 in the protrusion precursor forming step is the same as the condition of the heating means (not illustrated) of the projecting mold part 11 in the protrusion elongating step; and the speed for further inserting the projecting mold part 11 into the base sheet 2A in the protrusion elongating step is slower than the speed for inserting the projecting mold part 11 into the base sheet 2A in the protrusion precursor forming step. More specifically, in the manufacturing device 100B of the first embodiment, the heating means (not illustrated) of the projecting mold part 11 is an ultrasonic vibration device, and the frequency and amplitude of the ultrasonic vibration of the projecting mold part 11 in the protrusion elongating section 10B are the same as the frequency and amplitude of the ultrasonic vibration of the projecting mold part 11 in the protrusion precursor forming section 10A, thus not satisfying the aforementioned conditions (b) and (c). However, in the first embodiment, as regards the insertion speed for inserting the projecting mold part 11 into the base sheet 2A, the insertion speed in the protrusion elongating step is slower than the insertion speed in the protrusion precursor forming step, thus satisfying the aforementioned condition (a). Thus, the heat quantity applied from the projecting mold part 11 to the base sheet 2A in the protrusion elongating step is greater than the heat quantity applied from the projecting mold part 11 to the base sheet 2A in the protrusion precursor forming step.

Further, in the manufacturing device 100B of the first embodiment, because box-motion-type projecting mold parts 11 are used, the insertion speed of the projecting mold part 11 into the base sheet 2A is made slower continuously from the protrusion precursor forming step to the protrusion elongating step. Stated differently, the insertion speed is gradually reduced. Thus, in the first embodiment, the heat quantity per unit insertion height applied from the projecting mold part 11 to the base sheet 2A in the protrusion precursor forming step and the heat quantity per unit insertion height applied from the projecting mold part 11 to the base sheet 2A in the protrusion elongating step continuously change from the latter part of the protrusion precursor forming step to the former part of the protrusion elongating step. Note that the "heat quantity per unit insertion height" is a value found, for each step, by dividing the total heat quantity applied to the base sheet 2A by the distance of movement of the projecting mold part 11. For example, in the protrusion precursor forming step, the "heat quantity per unit insertion height" is a value found by dividing the total heat quantity applied to the base sheet 2A from when the projecting mold part 11 has come into contact with the base sheet 2A until the end of this step, by the total distance of movement in this step.

Next, in the manufacturing device 100B of the first embodiment, as illustrated in FIG. 14, a cooling section 20 is provided downstream of the protrusion forming step, more specifically, downstream of the protrusion elongating section 10B in the protrusion forming step. As illustrated in FIG. 14, the cooling section 20 includes a cold air blowing device 21. In the first embodiment, after the protrusion elongating step, the protrusions 3 are cooled by using this cold air blowing device 21 in a state where the projecting mold part 11 is inserted in the interior of the protrusions 3 (cooling step). More specifically, the cold air blowing device 21 covers the entirety of the other surface 2U side (upper surface side) and the one surface 2D side (lower surface side) of the continuous base sheet 2A being transported, and the continuous base sheet 2A is transported inside the cold air blowing device 21 along the transporting direction (Y direction). An air vent 22 (cf. FIG. 16(d)) for blowing cold air is provided inside the tunnel of the cold air blowing device 21 on the other surface 2U side (upper surface side) of the base sheet 2A, and cooling is performed by blowing cold air from the air vent 22. Note that the cooling temperature of the cold air blowing device 21 and the cooling time are controlled by the control means (not illustrated) provided to the manufacturing device 100B of the first embodiment.

In the cooling step of the first embodiment, as illustrated in FIG. 14, the box-motion-type projecting mold parts 11 are employed for transporting the base sheet 2A parallel to the transporting direction (Y direction) into the tunnel of the cold air blowing device 21 in a state where the projecting molds 110 of the projecting mold part 11 are inserted in the interior of the respective protrusions 3, and, as illustrated in FIG. 16(d), the protrusions 3 are cooled by blowing cold air from the air vent 22 arranged on the other surface 2U side (upper surface side) of the base sheet 2A inside the tunnel, with the projecting molds 110 of the projecting mold part 11 still inserted in the interior of the respective protrusions 3. Note that, during cooling, ultrasonic vibration of the projecting mold part 11 by the ultrasonic vibration device may be continued or stopped, but from the viewpoint of preventing the shape of the protrusions 3 from deforming unduly and maintaining their shape constant, it is preferable that the ultrasonic vibration is stopped.

From the viewpoint of formation of the protrusion 3 having a through hole 3h, the temperature of the cold air to be blown is preferably $-50°$ C. or higher, more preferably $-40°$ C. or higher, and preferably $26°$ C. or lower, more preferably $10°$ C. or lower, and more specifically, preferably from $-50$ to $26°$ C., more preferably from $-40$ to $10°$ C.

From the viewpoint of balancing moldability and processing time, the cooling time for cooling by blowing the cold air is preferably 0.01 seconds or longer, more preferably 0.5 seconds or longer, and preferably 60 seconds or less, more preferably 30 seconds or less, and more specifically, preferably from 0.01 to 60 seconds, more preferably from 0.5 to 30 seconds.

Next, in the manufacturing device 100B of the first embodiment, as illustrated in FIG. 14, a release section 30 is provided downstream of the cooling section 20. In the first embodiment, the projecting mold part 11 is withdrawn from the interior of the protrusion 3 after the cooling step, to form a precursor 1A of the microneedle array 1M (release step). More specifically, in the release step of the first embodiment, as illustrated in FIG. 16(e), the projecting mold part 11 is lowered from the one surface 2D (lower surface) of the base sheet 2A by using the box-motion-type projecting mold part 11, and the projecting molds 110 of the projecting mold part 11 are withdrawn from the state where the projecting molds 110 of the projecting mold part 11 are inserted in the interior of the respective protrusions 3, to form a precursor 1A of a continuous fine hollow protruding article, which ultimately becomes a microneedle array 1M wherein protrusions 3 each having a through hole 3h and having a hollow interior are arranged in an array.

Next, in the manufacturing device 100B of the first embodiment, as illustrated in FIG. 14, a cutting section 40 is provided downstream of the release section 30. In the manufacturing device 100B of the first embodiment, the cutting section 40 includes a cutter part 41 having a cutter blade at its tip end, and an anvil part 42. The cutter blade of the cutter part 41 is formed so as to have a wider width than the entire width (length in the X direction) of the precursor 1A of the continuous fine hollow protruding article. In the first embodiment, after the release step, the precursor 1A of the continuous fine hollow protruding article is transported between the pair of the cutter part 41 and the anvil part 42, and each section between arrays of protrusions 3, 3 adjacent to one another in the transporting direction (Y direction) is cut with the cutter blade of the cutter part 41, to continuously manufacture pieces of microneedle arrays 1M wherein protrusions 3 each having a through hole 3h are arranged in an array.

Cutting of the precursor 1A of the continuous fine hollow protruding article only needs to be performed so as to extend along the lateral direction of each microneedle array 1M, and for example, can be performed in a straight line along the lateral direction of each microneedle array 1M. Alternatively, cutting may be performed such that the cutting line depicts a curve. In either case, it is preferable to employ a cutting pattern that does not give rise to trimmed parts as a result of cutting.

Next, in the manufacturing device 100B of the first embodiment, as illustrated in FIG. 14, a re-pitching section 50 is provided downstream of the cutting section 40. In the manufacturing device 100B of the first embodiment, the re-pitching section 50 includes: a plurality of rollers 51 arranged such that their rotation axes are parallel to one another; and an endless transporting belt 52 that bridges the rollers 51. A suction box 53 is provided inside the transporting belt 52. The transporting belt 52 is provided with a plurality of penetrating holes (not illustrated) for sucking air from the exterior of the circulating track toward the interior thereof by activating the suction box 53. Note that the transportation speed of the transporting belt 52 is faster than the transportation speed of the base sheet 2A up to the cutting section 40.

In the first embodiment, the pieces of microneedle arrays 1M are continuously moved onto the fast transporting belt 52 while being sucked by the suction box 53 through the penetrating holes (not illustrated), and the distance between consecutive microneedle arrays 1M, 1M adjacent to one another in the transporting direction (Y direction) is widened, thereby rearranging the microneedle arrays 1M with predetermined distances therebetween and manufacturing microneedle arrays 1M as fine hollow protruding articles 1.

As described above, the manufacturing method of the first embodiment for manufacturing a microneedle array 1M having through holes 3h by using the manufacturing device 100B of the first embodiment involves: a protrusion precursor forming step for forming protrusion precursors 3b each having a through hole 3h; and a protrusion elongating step for forming protrusions 3. Thus, it is possible to manufacture high-quality microneedle arrays 1M with through holes 3h having high precision in the height of the protrusions 3 on the microneedle array 1M and the size of the through hole 3h in each protrusion 3. Further, with the manufacturing method of the first embodiment, microneedle arrays 1M having through holes 3h can be manufactured through simple steps, and cost reduction can be achieved. Further, with the manufacturing method of the first embodiment, microneedle arrays 1M having through holes 3h can be mass-produced stably, continuously, and efficiently. Note that, in the present Specification, a "microneedle array having a through hole" refers to a "microneedle array having a microneedle, which is a protrusion having a through hole".

Further, according to the manufacturing method of the first embodiment, the heat quantity applied from the projecting mold part 11 to the base sheet 2A in the protrusion elongating step is greater than the heat quantity applied from the projecting mold part 11 to the base sheet 2A in the protrusion precursor forming step. Thus, it is possible to manufacture high-quality microneedle arrays 1M with through holes 3h having an even higher precision in the height of the protrusion 3 and the size of the through hole 3h in each protrusion 3. More specifically, because the heat quantity applied to the base sheet 2A is small in the protrusion precursor forming step, the condition makes it easier to open the tip end portion than to elongate the base sheet 2A. Thus, the size of the tip-end through hole 3h is easier to control. On the other hand, in the protrusion elongating step performed subsequently, the heat quantity applied to the base sheet 2A is large, and thus, the condition makes it easy to elongate the protrusion precursor 3b that has been opened. Thus, the height of the protrusion 3 can be designed easily while maintaining a favorable shape, while preventing the shape of the through hole 3h from getting damaged.

Further, according to the manufacturing method of the first embodiment, the frequency and amplitude conditions (i.e., the conditions of the heating means) of the ultrasonic vibration by the ultrasonic vibration device of the projecting mold part 11 in the protrusion precursor forming step are the same as the frequency and amplitude conditions (i.e., the conditions of the heating means) of the ultrasonic vibration by the ultrasonic vibration device of the projecting mold part 11 in the protrusion elongating step. However, the speed further for inserting the projecting mold part 11 into the base sheet 2A in the protrusion elongating step is slower than the speed for inserting the projecting mold part 11 into the base sheet 2A in the protrusion precursor forming step, and the heat quantity applied from the projecting mold part 11 to the base sheet 2A in the protrusion elongating step is greater than the heat quantity applied from the projecting mold part 11 to the base sheet 2A in the protrusion precursor forming step. By changing the speed for inserting the projecting mold part 11 into the base sheet 2A in this way, the heat quantity applied from the projecting mold part 11 to the base sheet 2A in the protrusion elongating step is made greater than the heat quantity applied from the projecting mold part 11 to the base sheet 2A in the protrusion precursor forming step. Thus, it is possible to manufacture microneedle arrays 1M having through holes 3h with higher quality by more easily controlling the precision in the height of the protrusions 3 on the microneedle array 1M and the size of the through hole 3h in each protrusion 3. Further, the manufacturing method of the first embodiment is preferable because the total heat quantity applied to the base sheet 2A can be controlled by speed control, and the protrusion precursor can be stretched easily to a favorable shape.

Further, according to the manufacturing method of the first embodiment, as regards the insertion speed for inserting the projecting mold part 11 into the base sheet 2A, the insertion speed is made continuously slower from the protrusion precursor forming step to the protrusion elongating step by employing the box-motion-type projecting mold parts 11. In this way, the heat quantity applied from the projecting mold part 11 to the base sheet 2A in the protrusion precursor forming step and the heat quantity applied from the projecting mold part 11 to the base sheet 2A in the protrusion elongating step continuously change from the protrusion precursor forming step to the protrusion elongating step. Thus, it is more easy to control the precision in the height of the protrusions 3 on the microneedle array 1M and the size of the through hole 3h in each protrusion 3.

Further, according to the manufacturing method of the first embodiment, because an ultrasonic vibration device is employed as the heating means (not illustrated) of the projecting mold part 11, the cold air blowing device 21 does not necessarily have to be provided, and cooling can be achieved by simply turning off the vibration of the ultrasonic vibration device. From this viewpoint, using ultrasonic vibration as the heating means can simplify the device, and microneedle arrays 1M having through holes 3h can be manufacture at high speed. Further, heat is less likely to be transmitted to sections of the base sheet 2A that are not in contact with the projecting mold part 11 and cooling is performed efficiently by stopping the application of ultrasonic vibration; thus, deformation is less likely to occur in sections other than the section being molded, and microneedle arrays 1M with high precision can be manufactured.

Further, as described above, in the protrusion forming section 10 of the manufacturing device 100B of the first embodiment, the control means (not illustrated) controls the operations of the projecting mold parts 11, the heating condition of the heating means (not illustrated) of the projecting mold part 11, the cooling temperature of the cold air blowing device 21, and the cooling time. Thus, by controlling, for example, the insertion height of the projecting mold part 11 in the protrusion elongating step with the control means (not illustrated), the insertion amount of the projecting mold part 11 into the base sheet 2A can be changed easily, and the protrusion height H1 of the microneedle array 1M to be manufactured can be controlled. Further, by controlling at least one of a condition of the heating means (not illustrated) of the projecting mold part 11, the softening time of the contact section TP of the base sheet 2A, the insertion speed of the projecting mold part 11 into the base sheet 2A, and the shape of the projecting mold part 11, the thickness T1, etc., of the protrusion 3 constituting the microneedle array 1M can be controlled freely, and the shape of the microneedle array 1M having through holes 3h can be controlled freely. Stated differently, the shape of the microneedle array 1M can be controlled freely by controlling at least one condition selected from the insertion height of the projecting mold part 11 in the protrusion elongating step, the heating condition, the softening time of the contact section TP of the base sheet 2A, the insertion speed of the projecting mold part 11 into the base sheet 2A, and a cooling condition in the cooling step.

Further, as described above, in the first embodiment, as illustrated in FIG. 14, the pair of supports 12, 12—which is arranged on the other surface 2U side (upper surface side) of the base sheet 2A—is used to support the base sheet 2A's respective lateral sides along the transporting direction (Y direction), and the projecting mold part 11 is brought into contact from the one surface 2D (lower surface)—which is on the opposite side from where the supports 12 are arranged—in the base sheet 2A's central region which is in a free floating state between the pair of supports 12, 12, to thereby soften the contact section TP and form a protrusion 3. Because there is no need to provide a depression, etc., into which the projecting mold part 11 is fitted to form the protrusion 3, it is possible to suppress an increase in cost, and to precisely and efficiently form the protrusion 3 of the microneedle array 1M to be manufactured.

Next, the invention (second invention) will be described according to a second embodiment with reference to FIG. 17. Note that the following description mainly focuses on features that are different from those of the foregoing first embodiment.

In the manufacturing device 100B of the first embodiment used in the foregoing first embodiment, the heating means (not illustrated) of the projecting mold part 11 is an ultrasonic vibration device. In the manufacturing device 100B of the second embodiment used in the second embodiment, a heating heater device is used instead.

Figures 17A, 17B, 17C, 17D, 17E:
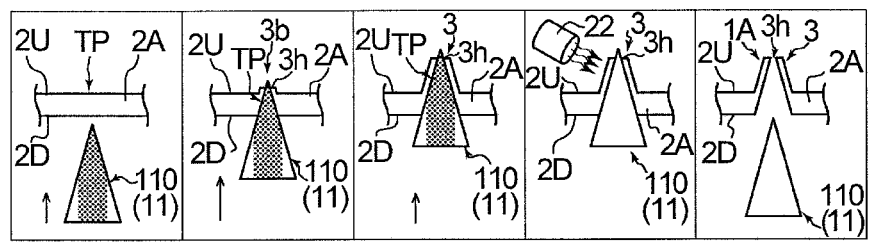
FIGS. 17(a) to 17(e) are diagrams illustrating steps for manufacturing a fine hollow protruding article having a through hole by employing a manufacturing device of a second embodiment.

In cases where the heating means (not illustrated) of the projecting mold part 11 is a heating heater device as in the manufacturing device 100B of the second embodiment, the heating heater device heats the projecting mold part 11 at each of the contact sections TP, and the contact sections TP are softened by generating heat at the contact sections TP, as illustrated in FIG. 17(a). Then, in the protrusion precursor forming step of the second embodiment, as illustrated in FIG. 17(b), while softening the contact section TP, the projecting mold part 11 is raised from the one surface 2D (lower surface) of the base sheet 2A toward the other surface 2U (upper surface) and the tip end portion of each projecting mold 110 is inserted into the base sheet 2A, to form a hollow protrusion precursor 3b that protrudes from the other surface 2U (upper surface) of the base sheet 2A and that has a penetrating through hole 3h.

In the protrusion precursor forming step of the second embodiment, from the viewpoint of forming the protrusion precursor 3b, the heating temperature of the base sheet 2A by the projecting mold part 11 is preferably equal to or higher than the glass transition temperature (Tg) of the base sheet 2A being used to below the melting temperature thereof, and more preferably, equal to or higher than the softening temperature of the resin to below the melting temperature thereof. More specifically, the heating temperature is preferably 30° C. or higher, more preferably 40° C. or higher, and preferably 300° C. or lower, more preferably 250° C. or lower, and more specifically, preferably from 30 to 300° C., more preferably from 40 to 250° C. When a heating heater device is used as in the second embodiment, the heating temperature of the projecting mold part 11 simply needs to be adjusted within the aforementioned range in the protrusion precursor forming step. Also in cases where the base sheet 2A is heated by using an ultrasonic vibration device as in the first embodiment, the heating temperature is employed as the temperature range of a section of the base sheet 2A that comes into contact with the projecting mold 110.

Note that the "glass transition temperature (Tg) of the base sheet" refers to the glass transition temperature (Tg) of the resin constituting the base sheet. In cases where there are a plurality of types of constituent resins and the plurality of glass transition temperatures (Tg) are different from each other, the heating temperature of the base sheet by the heating means is preferably at least equal to or higher than the lowest glass transition temperature (Tg) among the plurality of glass transition temperatures (Tg), and more preferably equal to or higher than the highest glass transition temperature (Tg) among the plurality of glass transition temperatures (Tg).

The same applies to the "softening temperature of the base sheet", as with the glass transition temperature (Tg). In cases where there are a plurality of types of constituent resins in the base sheet and the plurality of softening temperatures are different from each other, the heating temperature of the base sheet by the heating means is preferably at least equal to or higher than the lowest softening temperature among the plurality of softening temperatures, and more preferably equal to or higher than the highest softening temperature among the plurality of softening temperatures.

In cases where the base sheet includes two or more types of resins having different melting points, the heating temperature of the base sheet by the heating means is preferably below the lowest melting point among the plurality of melting points.

{Method for Measuring Glass Transition Point (Tg)}

The glass transition temperature is determined by measuring the heat quantity by using a DSC measurement device. More specifically, the measurement device used is a differential scanning calorimeter (Diamond DSC) from Perkin Elmer. A 10 mg test piece is sampled from the base sheet. As for the measurement conditions, the temperature is kept constant at 20° C. for 5 minutes, and then the temperature is raised from 20° C. to 320° C. at a rate of 5° C./minute, to obtain a DSC curve wherein the horizontal axis indicates temperature and the vertical axis indicates heat quantity. The glass transition temperature Tg is determined from the DSC curve.

Next, in the protrusion elongating step of the second embodiment, as illustrated in FIG. 17(c), at each contact section TP, the projecting mold part 11 is heated with the heating heater device to the same temperature as in the protrusion precursor forming step, and, while softening the contact section TP by generating heat in the contact section TP, the tip end portion of the projecting mold part 11 is further inserted into the base sheet 2A by further raising the projecting mold part 11 from the one surface 2D (lower surface) of the base sheet 2A toward the other surface 2U (upper surface), to form a protrusion 3 that further protrudes from the other surface 2U (upper surface) of the base sheet 2A and that has a through hole 3h.

It should be noted that, in the protrusion elongating step of the second embodiment, the insertion speed for inserting the projecting mold part 11 into the base sheet 2A is slower than the insertion speed for inserting the projecting mold part 11 into the base sheet 2A in the protrusion precursor forming step.

In the manufacturing device 100B of the second embodiment, the heating means (not illustrated) of the projecting mold part 11 is a heating heater as described above, and the heater temperature of the projecting mold part 11 in the protrusion elongating section 10B is the same temperature as the heater temperature of the projecting mold part 11 in the protrusion precursor forming section 10A, thus not satisfying the aforementioned condition (d). However, in the second embodiment, as regards the insertion speed for inserting the projecting mold part 11 into the base sheet 2A, the insertion speed in the protrusion elongating step is slower than the insertion speed in the protrusion precursor forming step, thus satisfying the aforementioned condition (a). Thus, the heat quantity applied from the projecting mold part 11 to the base sheet 2A in the protrusion elongating step is greater than the heat quantity applied from the projecting mold part 11 to the base sheet 2A in the protrusion precursor forming step.

Next, in the cooling step of the second embodiment, as in the cooling step of the first embodiment, as illustrated in FIG. 17(d), the protrusions 3 are cooled by blowing cold air from the air vent 22 arranged on the other surface 2U side (upper surface side) of the base sheet 2A inside the tunnel, with the projecting molds 110 of the projecting mold part 11 still inserted in the interior of the respective protrusions 3. Note that, during cooling, heating of the projecting mold part 11 with the heating heater device may be continued or stopped.

In cases where the heating means (not illustrated) of the projecting mold part 11 is a heating heater device as in the manufacturing device 100B of the second embodiment, cooling may be performed naturally in the cooling section 20 provided downstream of the protrusion forming section 10. It is, however, preferable to provide a cold air blowing device 21 and perform active cooling.

Next, in the release step of the second embodiment, as in the release step of the first embodiment, as illustrated in FIG. 17(e), the projecting mold part 11 is lowered from the one surface 2D (lower surface) of the base sheet 2A, and the projecting molds 110 of the projecting mold part 11 are withdrawn from the state where the projecting molds 110 of the projecting mold part 11 are inserted in the interior of the respective protrusions 3, to form a precursor 1A of a continuous fine hollow protruding article, which ultimately becomes a microneedle array 1M wherein protrusions 3 each having a through hole 3h and having a hollow interior are arranged in an array.

Next, in the second embodiment, as in the first embodiment, cutting is performed with the cutter blade of the cutter part 41, to continuously manufacture pieces of microneedle arrays 1M wherein protrusions 3 each having a through hole 3h are arranged in an array, and the microneedle arrays 1M are re-arranged in the re-pitching section 50.

As described above, according to the manufacturing method of the second embodiment, the heating conditions by the heating heater device (i.e., the conditions of the heating means) of the projecting mold part 11 in the protrusion precursor forming step are the same as the heating conditions by the heating heater device (i.e., the conditions of the heating means) of the projecting mold part 11 in the protrusion elongating step. However, the speed for further inserting the projecting mold part 11 into the base sheet 2A in the protrusion elongating step is slower than the speed for inserting the projecting mold part 11 into the base sheet 2A in the protrusion precursor forming step, and the heat quantity applied from the projecting mold part 11 to the base sheet 2A in the protrusion elongating step is greater than the heat quantity applied from the projecting mold part 11 to the base sheet 2A in the protrusion precursor forming step. By changing the speed for inserting the projecting mold part 11 into the base sheet 2A in this way, the heat quantity applied from the projecting mold part 11 to the base sheet 2A in the protrusion elongating step is made greater than the heat quantity applied from the projecting mold part 11 to the base sheet 2A in the protrusion precursor forming step. Thus, it is possible to manufacture through-hole-including microneedle arrays 1M with higher quality by more easily controlling the precision in the height of the protrusions 3 on the microneedle array 1M and the size of the through hole 3h in each protrusion 3.

Further, as described above, in the second embodiment, as illustrated in FIG. 17(a), the projecting mold part 11 is heated by the heating heater device only at the contact sections TP of the base sheet 2A in contact with the projecting mold part 11 and thereby the contact sections TP are softened. Thus, microneedle arrays 1M having through holes 3h can be manufactured continuously and efficiently while saving energy. In contrast, in cases where the entire resin needs to be heated to the same temperature as the projecting mold part, not only is energy efficiency poor, but also various other problems may arise—such as pitch discrepancies between protrusions, distortion of the sheet, and difficulty in continuously transporting the sheet—due to the entire sheet getting soft. In the second embodiment, on the other hand, heat due to heating by the projecting mold part 11 is transmitted efficiently to the contact sections TP, and peripheral sections thereof are in an environment where heating can be left only to natural progression; thus, pitch discrepancies among the protrusions 3, as well as distortion of the base sheet 2A, are less likely to occur, and it is easy to transport the base sheet 2A continuously.

The invention (third invention) is described below according to preferred embodiments thereof with reference to the drawings.

Figure 19:
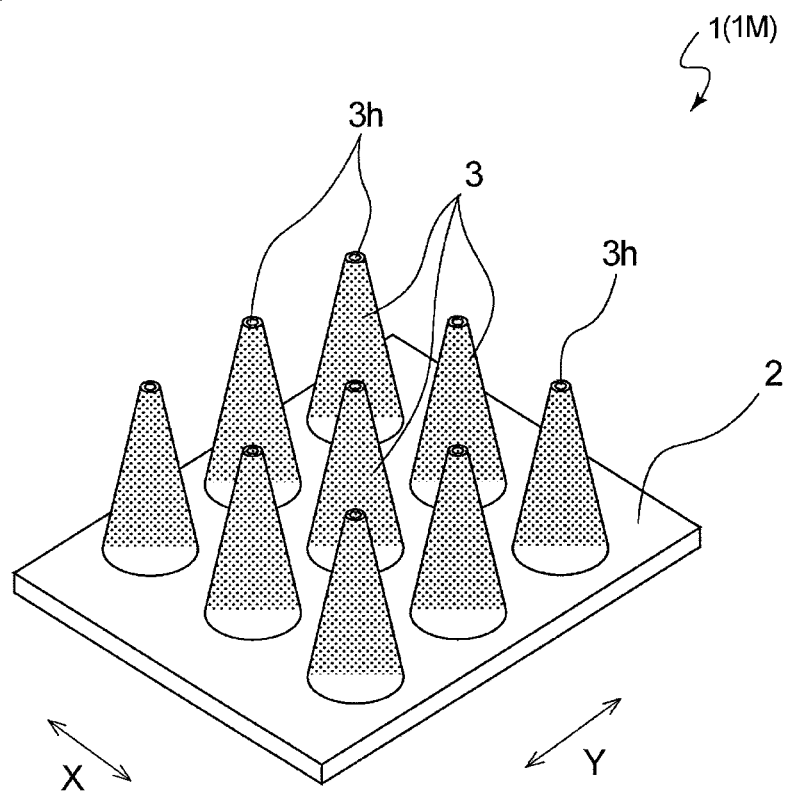
FIG. 19 is a schematic perspective view of an example of a fine hollow protruding article in which protrusions each having a through hole are arranged in an array, the fine hollow protruding article being manufactured by a method for manufacturing a fine hollow protruding article according to the invention (third invention).

A manufacturing method of the invention (third invention) is a method for manufacturing a fine hollow protruding article having through holes. FIG. 19 illustrates a perspective view of a microneedle array 1M, which is a fine hollow protruding article of an embodiment, manufactured according to a method for manufacturing a fine hollow protruding article 1 of a first embodiment. The microneedle array 1M of the present embodiment includes: a sheet-like basal portion 2; and a plurality of protrusions 3. The number of protrusions 3, the arrangement of the protrusions 3, and the shape of the protrusion 3 are not particularly limited, but preferably in the microneedle array 1M of the present embodiment, nine truncated circular-conic protrusions 3 are provided in an array (matrix) on the upper surface of the sheet-like basal portion 2. The nine protrusions 3 arranged in an array (matrix) are arranged in three rows along the Y direction, which is the direction in which the later-described base sheet 2A is transported (i.e., the longitudinal direction of the base sheet 2A), and in three columns along the X direction, which is the direction orthogonal to the transporting direction and which is the lateral direction of the base sheet 2A being transported. Note that FIG. 20 is a perspective view of the microneedle array 1M, focusing on a single protrusion 3 among the protrusions 3 arranged in an array (matrix) in the microneedle array 1M, and FIG. 21 is a cross-sectional view taken along line III-III illustrated in FIG. 20.

Figure 20:
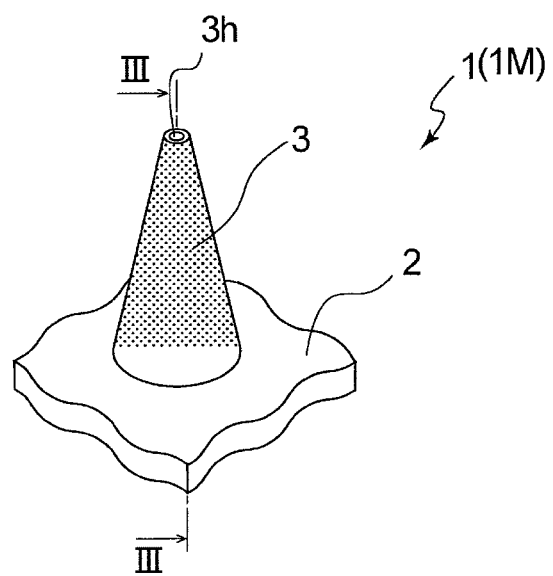
FIG. 20 is a perspective view of the fine hollow protruding article illustrated in FIG. 19, focusing on a single protrusion.
Figure 21:
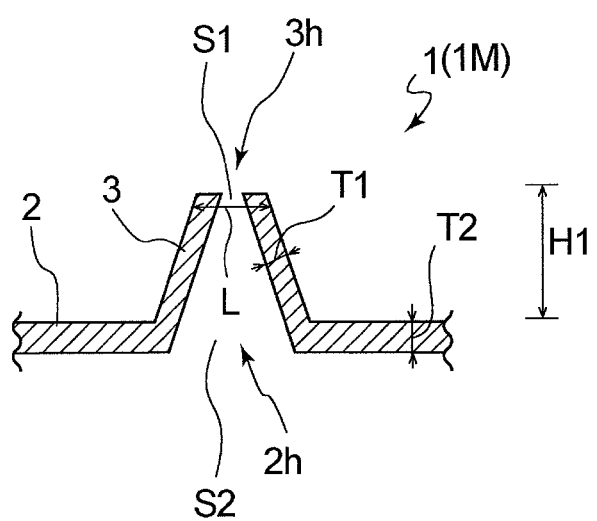
FIG. 21 is a cross-sectional view taken along line illustrated in FIG. 20.

As illustrated in FIG. 20, the microneedle array 1M has through holes 3h. Preferably, in the present embodiment, as illustrated in FIG. 21, in the microneedle array 1M, a space extending from the basal portion 2 to each through hole 3h is formed in the interior of each protrusion 3, and a through hole 3h is formed in the tip end of each protrusion 3. In the microneedle array 1M, the interior space of each protrusion 3 is formed in a shape corresponding to the outer shape of the protrusion 3, and in the present embodiment, is formed in a truncated circular-conic shape corresponding to the outer shape of the truncated circular-conic protrusion 3. It should be noted that, although the protrusion 3 in the present embodiment is truncated circular-conic, the protrusion may have a shape other than a truncated circular-conic shape, such as the shape of a circular cylinder, a prism, or a truncated pyramid.

In order for the tip end of each protrusion 3 to reach, for example, the stratum corneum, which is the outermost layer, or the dermis, which is a deeper layer, the protrusion height H1 of each protrusion 3 in the microneedle array 1M is preferably 0.01 mm or greater, more preferably 0.02 mm or greater, and preferably 10 mm or less, more preferably 5 mm or less, and more specifically, preferably from 0.01 to 10 mm, more preferably from 0.02 to 5 mm.

The average thickness T1 of each protrusion 3 is preferably 0.005 mm or greater, more preferably 0.01 mm or greater, and preferably 1.0 mm or less, more preferably 0.5 mm or less, and more specifically, preferably from 0.005 to 1.0 mm, more preferably from 0.01 to 0.5 mm.

The thickness T2 of the basal portion 2 is preferably 0.01 mm or greater, more preferably 0.02 mm or greater, and preferably 1.0 mm or less, more preferably 0.7 mm or less, and more specifically, preferably from 0.01 to 1.0 mm, more preferably from 0.02 to 0.7 mm.

The tip end size L, in diameter, of each protrusion 3 of the microneedle array 1M is preferably 1 µm or greater, more preferably 5 µm or greater, and preferably 500 µm or less, more preferably 300 µm or less, and more specifically, preferably from 1 to 500 µm, more preferably from 5 to 300 µm. The tip end diameter L of the fine hollow protruding article 1 is the length at the widest position at the tip end of each protrusion 3. By setting the tip end diameter within the aforementioned range, the microneedle array 1M hardly causes any pain when it is inserted into the skin.

As illustrated in FIG. 21, the fine hollow protruding article 1 has: a through hole 3h located at the tip end section of each protrusion 3; and a basal-side through hole 2h located at the lower surface of the basal portion 2 corresponding to each protrusion 3. In the microneedle array 1M of the present embodiment, the through hole 3h and the basal-side through hole 2h are formed concentrically.

The opening area S1 of the through hole 3h is preferably 0.7 µm$^2$ or greater, more preferably 20 µm$^2$ or greater, and preferably 200000 µm$^2$ or less, more preferably 70000 µm$^2$ or less, and more specifically, preferably from 0.7 to 200000 µm$^2$, more preferably from 20 to 70000 µm$^2$.

The opening area S2 of the basal-side through hole 2h is preferably 0.007 mm$^2$ or greater, more preferably 0.03 mm$^2$ or greater, and preferably 20 mm$^2$ or less, more preferably 7 mm$^2$ or less, and more specifically, preferably from 0.007 to 20 mm$^2$, more preferably from 0.03 to 7 mm$^2$.

The nine protrusions 3 arranged in an array (matrix) on the upper surface of the sheet-like basal portion 2 are preferably arranged such that the center-to-center distance in the longitudinal direction (Y direction) is uniform and the center-to-center distance in the lateral direction (X direction) is uniform, and preferably, the center-to-center distance in the longitudinal direction (Y direction) is the same as the center-to-center distance in the lateral direction (X direction). Preferably, the center-to-center distance in the longitudinal direction (Y direction) between the protrusions 3 is preferably 0.01 mm or greater, more preferably 0.05 mm or greater, and preferably 10 mm or less, more preferably 5 mm or less, and more specifically, preferably from 0.01 to 10 mm, more preferably from 0.05 to 5 mm. The center-to-center distance in the lateral direction (X direction) between the protrusions 3 is preferably 0.01 mm or greater, more preferably 0.05 mm or greater, and preferably 10 mm or less, more preferably 5 mm or less, and more specifically, preferably from 0.01 to 10 mm, more preferably from 0.05 to 5 mm.

Figure 22:
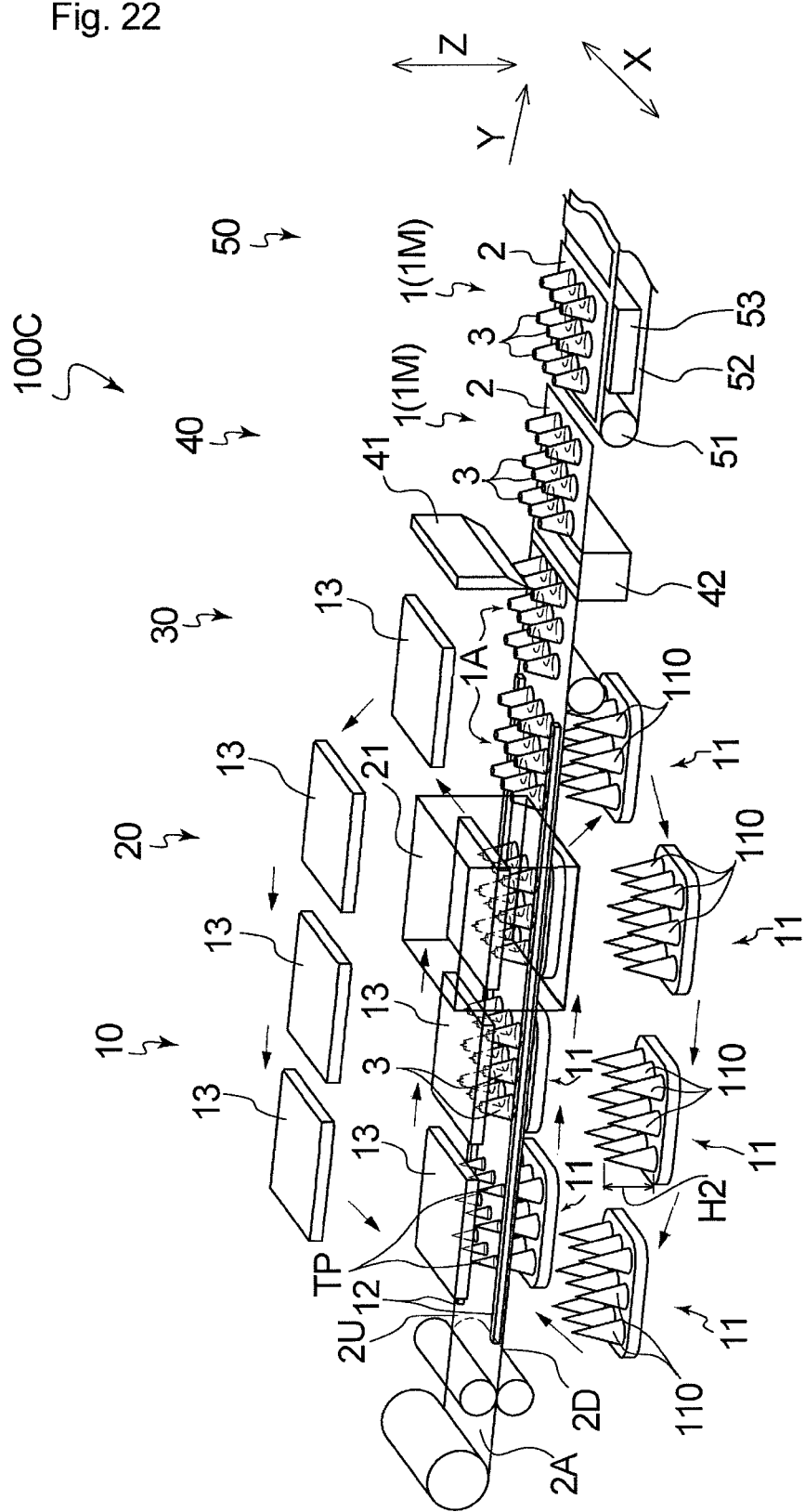
FIG. 22 is a diagram illustrating an overall configuration of a first embodiment of a manufacturing device for manufacturing the fine hollow protruding article illustrated in FIG. 19.
Figure 23:
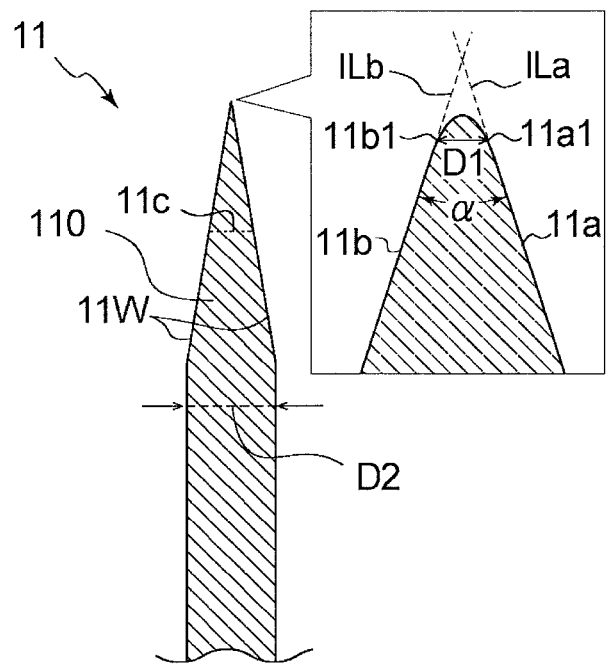
FIG. 23 is an explanatory diagram illustrating a method for measuring the tip end diameter and the tip end angle of a projecting mold of a projecting mold part.

Next, a method for manufacturing a fine hollow protruding article of the invention (third invention) is described with reference to FIGS. 22 to 24, taking, as an example, a method for manufacturing the aforementioned microneedle array 1M serving as a fine hollow protruding article 1. FIG. 22 illustrates an overall configuration of a manufacturing device 100C according to the first embodiment used for implementing the manufacturing method of the first embodiment. It should be noted that, each protrusion 3 of the microneedle array 1M is actually very small as described above, but for the sake of explanation, each protrusion 3 of the microneedle array 1M is illustrated very large in FIG. 22.

The manufacturing device 100C of the first embodiment illustrated in FIG. 22 includes, from the upstream side toward the downstream side: a protrusion forming section 10 for forming protrusions 3 in a base sheet 2A; a cooling section 20; a release section 30 where the later-described projecting mold part 11 is withdrawn; a cutting section 40 where each microneedle array 1M is cut; and a re-pitching section 50 where the interval between the microneedle arrays 1M is adjusted.

In the following description, the direction in which the base sheet 2A is transported (the longitudinal direction of the base sheet 2A) is referred to as the Y direction, the direction orthogonal to the transporting direction, which is the lateral direction of the base sheet 2A being transported, is referred to as the X direction, and the thickness direction of the base sheet 2A being transported is referred to as the Z direction.

As illustrated in FIG. 22, the protrusion forming section 10 includes projecting mold parts 11 each including a heating means (not illustrated). The projecting mold part 11 includes projecting molds 110 corresponding to the number and arrangement of the protrusions 3 on the microneedle array 1M to be manufactured and substantially to the outer shape of each protrusion 3. In the manufacturing device 100C of the first embodiment, nine circular-conic projecting molds 110 are provided corresponding to the nine truncated circular-conic protrusions 3. It should be noted that, in the manufacturing device used for the method for manufacturing a fine hollow protruding article of the present invention (third invention), no other heating means is provided except for the heating means (not illustrated) of each projecting mold part 11. It should be noted that, in this Specification, "no other heating means is provided except for the heating means of the projecting mold part 11" not only refers to cases where other heating means are completely eliminated, but also refers to cases where a means for heating to a temperature below the softening temperature of the base sheet 2A, or to a temperature below the glass transition temperature, is provided. Note, however, that it is preferable to completely eliminate all other heating means.

In the manufacturing device 100C of the first embodiment, the heating means (not illustrated) of the projecting mold part 11 is an ultrasonic vibration device. In the first embodiment, first, a continuous base sheet 2A is paid out from a material roll of a base sheet 2A including a thermoplastic resin, and is transported in the Y direction. Then, the projecting mold part 11 is brought into contact from the one surface 2D side of the continuous base sheet 2A being transported in the Y direction, and, while softening, with heat, a contact section TP in the base sheet 2A where the projecting mold part contacts the base sheet, the projecting mold part 11 is inserted into the base sheet 2A toward the other surface 2U side of the base sheet 2A, to form a protrusion 3 that protrudes from the other surface 2U side of the base sheet 2A (protrusion forming step). The protrusion forming step employs a receiving member 13 on the other surface 2U side of the base sheet 2A, the receiving member 13 being arranged at a distance from the other surface 2U of the base sheet 2A. In the protrusion forming step, a through hole 3h is formed in the protrusion 3 by the projecting mold part 11 coming into contact with the receiving member 13. Preferably, in the protrusion forming step of the first embodiment, a portion of the base sheet 2A stretched by the projecting mold part 11 comes into contact with the receiving member 13, and the base sheet 2A is sandwiched between the projecting mold part 11 and the receiving member 13. The projecting mold part 11 is pressed into the base sheet 2A until it penetrates the base sheet 2A and the projecting mold part 11 protrudes from the other surface 2U side of the base sheet 2A, to form a protrusion 3 having a through hole 3h that penetrates the base sheet 2A on the other surface 2U side. Preferably, in the manufacturing device 100C of the first embodiment, nine circular-conic projecting molds 110 with a sharp tip end are arranged in the projecting mold part 11 so that their tip ends face upward, and the projecting mold part 11 is movable at least vertically in the thickness direction (Z direction). More preferably, in the manufacturing device 100C of the first embodiment, the projecting mold part 11 can move vertically in the thickness direction (Z direction) by an electric actuator (not illustrated), and can travel together with the base sheet 2A in the transporting direction (Y direction). The operation of the projecting mold part 11 is controlled by a control means (not illustrated) provided to the manufacturing device 100C of the first embodiment. As described above, the manufacturing device 100C of the first embodiment is a device including projecting mold parts 11 of the so-called "box-motion-type" which follow an endless track. Heating of the heating means (not illustrated) of the projecting mold part 11 is also controlled by the control means (not illustrated) provided to the manufacturing device 100C of the first embodiment.

The base sheet 2A is a sheet that constitutes the basal portion 2 of the microneedle array 1M being manufactured, and includes a thermoplastic resin. Examples of the thermoplastic resin include poly-fatty acid esters, polycarbonate, polypropylene, polyethylene, polyester, polyamide, polyamide imide, polyether ether ketone, polyetherimide, polystyrene, polyethylene terephthalate, polyvinyl chloride, nylon resin, acrylic resin, and combinations thereof. From the viewpoint of biodegradability, poly-fatty acid esters are preferably used. Concrete examples of poly-fatty acid esters include polylactic acid, polyglycolic acid, and combinations thereof. Note that the base sheet 2A may be formed of a mixture including, for example, hyaluronic acid, collagen, starch, cellulose, etc., in addition to thermoplastic resin. The thickness of the base sheet 2A is substantially the same as the thickness T2 of the basal portion 2 of the microneedle array 1M being manufactured.

The outer shape of the projecting mold 110 of the projecting mold part 11 has a sharper shape than the outer shape of the protrusion 3 of the microneedle array 1M. The height H2 (cf. FIG. 22) of the projecting mold 110 of the projecting mold part 11 is formed higher than the height H1 of the microneedle array 1M being manufactured, and is preferably 0.01 mm or greater, more preferably 0.02 mm or greater, and preferably 30 mm or less, more preferably 20 mm or less, and more specifically, preferably from 0.01 to 30 mm, more preferably from 0.02 to 20 mm. The tip end diameter D1 (cf. FIG. 23) of the projecting mold 110 of the projecting mold part 11 is preferably 0.001 mm or greater, more preferably 0.005 mm or greater, and preferably 1 mm or less, more preferably 0.5 mm or less, and more specifically, preferably from 0.001 to 1 mm, more preferably from 0.005 to 0.5 mm. The tip end diameter D1 of the projecting mold 110 of the projecting mold part 11 is measured as follows.

The base diameter D2 (cf. FIG. 23) of the projecting mold 110 of the projecting mold part 11 is preferably 0.1 mm or greater, more preferably 0.2 mm or greater, and preferably 5 mm or less, more preferably 3 mm or less, and more specifically, preferably from 0.1 to 5 mm, more preferably from 0.2 to 3 mm.

From the viewpoint of easily achieving sufficient strength, the tip end angle α (cf. FIG. 23) of the projecting mold 110 of the projecting mold part 11 is preferably 1 degree or greater, more preferably 5 degrees or greater. From the viewpoint of obtaining a protrusion 3 having an appropriate angle, the tip end angle α is preferably 60 degrees or less, more preferably 45 degrees or less, and more specifically, preferably from 1 to 60 degrees, more preferably from 5 to 45 degrees. The tip end angle α of the projecting mold 110 of the projecting mold part 11 is measured as follows.

{Measurement of Tip End Diameter of Projecting Mold 110 of Projecting Mold Part 11}

The tip end portion of the projecting mold 110 of the projecting mold part 11 is observed in an enlarged state under a predetermined magnification using a scanning electron microscope (SEM) or a microscope. Next, as illustrated in FIG. 23, an imaginary straight line ILa is extended along the straight-line portion of one lateral side 11a of the two lateral sides 11a, 11b. Also, an imaginary straight line ILb is extended along the straight-line portion of the other lateral side 11b. The point where the lateral side 11a separates from the imaginary straight line ILa on the tip end side is defined as a first tip end point 11a1, and the point where the other lateral side 11b separates from the imaginary straight line ILb is defined as a second tip end point 11b1. The length D1 of a straight line that connects the first tip end point 11a1 and the second tip end point 11b1 defined as above is measured using a scanning electron microscope (SEM) or a microscope, and the measured length of the straight line is defined as the tip end diameter of the projecting mold 110.

{Measurement of Tip End Angle α of Projecting Mold 110 of Projecting Mold Part 11}

The tip end portion of the projecting mold 110 of the projecting mold part 11 is observed in an enlarged state under a predetermined magnification using a scanning electron microscope (SEM) or a microscope. Next, as illustrated in FIG. 23, an imaginary straight line ILa is extended along the straight-line portion of one lateral side 11a of the two lateral sides 11a, 11b. Also, an imaginary straight line ILb is extended along the straight-line portion of the other lateral side 11b. The angle formed between the imaginary straight line ILa and the imaginary straight line ILb is measured using a scanning electron microscope (SEM) or a microscope, and the measured angle is defined as the tip end angle α of the projecting mold 110 of the projecting mold part 11.

The projecting mold part 11 is formed of a high-strength material that is hard to bend/break. Examples of materials for the projecting mold part 11 include metals, such as steel, stainless steel, aluminum, aluminum alloy, nickel, nickel alloy, cobalt, cobalt alloy, copper, copper alloy, beryllium copper, and beryllium copper alloy, and ceramics.

The receiving member 13 used in the method for manufacturing a fine hollow protruding article according to the present invention (third invention) is arranged on the other surface 2U side of the base sheet 2A at a distance from the base sheet 2A. The shape of the receiving member 13 is not particularly limited, but in the manufacturing device 100C of the first embodiment, the receiving member is plate-shaped. The length, in the Y direction, of the plate-shaped receiving member 13 is substantially the same as the length of the projecting mold part 11 in the Y direction. The length, in the X direction, of the plate-shaped receiving member is substantially the same as the length of the projecting mold part 11 in the X direction. In the manufacturing device 100C of the first embodiment, as illustrated in FIG. 22, such plate-shaped receiving members 13 follow an endless track according to a box motion so as to operate corresponding to the operation of the box-motion-type projecting mold parts 11 while sandwiching the base sheet 2A being transported in the Y direction. Each of the box-motion-type receiving members 13 is arranged above the other surface 2U of the base sheet 2A in the thickness direction (Z direction) at a distance therefrom, and can travel together with the base sheet 2A in the transporting direction (Y direction). The movement speed of the receiving member 13 in the transporting direction (Y direction) corresponds to the movement speed of the projecting mold part 11 in the transporting direction (Y direction), and is controlled by the control means (not illustrated) provided to the manufacturing device 100C of the first embodiment.

The material for the receiving member 13 only needs to have a hardness that is harder than the hardness of the base sheet 2A when the projecting mold part 11 is inserted into the base sheet 2A and contacts the receiving member 13, and may be formed of an elastic material such as rubber, a synthetic resin, or the same material as the material of the projecting mold part 11. Note that it is preferable that, from the viewpoint of ease of processing, the hardness of the material of the receiving member 13 is harder than the hardness of the base sheet 2A that has been softened by being heated to a temperature equal to or above the softening point of the base sheet 2A.

The distance between the receiving member 13 and the base sheet 2A matches the protrusion height H1 of the protrusion 3 of the microneedle array 1M being manufactured, and can be changed by the control means (not illustrated) provided to the manufacturing device 100C of the first embodiment depending on the protrusion height H1 of the protrusion 3 being manufactured.

Figure 24:
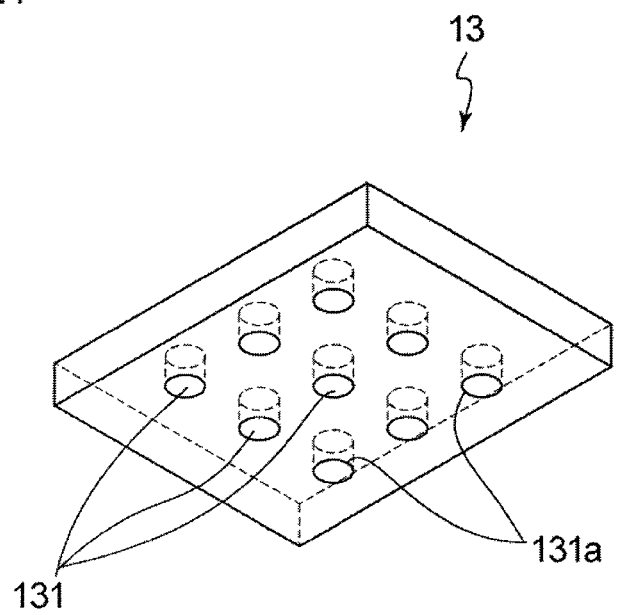
FIG. 24 is a perspective view, as viewed from the base sheet side, of a receiving member provided to the manufacturing device illustrated in FIG. 22.

As illustrated in FIG. 24, in the manufacturing device 100C of the first embodiment, the receiving member 13 has depressions 131, and preferably has depressions 131 at sections that come into contact with the respective projecting mold parts 11. The shape of the opening peripheral edge 131a of each depression 131 matches a shape of an outer periphery 11c of the peripheral wall 11W of the projecting mold part 11 at a position where the peripheral wall 11W comes into contact with the receiving member 13 (cf. FIG. 23). In the manufacturing device 100C of the first embodiment, there are nine depressions 131 corresponding to the nine projecting molds 110. Herein, the shape of the opening peripheral edge 131a of the depression 131 refers to the shape of the contour of the depression 131 when the depression 131 formed in the surface of the receiving member 13 on the side of the base sheet 2A is viewed as a planar view from the base sheet 2A side. The shape of the outer periphery 11c of the projecting mold part 11 refers to the shape of the contour of the projecting mold 110 in a cross-sectional view of the projecting mold 110 at a position where the peripheral wall 11W of the projecting mold 110 of the projecting mold part 11 comes into contact with the receiving member 13. In the manufacturing device 100C of the first embodiment, each projecting mold 110 is circular-conic, and thus the shape of the outer periphery 11c is circular, and the shape of the opening peripheral edge 131a of each depression 131 is also circular. Note that, if the shape of the projecting mold 110 is a pyramid, the shape of the outer periphery 11c is rectangular, and the shape of the opening peripheral edge 131a of each depression 131 is also rectangular.

In each depression 131 of the receiving member 13, only the shape of the opening peripheral edge 131a needs to match the shape of the outer periphery 11c of the projecting mold part 11, and the shape of the receiving member 13 more inward of the opening peripheral edge 131a is not particularly limited; in the manufacturing device 100C of the first embodiment, the depression 131 has a circular-cylindrical shape, as illustrated in FIG. 24.

In the manufacturing device 100C of the first embodiment, as illustrated in FIG. 22, the protrusion forming section 10 includes a support 12 that supports the base sheet 2A when the projecting mold part 11 is inserted into the base sheet 2A. The support 12 is arranged on the other surface 2U side of the base sheet 2A, and serves to make the base sheet 2A less likely to warp/bend when the projecting mold part 11 is inserted from the one surface 2D side. Thus, the support 12 is arranged in a section, of the base sheet 2A, other than a region where the projecting mold part 11 is inserted into the base sheet 2A. In the manufacturing device 100C of the first embodiment, the support 12 is constituted by a pair of plate-like members extending parallel to the transporting direction (Y direction) on the base sheet 2A's respective lateral sides along the transporting direction (Y direction). The supports 12 extend from the protrusion forming section 10, through the cooling section 20, and up to a position where the release section 30 terminates.

The material constituting the support 12 may be the same as the material of the projecting mold part 11, and may be formed of a synthetic resin, for example.

As illustrated in FIG. 22, in the protrusion forming step of the first embodiment, the pair of supports 12, 12—which is arranged on the other surface 2U side (upper surface side) of the continuous base sheet 2A paid out from the material roll and being transported in the Y direction—supports the base sheet 2A's respective lateral sides along the transporting direction (Y direction). Then, by using the box-motion-type projecting mold part 11, the tip end portion of each projecting mold 110 of the projecting mold part 11 is brought into contact from the one surface 2D side (lower surface side) in a section, of the base sheet 2A, that is not supported by the supports 12—i.e., in a central region of the base sheet 2A between the pair of supports 12, 12.

Figures 25A, 25B, 25C, 25D, 25E:
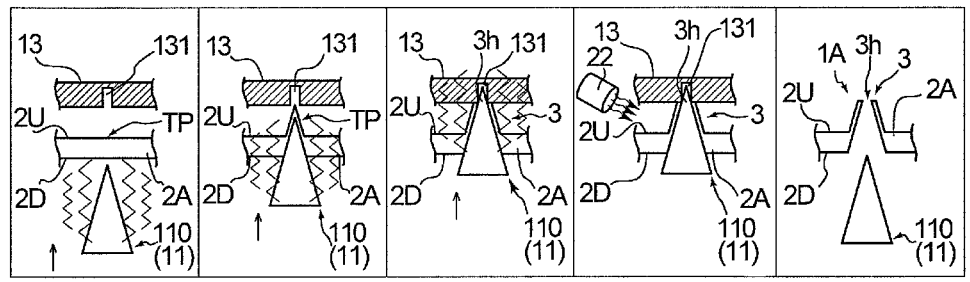
FIGS. 25(a) to 25(e) are diagrams illustrating steps for manufacturing a fine hollow protruding article having a through hole by employing the manufacturing device illustrated in FIG. 22.

Then, as illustrated in FIG. 25(a), in the first embodiment, the ultrasonic vibration device causes ultrasonic vibration of the projecting mold part 11 at each of the contact sections TP, and the contact sections TP are softened by generating heat in the contact sections TP by friction. Then, in the protrusion forming step of the first embodiment, as illustrated in FIG. 25(b), while softening the contact section TP, the projecting mold part 11 is raised from the one surface 2D side (lower surface side) of the base sheet 2A toward the other surface 2U side (upper surface side) and the tip end portion of each projecting mold 110 is inserted into the base sheet 2A.

Figure 26:
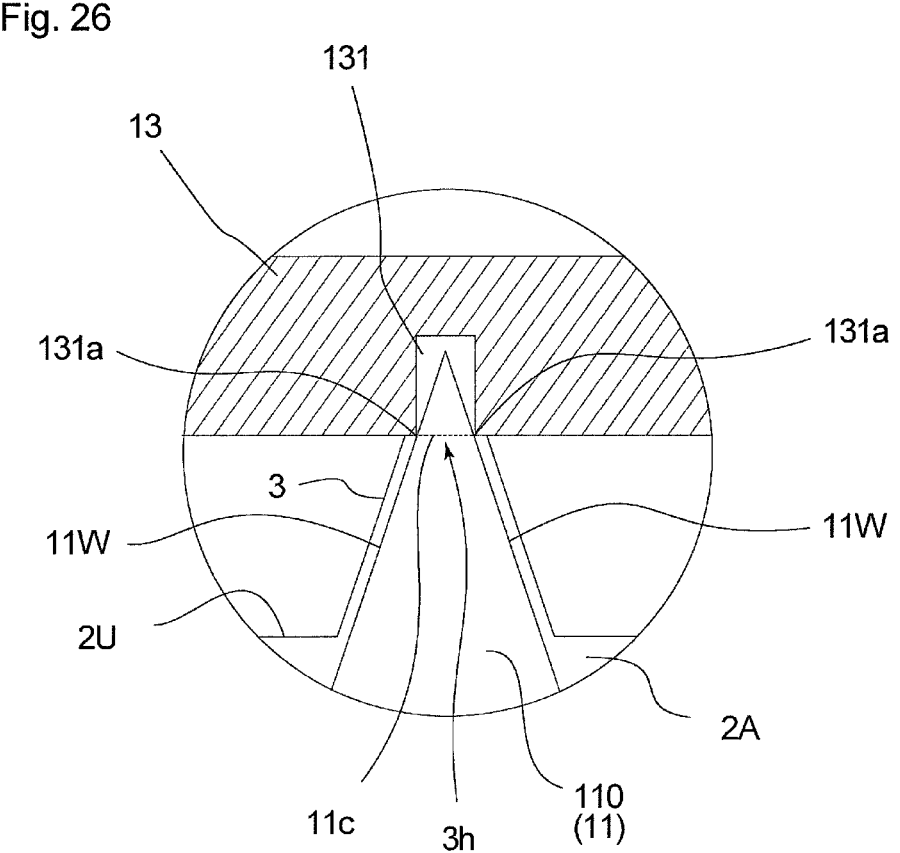
FIG. 26 is an enlarged cross-sectional view of a main part in the state illustrated in FIG. 25(c).

In the protrusion forming step of the first embodiment, as illustrated in FIG. 25(c), the projecting mold part 11 is inserted into the base sheet 2A until the peripheral wall 11W of the projecting mold part 11 comes into contact with the opening peripheral edge 131a of the depression 131 of the receiving member 13 and the projecting mold part 11 penetrates the base sheet 2A. FIG. 26 is an enlarged cross-sectional view of a main part in FIG. 25(c). As illustrated in FIG. 26, in the manufacturing device 100C of the first embodiment, the box-motion-type projecting mold part 11 is moved upward in the thickness direction (Z direction) by an electric actuator (not illustrated) and the projecting molds 110 of the projecting mold part 11 are inserted into the base sheet 2A, to form respective protrusions 3 that protrude from the other surface 2U side of the base sheet 2A. Then, the projecting mold part 11 is further moved upward in the thickness direction (Z direction) by the electric actuator (not illustrated), and, as illustrated in FIG. 26, the tip end of each projecting mold 110 of the projecting mold part 11 is inserted into the interior of each circular-cylindrical depression 131 formed in the receiving member 13's surface on the base sheet 2A side. Then, the base sheet 2A is brought into contact with the depression 131's opening peripheral edge 131a, and further, or simultaneously, the peripheral wall 11W of the projecting mold part 11 is brought into contact with opening peripheral edge 131a of each depression 131, causing the projecting mold part 11 to penetrate the base sheet 2A. In this way, in the manufacturing device 100C of the first embodiment, the projecting molds 110 of the projecting mold part 11 and the depressions 131 of the receiving member 13 form an array of protrusions 3 that protrude from the other surface 2U side of the base sheet 2A and that each have a through hole 3*h* penetrating the base sheet 2A to the other surface 2U side. In conjunction therewith, the box-motion-type projecting mold part 11 is used to move the array of protrusions 3—in which the respective projecting molds 110 of the projecting mold part 11 are inserted—parallel to the transporting direction (Y direction) of the base sheet 2A.

In the protrusion forming step of the first embodiment, as regards the ultrasonic vibration of the projecting mold part 11 by the ultrasonic vibration device, from the viewpoint of forming the protrusion 3 having a through hole 3*h*, the frequency is preferably 10 kHz or greater, more preferably 15 kHz or greater, and preferably 50 kHz or less, more preferably 40 kHz or less, and more specifically, preferably from 10 to 50 kHz, more preferably from 15 to 40 kHz.

Further, from the viewpoint of forming the protrusion 3 having a through hole 3*h*, the amplitude of the ultrasonic vibration of the projecting mold part 11 by the ultrasonic vibration device is preferably 1 µm or greater, more preferably 5 µm or greater, and preferably 60 µm or less, more preferably 50 µm or less, and more specifically, preferably from 1 to 60 µm, more preferably from 5 to 50 µm. In cases of using an ultrasonic vibration device as in the first embodiment, in the protrusion forming step, the frequency and the amplitude of the ultrasonic vibration of the projecting mold part 11 simply need to be adjusted to fall within the aforementioned ranges.

In the protrusion forming step of the first embodiment, from the viewpoint of efficiently forming the protrusion 3 having a through hole 3*h*, the insertion speed for inserting the projecting mold part 11 into the base sheet 2A is preferably 0.1 mm/s or greater, more preferably 1 mm/s or greater, and preferably 1000 mm/s or less, more preferably 800 mm/s or less, and more specifically, preferably from 0.1 to 1000 mm/s, more preferably from 1 to 800 mm/s.

In the protrusion forming step of the first embodiment, from the viewpoint of efficiently forming the through hole 3*h* in each protrusion 3, the insertion height of the projecting mold part 11 inserted into the base sheet 2A is greater than the distance between the receiving member 13 and the base sheet 2A—i.e., higher than the protrusion height H1 of the protrusion 3 of the microneedle array 1M being manufactured—and is preferably 0.01 mm or greater, more preferably 0.02 mm or greater, and preferably 10 mm or less, more preferably 5 mm or less, and more specifically, preferably from 0.01 to 10 mm, more preferably from 0.02 to 5 mm. Herein, "insertion height" refers to the distance between the apex of the projecting mold 110 of the projecting mold part 11 and the other surface 2U (upper surface) of the base sheet 2A in a state where the projecting mold 110 of the projecting mold part 11 is inserted furthest in the base sheet 2A. So, the insertion height in the protrusion forming step refers to the distance measured in the perpendicular direction from the other surface 2U to the apex of the projecting mold 110 in a state where the projecting mold 110 has been inserted furthest in the protrusion forming step and the projecting mold 110 has emerged from the other surface 2U of the base sheet 2A.

The softening time is the time until the projecting mold part/protrusion is transported to the next step (cooling step) after stopping the elevation of the heated-state projecting mold part 11 while keeping the projecting molds 110 of the projecting mold part 11 inserted in the interior of the respective protrusions 3. In the protrusion forming step of the first embodiment, although a too-long softening time will result in excessive softening of the respective contact sections TP in the base sheet 2A, from the viewpoint of supplementing insufficient softening, the softening time is preferably 0 seconds or longer, more preferably 0.1 seconds or longer, and preferably 10 seconds or less, more preferably 5 seconds or less, and more specifically, preferably from 0 to 10 seconds, more preferably from 0.1 to 5 seconds.

Next, in the manufacturing device 100C of the first embodiment, as illustrated in FIG. 22, a cooling section 20 is provided downstream of the protrusion forming section 10. As illustrated in FIG. 22, the cooling section 20 includes a cold air blowing device 21. In the first embodiment, after the protrusion forming step, the protrusions 3 are cooled by using this cold air blowing device 21 in a state where the projecting mold part 11 is inserted in the interior of the protrusions 3 (cooling step). More specifically, the cold air blowing device 21 covers the entirety of the other surface 2U side (upper surface side) and the one surface 2D side (lower surface side) of the continuous base sheet 2A being transported, and the continuous base sheet 2A is transported inside the cold air blowing device 21 along the transporting direction (Y direction). An air vent 22 (cf. FIG. 25(*d*)) for blowing cold air is provided inside the tunnel of the cold air blowing device 21 between the other surface 2U side (upper surface side) of the base sheet 2A and the receiving member 13, and cooling is performed by blowing cold air from the air vent 22. Note that the cooling temperature of the cold air blowing device 21 and the cooling time are controlled by the control means (not illustrated) provided to the manufacturing device 100C of the first embodiment.

In the cooling step of the first embodiment, as illustrated in FIG. 22, the box-motion-type projecting mold parts 11 are employed for transporting the base sheet 2A parallel to the transporting direction (Y direction) into the tunnel of the cold air blowing device 21 in a state where the projecting molds 110 of the projecting mold part 11 are inserted in the interior of the respective protrusions 3, and, as illustrated in FIG. 25(*d*), the protrusions 3 are cooled by blowing cold air from the air vent 22 arranged on the other surface 2U side (upper surface side) of the base sheet 2A inside the tunnel, with the projecting molds 110 of the projecting mold part 11 still inserted in the interior of the respective protrusions 3. Note that, during cooling, ultrasonic vibration of the projecting mold part 11 by the ultrasonic vibration device may be continued or stopped, but from the viewpoint of maintaining the opening area of the through hole 3*h* of each protrusion 3 constant, it is preferable that the ultrasonic vibration is stopped.

From the viewpoint of formation of the protrusion 3 having a through hole 3*h*, the temperature of the cold air to be blown is preferably −50° C. or higher, more preferably −40° C. or higher, and preferably 26° C. or lower, more preferably 10° C. or lower, and more specifically, preferably from −50 to 26° C., more preferably from −40 to 10° C.

From the viewpoint of balancing moldability and processing time, the cooling time for cooling by blowing the cold air is preferably 0.01 seconds or longer, more preferably 0.5 seconds or longer, and preferably 60 seconds or less, more preferably 30 seconds or less, and more specifically, preferably from 0.01 to 60 seconds, more preferably from 0.5 to 30 seconds.

Next, in the manufacturing device 100C of the first embodiment, as illustrated in FIG. 22, a release section 30 is provided downstream of the cooling section 20. In the first embodiment, the projecting mold part 11 is withdrawn from the interior of the protrusion 3 after the cooling step, to form a precursor 1A of the microneedle array 1M (release step). More specifically, in the release step of the first embodiment, as illustrated in FIG. 25(e), the projecting mold part 11 is lowered from the one surface 2D side (lower surface side) of the base sheet 2A by using the box-motion-type projecting mold part 11, and the projecting molds 110 of the projecting mold part 11 are withdrawn from the state where the projecting molds 110 of the projecting mold part 11 are inserted in the interior of the respective protrusions 3, to form a precursor 1A of a continuous fine hollow protruding article, which ultimately becomes a microneedle array 1M wherein protrusions 3 each having a through hole 3h and having a hollow interior are arranged in an array.

Next, in the manufacturing device 100C of the first embodiment, as illustrated in FIG. 22, a cutting section 40 is provided downstream of the release section 30. In the manufacturing device 100C of the first embodiment, the cutting section 40 includes a cutter part 41 having a cutter blade at its tip end, and an anvil part 42. The cutter blade of the cutter part 41 is formed so as to have a wider width than the entire width (length in the X direction) of the precursor 1A of the continuous fine hollow protruding article. In the first embodiment, after the release step, the precursor 1A of the continuous fine hollow protruding article is transported between the pair of the cutter part 41 and the anvil part 42, and each section between arrays of protrusions 3, 3 adjacent to one another in the transporting direction (Y direction) is cut with the cutter blade of the cutter part 41, to continuously manufacture pieces of microneedle arrays 1M wherein protrusions 3 each having a through hole 3h are arranged in an array.

Cutting of the precursor 1A of the continuous fine hollow protruding article only needs to be performed so as to extend along the lateral direction of each microneedle array 1M, and for example, can be performed in a straight line along the lateral direction of each microneedle array 1M. Alternatively, cutting may be performed such that the cutting line depicts a curve. In either case, it is preferable to employ a cutting pattern that does not give rise to trimmed parts as a result of cutting.

Next, in the manufacturing device 100C of the first embodiment, as illustrated in FIG. 22, a re-pitching section 50 is provided downstream of the cutting section 40. In the manufacturing device 100C of the first embodiment, the re-pitching section 50 includes: a plurality of rollers 51 arranged such that their rotation axes are parallel to one another; and an endless transporting belt 52 that bridges the rollers 51. A suction box 53 is provided inside the transporting belt 52. The transporting belt 52 is provided with a plurality of penetrating holes (not illustrated) for sucking air from the exterior of the circulating track toward the interior thereof by activating the suction box 53. Note that the transportation speed of the transporting belt 52 is faster than the transportation speed of the base sheet 2A up to the cutting section 40.

In the first embodiment, the pieces of microneedle arrays 1M are continuously moved onto the fast transporting belt 52 while being sucked by the suction box 53 through the penetrating holes (not illustrated), and the distance between consecutive microneedle arrays 1M, 1M adjacent to one another in the transporting direction (Y direction) is widened, thereby rearranging the microneedle arrays 1M with predetermined distances therebetween and manufacturing microneedle arrays 1M as fine hollow protruding articles 1.

As described above, in the manufacturing method of the first embodiment for manufacturing a microneedle array 1M having through holes 3h by using the manufacturing device 100C of the first embodiment, a projecting mold part 11 including an ultrasonic vibration device and a receiving member 13 arranged at a distance from the base sheet 2A are used, and the projecting mold part 11 is inserted into the base sheet 2A until a portion of the projecting mold part 11 comes into contact with the receiving member 13 on the side more toward the tip-end portion than the base and penetrates the base sheet 2A. Thus, it is possible to manufacture high-quality microneedle arrays 1M with through holes 3h having high precision in the height of the protrusions 3 on the fine hollow protruding article and high precision in the size of the through hole 3h. Further, with the manufacturing method of the first embodiment, microneedle arrays 1M having through holes 3h can be manufactured through simple steps, and cost reduction can be achieved. Further, with the manufacturing method of the first embodiment, microneedle arrays 1M having through holes 3h can be mass-produced stably, continuously, and efficiently. Note that, in the present Specification, a "microneedle array having a through hole" refers to a "microneedle array having a microneedle, which is a protrusion having a through hole".

Further, according to the manufacturing method of the first embodiment, the receiving member 13 employed has depressions 131 at sections that come into contact with the respective projecting mold parts 11, and the shape of the opening peripheral edge 131a of each depression 131 matches a shape of an outer periphery 11c of the peripheral wall 11W of the projecting mold part 11, as illustrated in FIG. 24. Further, in the protrusion forming step of the first embodiment, as illustrated in FIG. 26, the tip end of each projecting mold 110 of the projecting mold part 11 is inserted into the interior of each circular-cylindrical depression 131 of the receiving member 13, and the peripheral wall 11W of the projecting mold part 11 is brought into contact with the opening peripheral edge 131a of the depression 131 at the outer periphery 11c of the peripheral wall 11W, causing the projecting mold part 11 to penetrate the base sheet 2A. By forming the through hole 3h in this way, the precision in the size of the through hole 3h is further improved, and it is possible to manufacture a microneedle array 1M having through holes 3h with even higher quality. Further, because the tip end of the circular-conic projecting mold 110 does not contact the receiving member 13, the durability of the projecting mold 110 is improved and the number of times of replacement can be reduced, and thus cost reduction can be achieved.

Further, according to the manufacturing method of the first embodiment, because an ultrasonic vibration device is employed as the heating means (not illustrated) of the projecting mold part 11, the cold air blowing device 21 does not necessarily have to be provided, and cooling can be achieved by simply turning off the vibration of the ultrasonic vibration device. From this viewpoint, using ultrasonic vibration as the heating means can simplify the device, and microneedle arrays 1M having through holes 3h can be manufacture at high speed. Further, heat is less likely to be transmitted to sections of the base sheet 2A that are not in contact with the projecting mold part 11 and cooling is performed efficiently by stopping the application of ultrasonic vibration; thus, deformation is less likely to occur in sections other than the section being molded, and microneedle arrays 1M with high precision can be manufactured.

Further, as described above, in the first embodiment, as illustrated in FIG. 25(a), the projecting mold part 11 is vibrated by the ultrasonic vibration device only at the contact section TP of the base sheet 2A in contact with the projecting mold part 11 and thereby the contact section TP is softened. Thus, microneedle arrays 1M with through holes 3h can be manufactured continuously and efficiently while saving energy.

Further, as described above, in the manufacturing device 100C of the first embodiment, the distance between the receiving member 13 and the base sheet 2A can be adjusted by the control means (not illustrated), and thus, the protrusion height H1 of the protrusion 3 of the microneedle array 1M being manufactured can be adjusted and changed easily. Further, in cases where the material of the receiving member 13 is easy to machine, the size of the through hole 3h can be changed easily by adjusting the size of the opening peripheral edge 131a of the depression 131. In this way, the shape of the microneedle array 1M having through holes 3h can be controlled freely.

Further, as described above, in the manufacturing device 100C of the first embodiment, the control means (not illustrated) can adjust, in the protrusion forming section 10, the operations of the projecting mold parts 11, the heating condition of the heating means (not illustrated) of the projecting mold part 11, the softening time of the contact section TP of the base sheet 2A, and the insertion speed of the projecting mold part 11 into the base sheet 2A. Also, the control means (not illustrated) controls, in the cooling section 20, the cooling temperature of the cold air blowing device 21, and the cooling time. Thus, by controlling, for example, the insertion speed of the projecting mold part 11 in the protrusion forming step by the control means (not illustrated), the thickness T1 of the microneedle array 1M being manufactured can be controlled. Also, by controlling, for example, the insertion height of the projecting mold part 11 in the protrusion forming step, the insertion amount of the projecting mold part 11 into the base sheet 2A can be changed easily, and the protrusion height H1 of the microneedle array 1M to be manufactured can be controlled. Thus, by controlling at least one of a condition of the heating means of the projecting mold part 11, the insertion height of the projecting mold part 11 into the base sheet 2A, the softening time of the contact section TP of the base sheet 2A, the insertion speed of the projecting mold part 11 into the base sheet 2A in the protrusion forming step, the cooling conditions in the cooling step, and the shape of the projecting mold part 11, the thickness T1, etc., of the protrusion 3 constituting the microneedle array 1M can be controlled freely, and the shape of the microneedle array 1M having through holes 3h can be controlled freely.

Further, as described above, in the first embodiment, as illustrated in FIG. 22, the pair of supports 12, 12—which is arranged on the other surface 2U side (upper surface side) of the base sheet 2A—is used to support the base sheet 2A's respective lateral sides along the transporting direction (Y direction), and the projecting mold part 11 is brought into contact from the one surface 2D side (lower surface side)—which is on the opposite side from where the supports 12 are arranged—in the base sheet 2A's central region which is in a free floating state between the pair of supports 12, 12, to thereby soften the contact section TP and form a protrusion 3. Because there is no need to provide a depression, etc., into which the projecting mold part 11 is fitted to form the protrusion 3, it is possible to suppress an increase in cost, and to precisely and efficiently form the protrusion 3 of the microneedle array 1M to be manufactured.

Next, the invention (third invention) will be described according to a second embodiment with reference to FIGS. 27 to 29. Note that the following description mainly focuses on features that are different from those of the foregoing first embodiment.

In the manufacturing device 100C of the first embodiment used in the foregoing first embodiment, the heating means (not illustrated) of the projecting mold part 11 is an ultrasonic vibration device. In the manufacturing device 100D of the second embodiment used in the second embodiment, a heating heater device is used instead.

Figure 27:
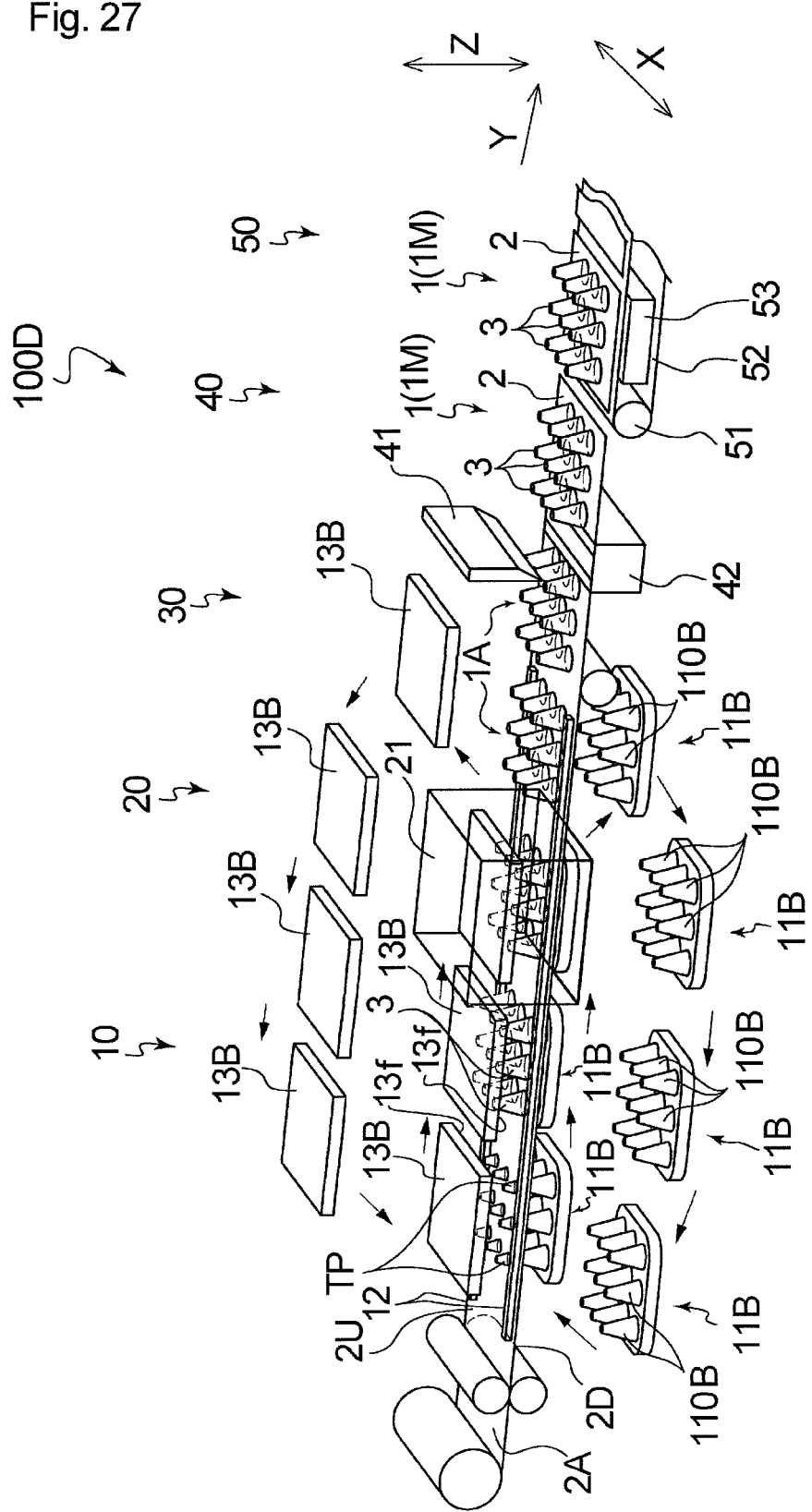
FIG. 27 is a diagram illustrating an overall configuration of a second embodiment of a manufacturing device for manufacturing the fine hollow protruding article illustrated in FIG. 19.

As illustrated in FIG. 27, as in the manufacturing device 100C of the first embodiment, the manufacturing device 100D of the second embodiment includes, from the upstream side toward the downstream side: a protrusion forming section 10 for forming protrusions 3 in a base sheet 2A; a cooling section 20; a release section 30; a cutting section 40; and a re-pitching section 50. In the manufacturing device 100D of the second embodiment, as illustrated in FIGS. 27 and 28, nine truncated circular-conic projecting molds 110B are arranged on the projecting mold part 11B of the protrusion forming section 10 so that their tip ends 110t face upward. Note that, although the projecting molds 110B are shaped in a truncated circular-conic shape, they may have a truncated pyramid shape.

As illustrated in FIG. 28, each projecting mold 110B of the projecting mold part 11B has a truncated circular-conic shape, and the tip end 110t constitutes a circular flat surface. The area of the circular flat surface matches the opening area S1 of the through hole 3h located at the tip-end portion of each protrusion 3 of the microneedle array 1M being manufactured.

In the manufacturing device 100D of the second embodiment, the surface of the box-motion-type receiving member 13B in the protrusion forming section 10 that comes into contact with the projecting mold part 11B is a flat surface 13f. In the protrusion forming step of the second embodiment, the projecting mold part 11B is inserted into the base sheet 2A until the tip end 110t of the projecting mold part 11B comes into contact with the flat surface 13f of the receiving member 13B and the projecting mold part 11B penetrates the base sheet 2A. The second embodiment employing the manufacturing device 100D of the second embodiment is described below with reference to FIG. 29.

In cases where the heating means (not illustrated) of the projecting mold part 11B is a heating heater device as in the manufacturing device 100D of the second embodiment, the heating heater device heats the projecting mold part 11B at each of the contact sections TP, and the contact sections TP are softened by generating heat at the contact sections TP, as illustrated in FIG. 29(a). Then, in the protrusion forming step of the second embodiment, as illustrated in FIG. 29(b), while softening the contact section TP, the projecting mold part 11B is raised from the one surface 2D side (lower surface side) of the base sheet 2A toward the other surface 2U side (upper surface side) and the projecting molds 110B are inserted into the base sheet 2A.

In the protrusion forming step of the second embodiment, as illustrated in FIG. 29(c), the projecting mold part 11B is inserted into the base sheet 2A until the circular flat surface of the tip end 110t of each projecting mold 110B of the projecting mold part 11B comes into contact with the flat surface 13f of the receiving member 13B and the projecting mold part 11B penetrates the base sheet 2A. In the manufacturing device 100D of the second embodiment, the box-motion-type projecting mold part 11B is moved upward in the thickness direction (Z direction) by an electric actuator (not illustrated) and the truncated circular-conic projecting molds 110B of the projecting mold part 11B are inserted into the base sheet 2A, to form respective protrusions 3 that protrude from the other surface 2U side of the base sheet 2A. Then, the projecting mold part 11B is further moved upward in the thickness direction (Z direction) by the electric actuator (not illustrated), and the flat surface at the tip end 110t of each projecting mold 110B of the projecting mold part 11B is brought into contact with the flat surface 13f of the receiving member 13, thereby causing the projecting mold part 11B to penetrate the base sheet 2A. In this way, in the manufacturing device 100D of the second embodiment, the truncated circular-conic projecting molds 110 of the projecting mold part 11B and the flat surface 13f of the receiving member 13 form an array of protrusions 3 that protrude from the other surface 2U side of the base sheet 2A and that each have a through hole 3h penetrating the base sheet 2A to the other surface 2U side.

In the protrusion forming step of the second embodiment, from the viewpoint of forming the protrusion 3, the heating temperature of the base sheet 2A by the projecting mold part 11B is preferably equal to or higher than the glass transition temperature (Tg) of the base sheet 2A being used to below the melting temperature thereof, and more preferably, equal to or higher than the softening temperature to below the melting temperature thereof. More specifically, the heating temperature is preferably 30° C. or higher, more preferably 40° C. or higher, and preferably 300° C. or lower, more preferably 250° C. or lower, and more specifically, preferably from 30 to 300° C., more preferably from 40 to 250° C. When a heating heater device is used as in the second embodiment, the heating temperature of the projecting mold part 11B simply needs to be adjusted within the aforementioned range in the protrusion forming step. Also in cases where the base sheet 2A is heated by using an ultrasonic vibration device as in the first embodiment, the heating temperature is employed as the temperature range of a section of the base sheet 2A that comes into contact with the projecting mold 110. It should be noted that the glass transition temperature (Tg) is measured according to the following measurement method, and the softening temperature is measured according to JIS K-7196 "Testing method for softening temperature of thermoplastic film and sheeting by thermomechanical analysis".

Note that the "glass transition temperature (Tg) of the base sheet" refers to the glass transition temperature (Tg) of the resin constituting the base sheet. In cases where there are a plurality of types of constituent resins and the plurality of glass transition temperatures (Tg) are different from each other, the heating temperature of the base sheet by the heating means is preferably at least equal to or higher than the lowest glass transition temperature (Tg) among the plurality of glass transition temperatures (Tg), and more preferably equal to or higher than the highest glass transition temperature (Tg) among the plurality of glass transition temperatures (Tg).

The same applies to the "softening temperature of the base sheet", as with the glass transition temperature (Tg). In cases where there are a plurality of types of constituent resins in the base sheet and the plurality of softening temperatures are different from each other, the heating temperature of the base sheet by the heating means is preferably at least equal to or higher than the lowest softening temperature among the plurality of softening temperatures, and more preferably equal to or higher than the highest softening temperature among the plurality of softening temperatures.

In cases where the base sheet includes two or more types of resins having different melting points, the heating temperature of the base sheet by the heating means is preferably below the lowest melting point among the plurality of melting points.

{Method for Measuring Glass Transition Temperature (Tg)}

The glass transition temperature is determined by measuring the heat quantity by using a DSC measurement device. More specifically, the measurement device used is a differential scanning calorimeter (Diamond DSC) from Perkin Elmer. A 10 mg test piece is sampled from the base sheet. As for the measurement conditions, the temperature is kept constant at 20° C. for 5 minutes, and then the temperature is raised from 20° C. to 320° C. at a rate of 5° C./minute, to obtain a DSC curve wherein the horizontal axis indicates temperature and the vertical axis indicates heat quantity. The glass transition temperature Tg is determined from the DSC curve.

Next, in the cooling step of the second embodiment, as in the cooling step of the first embodiment, as illustrated in FIG. 29(d), the protrusions 3 are cooled by blowing cold air from the air vent 22 arranged on the other surface 2U side (upper surface side) of the base sheet 2A inside the tunnel, with the projecting molds 110 of the projecting mold part 11 still inserted in the interior of the respective protrusions 3. Note that, during cooling, heating of the projecting mold part 11 with the heating heater device may be continued or stopped.

In cases where the heating means (not illustrated) of the projecting mold part 11 is a heating heater device as in the manufacturing device 100D of the second embodiment, cooling may be performed naturally in the cooling section 20 provided downstream of the protrusion forming section 10. It is, however, preferable to provide a cold air blowing device 21 and perform active cooling.

Next, in the release step of the second embodiment, as in the release step of the first embodiment, as illustrated in FIG. 29(e), the projecting mold part 11 is lowered from the one surface 2D side (lower surface side) of the base sheet 2A, and the projecting molds 110 of the projecting mold part 11 are withdrawn from the state where the projecting molds 110 of the projecting mold part 11 are inserted in the interior of the respective protrusions 3, to form a precursor 1A of a continuous fine hollow protruding article, which ultimately becomes a microneedle array 1M wherein protrusions 3 each having a through hole 3h and having a hollow interior are arranged in an array.

Next, in the second embodiment, as in the first embodiment, cutting is performed with the cutter blade of the cutter part 41, to continuously manufacture pieces of microneedle arrays 1M wherein protrusions 3 each having a through hole 3h are arranged in an array, and the microneedle arrays 1M are re-arranged in the re-pitching section 50.

As described above, according to the manufacturing method of the second embodiment, the projecting mold part 11B is inserted into the base sheet 2A until the tip end 110t of the projecting mold part 11B comes into contact with the flat surface 13f of the receiving member 13B and the projecting mold part 11B penetrates the base sheet 2A, to thereby continuously manufacture microneedle arrays 1M in which protrusions 3, each having a through hole 3h, are arranged in an array. Thus, the opening area S1 of the through hole 3h—which is located at the tip end portion of each protrusion 3 of the microneedle array 1M being manufactured—can be controlled simply by changing the size of the circular shape of the tip end 110t of each projecting mold 110B. Also, by adjusting the distance between the receiving member 13B and the base sheet 2A by the control means (not illustrated), the protrusion height H1 of each protrusion 3 can be adjusted and changed easily. Thus, it is possible to manufacture high-quality microneedle arrays 1M having through holes 3h.

Further, as described above, in the second embodiment, as illustrated in FIG. 29(a), the projecting mold part 11B is heated by the heating heater device only at the contact sections TP of the base sheet 2A in contact with the projecting mold part 11B and thereby the contact sections TP are softened. Thus, microneedle arrays 1M having through holes 3h can be manufactured continuously and efficiently while saving energy. In contrast, in cases where the entire resin needs to be heated to the same temperature as the projecting mold part, not only is energy efficiency poor, but also various other problems may arise—such as pitch discrepancies between protrusions, distortion of the sheet, and difficulty in continuously transporting the sheet—due to the entire sheet getting soft. In the second embodiment, on the other hand, heat due to heating by the projecting mold part 11B is transmitted efficiently to the contact sections TP, and peripheral sections thereof are in an environment where heating can be left only to natural progression; thus, pitch discrepancies among the protrusions 3, as well as distortion of the base sheet 2A, are less likely to occur, and it is easy to transport the base sheet 2A continuously.

The present invention (first to third inventions) has been described above according to preferred embodiments thereof, but the invention (first to third inventions) is not limited to the foregoing embodiments, and can be modified as appropriate.

Figure 8:
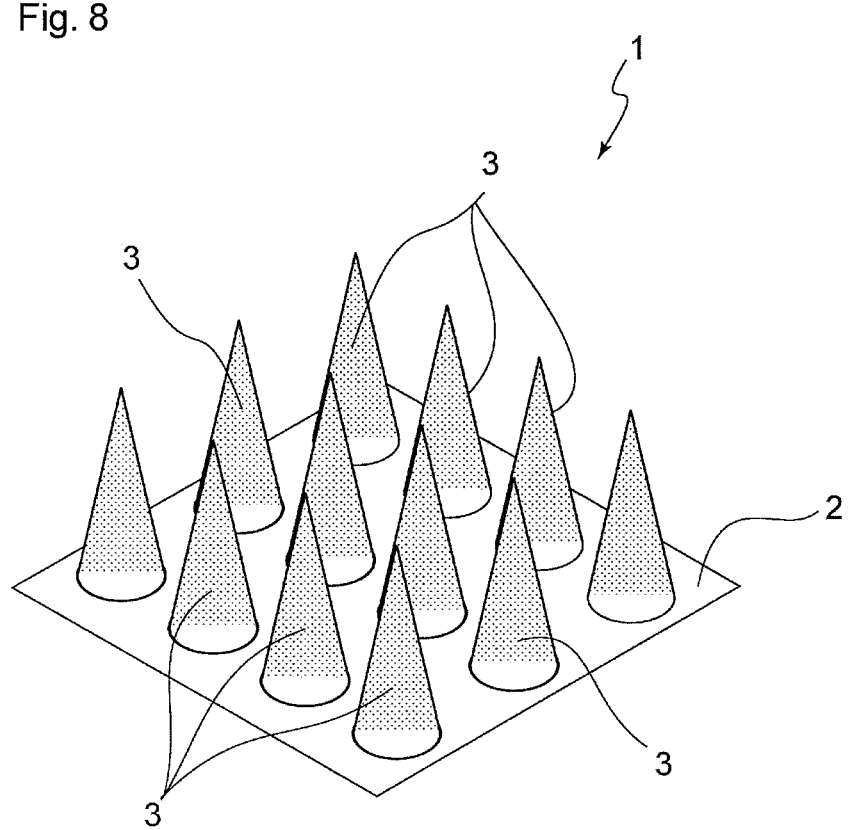
FIG. 8 is a schematic perspective view of an example of another fine hollow protruding article manufactured by a method for manufacturing a fine hollow protruding article of the invention (first invention).
Figure 9:
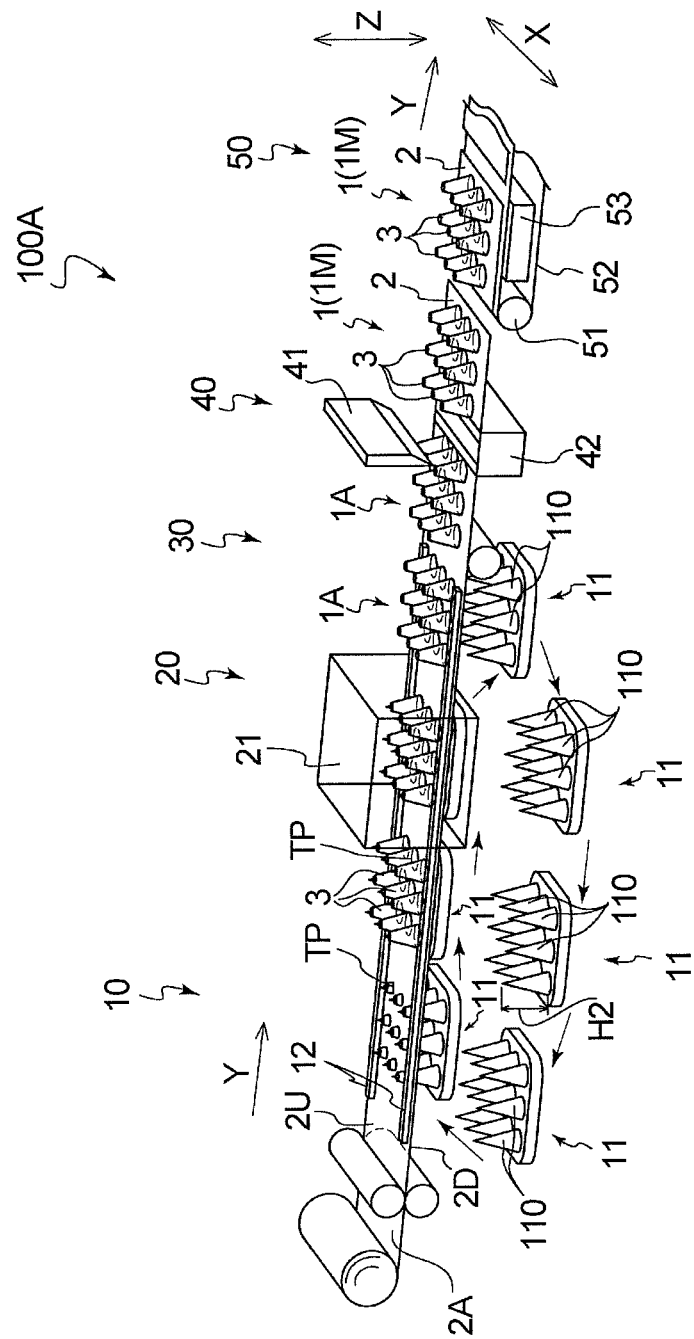
FIG. 9 is a diagram (corresponding to FIG. 4) illustrating an overall configuration of a preferred embodiment of a manufacturing device for manufacturing the fine hollow protruding article illustrated in FIG. 8.

For example, the fine hollow protruding article 1 manufactured according to the fine hollow protruding article manufacturing method according to the first embodiment employing the manufacturing device 100A of the first embodiment, or according to the second embodiment employing the manufacturing device 100A of the second embodiment, of the present invention (first invention) has a single protrusion 3 on the upper surface of the sheet-like basal portion 2. The fine hollow protruding article 1, however, may include a plurality of protrusions 3 in an array, as illustrated in FIG. 8. Herein, "include a plurality of protrusions 3 in an array" means that a plurality of protrusions 3 are provided on the upper surface of the sheet-like basal portion 2, and particularly, it is preferable that a plurality of protrusions 3 are arranged on the upper surface of the sheet-like basal portion 2 in a matrix consisting of a plurality of rows and a plurality of columns. When manufacturing a fine hollow protruding article 1 (1M) including a plurality of protrusions 3 in an array, it is possible to use a device as illustrated in FIG. 9. In the device illustrated in FIG. 9, the protrusion forming section 10 is provided with projecting mold parts 11 each having a plurality of projecting molds 110 corresponding to the number and arrangement of the plurality of protrusions 3 and the outer shape of each protrusion 3. Alternatively, a fine hollow protruding article 1 having a plurality of protrusions 3 can be manufactured by inserting a single projecting mold part 11a plurality of times into the base sheet 2A. Note that, in the manufacturing device 100A illustrated in FIG. 9, sections/parts that are the same as in the manufacturing device 100A illustrated in FIG. 4 are accompanied by the same reference numbers.

In cases of operating the sheet transmission system intermittently, it is possible to use a protrusion forming section 10 that can move only vertically in the thickness direction (Z direction) to form the protrusions, instead of the box-motion-type protrusion forming section 10 that follows an endless track.

Figure 10:
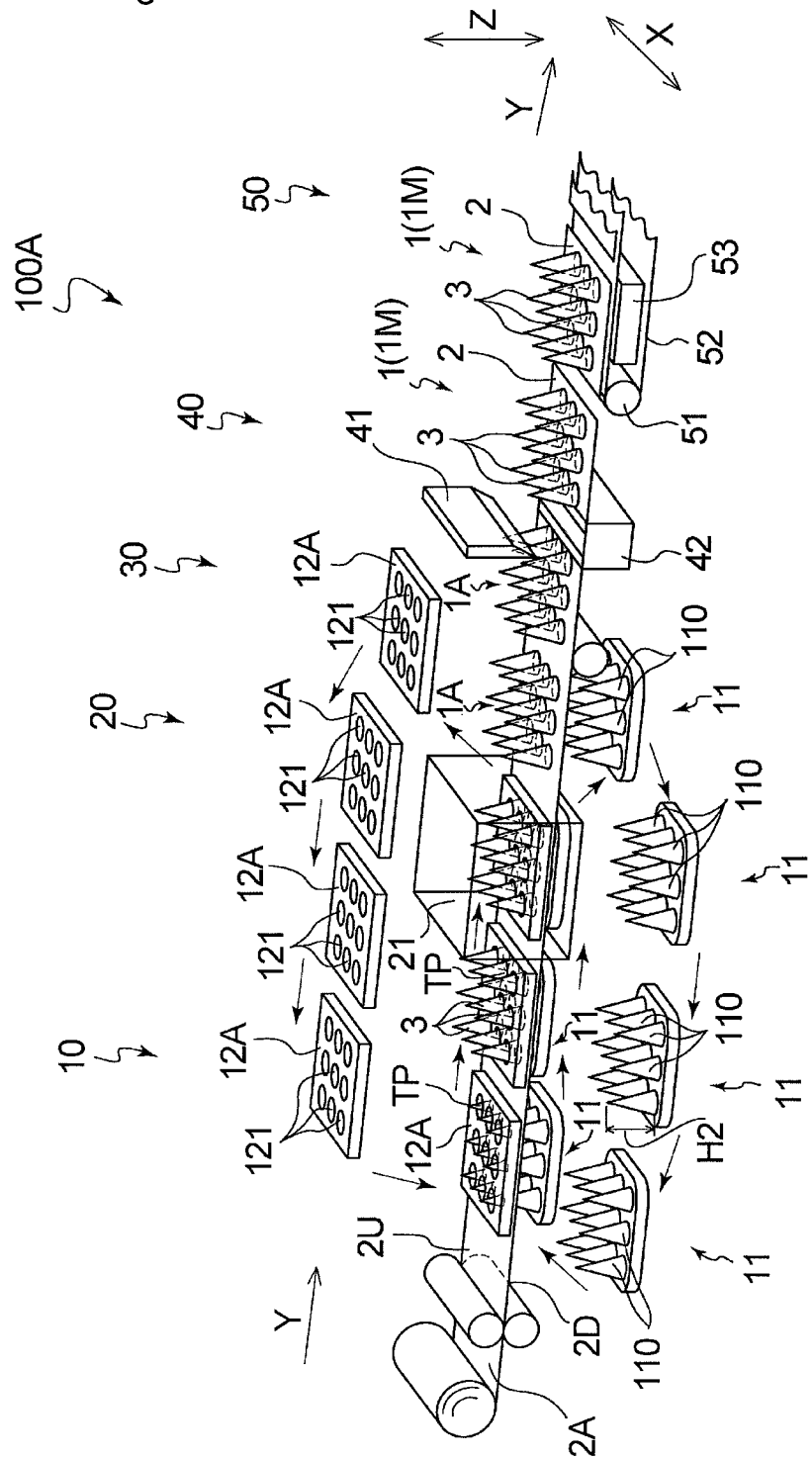
FIG. 10 is a diagram (corresponding to FIG. 4) illustrating an overall configuration of another preferred embodiment of a manufacturing device for manufacturing the fine hollow protruding article illustrated in FIG. 8.

The manufacturing device 100A of the first or second embodiment of the invention (first invention) includes a pair of plate-shaped supports 12, 12 that supports the base sheet 2A when the projecting mold part 11 is inserted into the base sheet 2A, as illustrated in FIG. 4. The support, however, does not have to be a pair of plate-shaped supports 12, 12, so long as it is arranged on the other surface 2U side of the base sheet 2A and supports the base sheet 2A. For example, instead of the pair of plate-shaped supports 12, 12, as illustrated in FIG. 10, a punching plate 12A—which is an example of an opening plate having through holes 121 opened at positions corresponding to the respective contact sections TP—can be arranged on the other surface 2U side of the base sheet 2A and can support the base sheet 2A as the projecting mold part 11 is inserted into the base sheet 2A. Herein, an opening plate is a plate having an opening into which a projecting mold 110 of the projecting mold part 11 can be inserted. In this embodiment, the opening is a penetrating through hole, but the opening can be non-penetrating. In cases of employing an opening plate, it is considered that a section, of the base sheet 2A, that is in opposition to the opening is not supported by the opening plate. In the manufacturing device 100A illustrated in FIG. 10, the protrusion forming section 10 is provided with projecting mold parts 11 each having a plurality of projecting molds 110 corresponding to the number and arrangement of the plurality of protrusions 3 and the outer shape of each protrusion 3. Further, in the manufacturing device 100A illustrated in FIG. 10, the opening plate 12A is arranged such that it can contact the other surface 2U side of the base sheet 2A. Note that, in the manufacturing device 100A illustrated in FIG. 10, sections/parts that are the same as in the manufacturing device 100A illustrated in FIG. 4 are accompanied by the same reference numbers.

In the manufacturing device 100A illustrated in FIG. 10, the base sheet 2A is sandwiched between the projecting mold part 11 and the opening plate 12A. In the manufacturing device 100A illustrated in FIG. 10, the opening plate 12A has one through hole 121 arranged at a position corresponding to the base sheet 2A's contact section TP that contacts one projecting mold 110 of a projecting mold part 11. However, a single through hole 121 may be arranged at a position corresponding to contact sections TP that contact a plurality of projecting molds 110. Note that, although the shape of each through hole 121 in a top view of the opening plate 12A is not particularly limited, the through hole has a circular shape in the manufacturing device 100A illustrated in FIG. 10.

The shape of the opening plate 12A is not particularly limited, but in the manufacturing device 100A illustrated in FIG. 10, the opening plate is plate-shaped. The length, in the Y direction, of the plate-shaped opening plate 12A is substantially the same as the length of the projecting mold part 11 in the Y direction. The length, in the X direction, of the plate-shaped opening plate is substantially the same as the length of the projecting mold part 11 in the X direction. In the manufacturing device 100A illustrated in FIG. 10, such plate-shaped opening plates 12A follow an endless track according to a box motion so as to operate corresponding to the operation of the box-motion-type projecting mold parts 11 while sandwiching the base sheet 2A being transported in the Y direction. Each of the box-motion-type opening plates 12A is arranged above and adjacent to the other surface 2U of the base sheet 2A in the thickness direction (Z direction), and can travel together with the base sheet 2A in the transporting direction (Y direction). The movement speed of the opening plate 12A in the transporting direction (Y direction) corresponds to the movement speed of the projecting mold part 11 in the transporting direction (Y direction), and is controlled by a control means (not illustrated) provided to the manufacturing device 100A illustrated in FIG. 10.

In the manufacturing device 100A of the first or second embodiment of the invention (first invention), the projecting mold part 11 is inserted into the base sheet 2A from below to above, as illustrated in FIG. 4. However, the positional relationship of the projecting mold part and/or the support with respect to the base sheet and the insertion direction are not limited thereto, and a fine hollow protruding article may be formed from above toward below.

Further, for example, in the first embodiment according to the invention (second invention) employing the manufacturing device 100B of the first embodiment, the frequency and amplitude of the ultrasonic vibration of the projecting mold part 11 in the protrusion elongating section 10B are the same as the frequency and amplitude of the ultrasonic vibration of the projecting mold part 11 in the protrusion precursor forming section 10A, thus not satisfying the aforementioned conditions (b) and (c), but the insertion speed in the protrusion elongating step is slower than the insertion speed in the protrusion precursor forming step, thus satisfying the aforementioned condition (a). Thus, the heat quantity applied from the projecting mold part 11 to the base sheet 2A in the protrusion elongating step is greater than the heat quantity applied from the projecting mold part 11 to the base sheet 2A in the protrusion precursor forming step. Further, in the second embodiment employing the manufacturing device 100B of the second embodiment, the heater temperature of the projecting mold part 11 in the protrusion elongating section 10B is the same temperature as the heater temperature of the projecting mold part 11 in the protrusion precursor forming section 10A, thus not satisfying the aforementioned condition (d), but the insertion speed in the protrusion elongating step is slower than the insertion speed in the protrusion precursor forming step, thus satisfying the aforementioned condition (a). Thus, the heat quantity applied from the projecting mold part 11 to the base sheet 2A in the protrusion elongating step is greater than the heat quantity applied from the projecting mold part 11 to the base sheet 2A in the protrusion precursor forming step. Stated differently, in the manufacturing methods of the first and second embodiments, the condition of the heating means of the projecting mold part 11 in the protrusion precursor forming step is the same as the condition of the heating means of the projecting mold part 11 in the protrusion elongating step; but the speed for further inserting the projecting mold part 11 into the base sheet 2A in the protrusion elongating step is slower than the speed for inserting the projecting mold part 11 into the base sheet 2A in the protrusion precursor forming step. However, it is possible to employ a manufacturing method wherein the speed for inserting the projecting mold part 11 into the base sheet 2A in the protrusion precursor forming step is the same as the speed for further inserting the projecting mold part 11 into the base sheet 2A in the protrusion elongating step, while the heat quantity applied to the base sheet 2A under the condition of the heating means of the projecting mold part 11 in the protrusion elongating step is greater than the heat quantity applied to the base sheet 2A under the condition of the heating means of the projecting mold part 11 in the protrusion precursor forming step. More specifically, the manufacturing method may not satisfy the aforementioned condition (a), but may satisfy the aforementioned condition (b) or (c) by making the frequency or amplitude of the ultrasonic vibration of the projecting mold part 11 in the protrusion elongating section 10B greater than the frequency or amplitude of the ultrasonic vibration of the projecting mold part 11 in the protrusion precursor forming section 10A, and as a result, the heat quantity applied from the projecting mold part 11 to the base sheet 2A in the protrusion elongating step may be made greater than the heat quantity applied from the projecting mold part 11 to the base sheet 2A in the protrusion precursor forming step. Alternatively, the manufacturing method may not satisfy the aforementioned condition (a), but may satisfy the aforementioned condition (d) by making the heater temperature of the projecting mold part 11 in the protrusion elongating section 10B higher than the heater temperature of the projecting mold part 11 in the protrusion precursor forming section 10A, and as a result, the heat quantity applied from the projecting mold part 11 to the base sheet 2A in the protrusion elongating step may be made greater than the heat quantity applied from the projecting mold part 11 to the base sheet 2A in the protrusion precursor forming step. Alternatively, all of the aforementioned conditions (a), (b), (c), and (d) may be satisfied.

Further, the microneedle array 1M—which is an example of a fine hollow protruding article 1 manufactured by the fine hollow protruding article manufacturing methods of the first and second embodiments of the invention (second invention)—has nine truncated circular-conic protrusions 3 arranged in an array (matrix) on the upper surface of a sheet-like basal portion 2; instead, the fine hollow protruding article may include only one protrusion 3. Further, in the microneedle array 1M manufactured by the fine hollow protruding article manufacturing methods of the first and second embodiments, the through hole 3h located at the tip end portion of each protrusion 3 is formed concentrically with the basal-side through hole 2h located in the lower surface; instead, the through hole 3h and the basal-side through hole 2h do not have to be concentric.

Further, the first and second embodiments of the invention (second invention) employ box-motion-type projecting mold parts 11 that follow an endless track. Instead, a microneedle array 1M may be manufactured by using a projecting mold part 11 that is movable only vertically in the thickness direction (Z direction) and gradually changing, from the protrusion precursor forming step to the protrusion elongating step, the heat quantity applied from the projecting mold part 11 to the base sheet 2A in the protrusion precursor forming step and the heat quantity applied from the projecting mold part 11 to the base sheet 2A in the protrusion elongating step.

Figure 18:
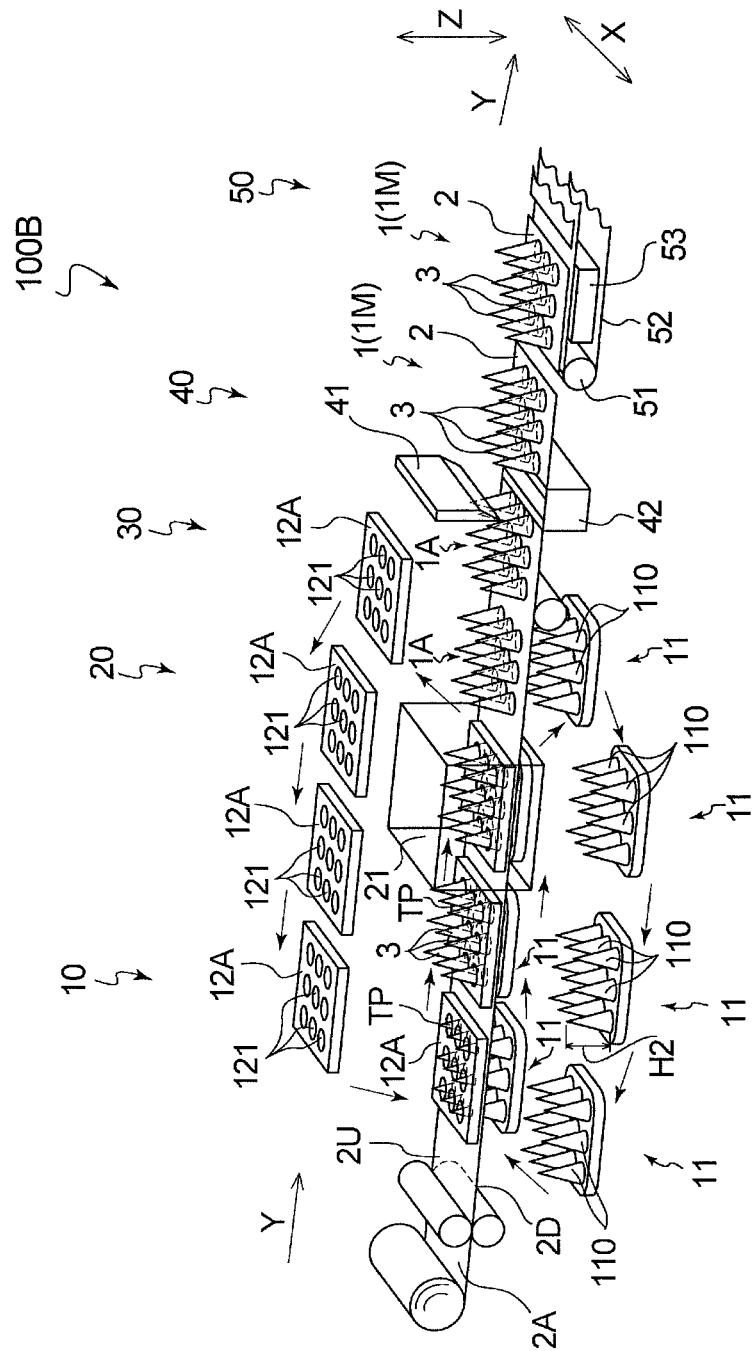
FIG. 18 is a diagram (corresponding to FIG. 14) illustrating an overall configuration of another preferred embodiment of a manufacturing device for manufacturing the fine hollow protruding article illustrated in FIG. 11.

The manufacturing device 100B of the first or second embodiment of the invention (second invention) includes a pair of plate-shaped supports 12, 12 that supports the base sheet 2A when the projecting mold part 11 is inserted into the base sheet 2A, as illustrated in FIG. 14. The support, however, does not have to be a pair of plate-shaped supports 12, 12, so long as it is arranged on the other surface 2U side of the base sheet 2A and supports the base sheet 2A. For example, instead of the pair of plate-shaped supports 12, 12, as illustrated in FIG. 18, a punching plate 12A—which is an example of an opening plate having through holes 121 opened at positions corresponding to the respective contact sections TP—can be arranged on the other surface 2U side of the base sheet 2A and can support the base sheet 2A as the projecting mold part 11 is inserted into the base sheet 2A. Herein, an opening plate is a plate having an opening into which a projecting mold 110 of the projecting mold part 11 can be inserted. In this embodiment, the opening is a penetrating through hole, but the opening can be non-penetrating. In cases of employing an opening plate, it is considered that a section, of the base sheet 2A, that is in opposition to the opening is not supported by the opening plate. In the manufacturing device 100B illustrated in FIG. 18, the protrusion forming section 10 is provided with projecting mold parts 11 each having a plurality of projecting molds 110 corresponding to the number and arrangement of the plurality of protrusions 3 and the outer shape of each protrusion 3. Further, in the manufacturing device 100B illustrated in FIG. 18, the opening plate 12A is arranged such that it can contact the other surface 2U side of the base sheet 2A. Note that, in the manufacturing device 100B illustrated in FIG. 18, sections/parts that are the same as in the manufacturing device 100B illustrated in FIG. 14 are accompanied by the same reference numbers.

In the manufacturing device 100B illustrated in FIG. 18, the base sheet 2A is sandwiched between the projecting mold part 11 and the opening plate 12A. In the manufacturing device 100B illustrated in FIG. 18, the opening plate 12A has one through hole 121 arranged at a position corresponding to the base sheet 2A's contact section TP that contacts one projecting mold 110 of a projecting mold part 11. However, a single through hole 121 may be arranged at a position corresponding to contact sections TP that contact a plurality of projecting molds 110. Note that, although the shape of each through hole 121 in a top view of the opening plate 12A is not particularly limited, the through hole has a circular shape in the manufacturing device 100B illustrated in FIG. 18.

The shape of the opening plate 12A is not particularly limited, but in the manufacturing device 100B illustrated in FIG. 18, the opening plate is plate-shaped. The length, in the Y direction, of the plate-shaped opening plate 12A is substantially the same as the length of the projecting mold part 11 in the Y direction. The length, in the X direction, of the plate-shaped opening plate is substantially the same as the length of the projecting mold part 11 in the X direction. In the manufacturing device 100B illustrated in FIG. 18, such plate-shaped opening plates 12A follow an endless track according to a box motion so as to operate corresponding to the operation of the box-motion-type projecting mold parts 11 while sandwiching the base sheet 2A being transported in the Y direction. Each of the box-motion-type opening plates 12A is arranged above and adjacent to the other surface 2U of the base sheet 2A in the thickness direction (Z direction), and can travel together with the base sheet 2A in the transporting direction (Y direction). The movement speed of the opening plate 12A in the transporting direction (Y direction) corresponds to the movement speed of the projecting mold part 11 in the transporting direction (Y direction), and is controlled by a control means (not illustrated) provided to the manufacturing device 100B illustrated in FIG. 18.

In the manufacturing device 100B of the first or second embodiment of the invention (second invention), the projecting mold part 11 is inserted into the base sheet 2A from below to above, as illustrated in FIG. 14. However, the positional relationship of the projecting mold part and/or the support with respect to the base sheet and the insertion direction are not limited thereto, and a microneedle array 1M may be formed from above toward below.

Figure 30:
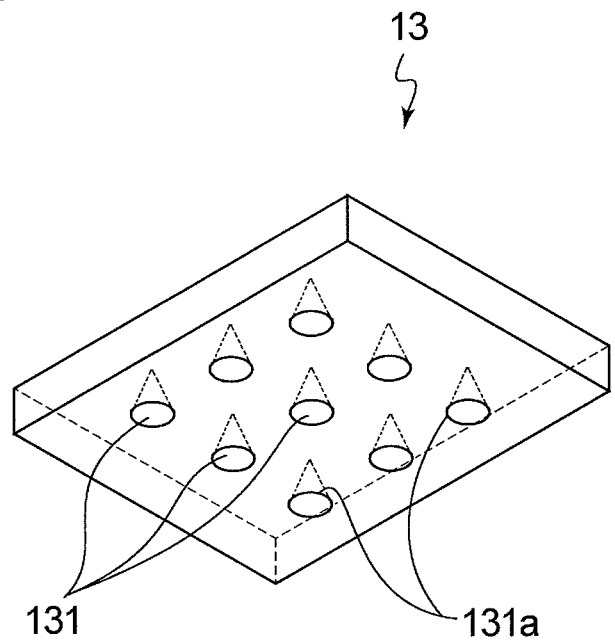
FIG. 30 is a perspective view, as viewed from the base sheet side, of a receiving member provided to a manufacturing device according to another embodiment for manufacturing the fine hollow protruding article illustrated in FIG. 19.

Further, for example, the manufacturing device 100C of the first embodiment of the invention (third invention) includes a receiving member 13 having depressions 131 each formed in a circular-cylindrical shape, as illustrated in FIG. 24. Instead, as illustrated in FIG. 30, the receiving member 13 may include depressions 131 formed in a circular-conic shape. Each circular-conic depression 131 illustrated in FIG. 30 is shaped so as to correspond to the tip end portion of the circular-conic projecting mold 110 of the projecting mold part 11 illustrated in FIG. 23, and the shape of the opening peripheral edge 131a of each depression 131 matches the shape of the outer periphery 11c of the projecting mold 110 (cf. FIG. 23). The circular-cylindrical depression 131 of the receiving member 13 illustrated in FIG. 24 is shaped so as to have a bottom, but may instead be shaped so as to penetrate the receiving member.

Further, the microneedle array 1M—which is an example of a fine hollow protruding article 1 manufactured by the fine hollow protruding article manufacturing methods of the first and second embodiments of the invention (third invention)—has nine truncated circular-conic protrusions 3 arranged in an array (matrix) on the upper surface of a sheet-like basal portion 2; instead, the fine hollow protruding article may include only one protrusion 3. Further, in the microneedle array 1M manufactured by the fine hollow protruding article manufacturing methods of the first and second embodiments, the through hole 3h located at the tip end portion of each protrusion 3 is formed concentrically with the basal-side through hole 2h located in the lower surface; however, the through hole 3h and the basal-side through hole 2h do not have to be concentric.

Further, the first and second embodiments of the invention (third invention) employ box-motion-type projecting mold parts 11 that follow an endless track. Instead, a microneedle array 1M may be manufactured by using a projecting mold part 11 that is movable only vertically in the thickness direction (Z direction).

Figure 31:
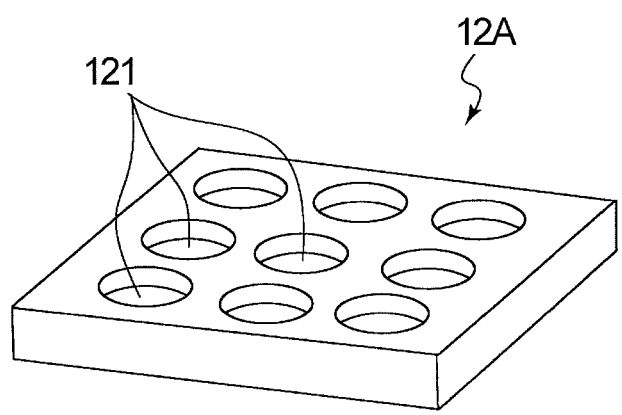
FIG. 31 is a perspective view of an opening plate used in a manufacturing device of another preferred embodiment for manufacturing the fine hollow protruding article illustrated in FIG. 19.

The manufacturing device 100C of the first embodiment or the manufacturing device 100D of the second embodiment of the invention (third invention) includes a pair of plate-shaped supports 12, 12 that supports the base sheet 2A when the projecting mold part 11 is inserted into the base sheet 2A, as illustrated in FIG. 22. The support, however, does not have to be a pair of plate-shaped supports 12, 12, so long as it is arranged on the other surface 2U side of the base sheet 2A and supports the base sheet 2A. For example, instead of the pair of plate-shaped supports 12, 12, as illustrated in FIG. 31, a punching plate 12A—which is an example of an opening plate having through holes 121 opened at positions corresponding to the respective contact sections TP—can be arranged on the other surface 2U side of the base sheet 2A and can support the base sheet 2A as the projecting mold part 11 is inserted into the base sheet 2A. Herein, an opening plate is a plate having an opening into which a projecting mold 110 of the projecting mold part 11 can be inserted. In this embodiment, the opening is a penetrating through hole, but the opening can be non-penetrating. In cases of employing an opening plate, it is considered that a section, of the base sheet 2A, that is in opposition to the opening is not supported by the opening plate. Further, in the manufacturing device 100C illustrated in FIG. 22 or the manufacturing device 100D illustrated in FIG. 27, in cases where the punching plate 12A illustrated in FIG. 31 is employed instead of the support 12, the opening plate 12A is arranged such that it contacts the other surface 2U side of the base sheet 2A.

In cases where the punching plate 12A illustrated in FIG. 31 is employed instead of the support 12 in the manufacturing device 100C illustrated in FIG. 22 or the manufacturing device 100D illustrated in FIG. 27, the base sheet 2A is sandwiched between the projecting mold part 11 and the opening plate 12A. The punching plate 12A illustrated in FIG. 31 has one through hole 121 arranged at a position corresponding to the base sheet 2A's contact section TP that contacts one projecting mold 110 of a projecting mold part 11. However, a single through hole 121 may be arranged at a position corresponding to contact sections TP that contact a plurality of projecting molds 110. Note that, although the shape of each through hole 121 in a top view of the opening plate 12A is not particularly limited, the through hole has a circular shape in the punching plate 12A illustrated in FIG. 31.

The shape of the opening plate 12A is not particularly limited, but in the punching plate 12A illustrated in FIG. 31, the opening plate is plate-shaped. The length, in the Y direction, of the plate-shaped opening plate 12A is substantially the same as the length of the projecting mold part 11 in the Y direction. The length, in the X direction, of the plate-shaped opening plate is substantially the same as the length of the projecting mold part 11 in the X direction. In the manufacturing device 100C illustrated in FIG. 22 or the manufacturing device 100D illustrated in FIG. 27, such plate-shaped opening plates 12A follow an endless track according to a box motion so as to operate corresponding to the operation of the box-motion-type projecting mold parts 11 while sandwiching the base sheet 2A being transported in the Y direction. Each of the box-motion-type opening plates 12A is arranged above and adjacent to the other surface 2U of the base sheet 2A in the thickness direction (Z direction), and can travel together with the base sheet 2A in the transporting direction (Y direction). The movement speed of the opening plate 12A in the transporting direction (Y direction) corresponds to the movement speed of the projecting mold part 11 in the transporting direction (Y direction), and is controlled by a control means (not illustrated) provided to the manufacturing device 100C or the manufacturing device 100D.

In cases of manufacturing a fine hollow protruding article by using the opening plate 12A illustrated in FIG. 31, it is preferable to arrange the opening plate 12A between the base sheet 2A and the receiving member 13.

In the manufacturing device 100C of the first embodiment or the manufacturing device 100D of the second embodiment of the invention (third invention), the projecting mold part 11 is inserted into the base sheet 2A from below to above, as illustrated in FIG. 22. However, the positional relationship of the projecting mold part and/or the support with respect to the base sheet and the insertion direction are not limited thereto, and a microneedle array 1M may be formed from above toward below.

Features omitted from explanation in any of the foregoing embodiments and features only provided in one of the foregoing embodiments can be applied as appropriate to other embodiments, and features of each of the foregoing embodiments are interchangeable among other embodiments as appropriate.

In relation to the foregoing embodiments, the invention also discloses the following methods for manufacturing fine hollow protruding articles.

{1}

A method for manufacturing a fine hollow protruding article having a hollow interior, the method comprising:
 a protrusion forming step of
  bringing a projecting mold part that includes a heating means into contact from one-surface side of a base sheet including a thermoplastic resin, and, while softening, with heat, a contact section in the base sheet where the projecting mold part contacts the base sheet, inserting the projecting mold part into the base sheet, to form a protrusion that protrudes from another-surface side of the base sheet;
 a cooling step of cooling the protrusion in a state where the projecting mold part is inserted in an interior of the protrusion; and
 a release step of withdrawing the projecting mold part from the interior of the protrusion after the cooling step, to form the fine hollow protruding article.

{2}

The method for manufacturing a fine hollow protruding article as set forth in clause {1}, wherein: the protrusion forming step is performed by using a support that supports the base sheet when the projecting mold part is inserted into the base sheet; the support is arranged on the other-surface side of the base sheet; and the protrusion is formed by bringing the projecting mold part into contact from the one-surface side in a section, of the base sheet, that is not supported by the support.

{3}

The method for manufacturing a fine hollow protruding article as set forth in clause {2}, wherein an opening plate having an opening into which a projecting mold of the projecting mold part can be inserted is used as the support.

{4}

The method for manufacturing a fine hollow protruding article as set forth in clause {3}, wherein the opening plate has a plurality of the openings.

{5}

The method for manufacturing a fine hollow protruding article as set forth in clause {3} or {4}, wherein one projecting mold is inserted into the respective opening of the opening plate.

{6}

The method for manufacturing a fine hollow protruding article as set forth in clause {3} or {4}, wherein a plurality of the projecting molds are inserted into the opening of the opening plate.

{7}

The method for manufacturing a fine hollow protruding article as set forth in any one of clauses {1} to {6}, wherein the shape of the fine hollow protruding article is controlled by controlling at least one condition selected from a heating condition of the projecting mold part in the protrusion forming step, the softening time of the contact section of the base sheet in the protrusion forming step, the insertion speed of the projecting mold part into the base sheet in the protrusion forming step, and a cooling condition in the cooling step.

{8}

The method for manufacturing a fine hollow protruding article as set forth in any one of clauses {1} to {7}, wherein: a continuous base sheet is used as the base sheet; and the fine hollow protruding articles are formed continuously on the other-surface side of the continuous base sheet.

{9}

The method for manufacturing a fine hollow protruding article as set forth in any one of clauses {1} to {8}, wherein the heating temperature of the base sheet due to heating with the projecting mold part is equal to or higher than the glass transition temperature of the base sheet to below the melting temperature thereof.

{10}

The method for manufacturing a fine hollow protruding article as set forth in any one of clauses {1} to {9}, wherein the heating temperature of the base sheet due to heating with the projecting mold part is equal to or higher than the softening temperature of the base sheet to below the melting temperature thereof.

{11}

The method for manufacturing a fine hollow protruding article as set forth in clause {9} or {10}, wherein the heating temperature is from 30 to 300° C.

{12}

The method for manufacturing a fine hollow protruding article as set forth in any one of clauses {1} to {11}, wherein the heating means of the projecting mold part is a heating heater device.

{13}

The method for manufacturing a fine hollow protruding article as set forth in any one of clauses {1} to {11}, wherein: the heating means of the projecting mold part is an ultrasonic vibration device; and the contact section is softened by causing ultrasonic vibration of the projecting mold part by the ultrasonic vibration device and generating heat in the contact section by friction.

{14}

The method for manufacturing a fine hollow protruding article as set forth in clause {13}, wherein the frequency of the ultrasonic vibration is from 10 to 50 kHz, more preferably from 15 to 40 kHz.

{15}

The method for manufacturing a fine hollow protruding article as set forth in clause {13} or {14}, wherein the amplitude of the ultrasonic vibration is from 1 to 60 µm, more preferably from 5 to 50 µm.

{16}

The method for manufacturing a fine hollow protruding article as set forth in any one of clauses {1} to {15}, wherein, in the protrusion forming step, no other heating means is provided except for the heating means of the projecting mold part.

{17}

The method for manufacturing a fine hollow protruding article as set forth in any one of clauses {1} to {16}, wherein: a temperature equal to or above the softening temperature of the base sheet is applied only to a section of the base sheet where the projecting mold part is inserted, and a region in the vicinity thereof; and in other regions of the base sheet, temperature rise is left only to natural progression.

{18}

The method for manufacturing a fine hollow protruding article as set forth in any one of clauses {1} to {17}, wherein the height of the projecting mold part is equal to or slightly higher than the height of the fine hollow protruding article being manufactured.

{19}

The method for manufacturing a fine hollow protruding article as set forth in any one of clauses {1} to {18}, wherein the height of the projecting mold part is from 0.01 to 30 mm, more preferably from 0.02 to 20 mm.

{20}

The method for manufacturing a fine hollow protruding article as set forth in any one of clauses {1} to {19}, wherein the tip end diameter of the projecting mold part is from 0.001 to 1 mm, more preferably from 0.005 to 0.5 mm.

{21}

The method for manufacturing a fine hollow protruding article as set forth in any one of clauses {1} to {20}, wherein the base diameter of the projecting mold part is from 0.1 to 5 mm, more preferably from 0.2 to 3 mm.

{22}

The method for manufacturing a fine hollow protruding article as set forth in any one of clauses (1) to {21}, wherein the tip end angle of the projecting mold part is from 1 to 60 degrees, more preferably from 5 to 45 degrees.

{23}

The method for manufacturing a fine hollow protruding article as set forth in any one of clauses {1} to {22}, wherein, in the cooling step, cooling is applied by a cold air blowing device in a state where the projecting mold part is inserted in the interior of the protrusion.

{24}

The method for manufacturing a fine hollow protruding article as set forth in clause {23}, wherein the temperature of the cold air is from −50 to 26° C., preferably from −40 to 10° C.

{25}

The method for manufacturing a fine hollow protruding article as set forth in clause {23} or {24}, wherein the cooling time for cooling by blowing the cold air is from 0 to 60 seconds, more preferably from 0.5 to 30 seconds.

{26}

The method for manufacturing a fine hollow protruding article as set forth in any one of clauses {1} to {25}, wherein, in the cooling step, cooling is performed naturally without cooling with a cold air blowing device.

{27}

The method for manufacturing a fine hollow protruding article as set forth in any one of clauses {1} to {26}, wherein the projecting mold part includes a plurality of projections for forming a plurality of protrusions by inserting the projecting mold part into different positions of the base sheet in the protrusion forming step.

{28}

The method for manufacturing a fine hollow protruding article as set forth in clause {27}, wherein, in the protrusion forming step, a plurality of projecting mold parts arranged in an array are inserted into the base sheet, to form a fine hollow protruding article including a plurality of protrusions arranged in an array.

{29}

The method for manufacturing a fine hollow protruding article having a through hole as set forth in any one of clauses {1} to {28}, wherein the protrusion is a microneedle.

{30}

The method for manufacturing a fine hollow protruding article as set forth in clause {29}, wherein the fine hollow protruding article is a microneedle array in which a plurality of the protrusions are arranged on the base sheet. {31}

The method for manufacturing a fine hollow protruding article as set forth in any one of clauses {1} to {30}, wherein the protrusion forming step comprises:

a protrusion precursor forming step of
bringing the projecting mold part that includes the heating means into contact from the one-surface side of the thermoplastic-resin-including base sheet, and, while softening, with heat, the contact section in the base sheet, inserting the projecting mold part into the base sheet, to form a hollow protrusion precursor that protrudes from the other-surface side of the base sheet and that has a through hole that penetrates the tip end on the other-surface side of the base sheet; and a protrusion elongating step of further inserting the projecting mold part into the base sheet in a state where the projecting mold part is inserted in the interior of the protrusion precursor while softening, with heat, the contact section in the base sheet, to form a protrusion that further protrudes from the other surface of the base sheet.

{32}

The method for manufacturing a fine hollow protruding article having a through hole as set forth in any one of clauses {1} to {30}, wherein the method is for manufacturing a fine hollow protruding article having a through hole, and comprises:

the protrusion forming step for forming the protrusion, the protrusion forming step including:

a protrusion precursor forming step of
bringing the projecting mold part that includes the heating means into contact from the one-surface side of the thermoplastic-resin-including base sheet, and,
while softening, with heat, the contact section in the base sheet, inserting the projecting mold part into the base sheet, to form a hollow protrusion precursor that protrudes from the other-surface side of the base sheet and that has a through hole that penetrates the tip end on the other-surface side of the base sheet; and a protrusion elongating step of further inserting the projecting mold part into the base sheet in a state where the projecting mold part is inserted in the interior of the protrusion precursor while softening, with heat, the contact section in the base sheet, to form a protrusion that further protrudes from the other surface of the base sheet;

the cooling step of cooling the protrusion in a state where the projecting mold part is inserted in the interior of the protrusion; and the release step of withdrawing the projecting mold part from the interior of the protrusion after the cooling step, to form the fine hollow protruding article having a through hole.

{33}

The method for manufacturing a fine hollow protruding article having a through hole as set forth in clause {31} or {32}, wherein the heat quantity applied from the projecting mold part to the base sheet in the protrusion elongating step is greater than the heat quantity applied from the projecting mold part to the base sheet in the protrusion precursor forming step.

{34}

The method for manufacturing a fine hollow protruding article having a through hole as set forth in any one of clauses {31} to {33}, wherein the heat quantity per unit insertion height applied from the projecting mold part to the base sheet in the protrusion precursor forming step and the heat quantity per unit insertion height applied from the projecting mold part to the base sheet in the protrusion elongating step continuously change from the protrusion precursor forming step to the protrusion elongating step.

{35}

The method for manufacturing a fine hollow protruding article having a through hole as set forth in any one of clauses {31} to {34}, wherein the shape of the fine hollow protruding article having a through hole is controlled by controlling at least one condition selected from a condition of the heating means of the projecting mold part in the protrusion forming step, the insertion height of the projecting mold part into the base sheet in the protrusion forming step, the softening time of the contact section of the base sheet in the protrusion forming step, the insertion speed of the projecting mold part into the base sheet in the protrusion forming step, and the shape of the projecting mold part.

{36}

The method for manufacturing a fine hollow protruding article having a through hole as set forth in clause {35}, wherein the shape of the fine hollow protruding article having a through hole is controlled by controlling the insertion speed of the projecting mold part into the base sheet in the protrusion forming step.

{37}

The method for manufacturing a fine hollow protruding article having a through hole as set forth in any one of clauses {31} to {36}, wherein: the condition of the heating means of the projecting mold part in the protrusion precursor forming step is the same as the condition of the heating means of the projecting mold part in the protrusion elongating step; and the insertion speed for further inserting the projecting mold part into the base sheet in the protrusion elongating step is slower than the insertion speed for inserting the projecting mold part into the base sheet in the protrusion precursor forming step.

{38}

The method for manufacturing a fine hollow protruding article having a through hole as set forth in any one of clauses {31} to {36}, wherein: the insertion speed for inserting the projecting mold part into the base sheet in the protrusion precursor forming step is the same as the insertion speed for further inserting the projecting mold part into the base sheet in the protrusion elongating step; and the heat quantity applied to the base sheet under the condition of the heating means of the projecting mold part in the protrusion elongating step is greater than the heat quantity applied to the base sheet under the condition of the heating means of the projecting mold part in the protrusion precursor forming step.

{39}

The method for manufacturing a fine hollow protruding article having a through hole as set forth in any one of clauses {31} to {38}, wherein: the heating means of the projecting mold part is an ultrasonic vibration device; and the contact section is softened by causing ultrasonic vibration of the projecting mold part by the ultrasonic vibration device and generating heat in the contact section by friction.

{40}

The method for manufacturing a fine hollow protruding article having a through hole as set forth in clause {39}, wherein the frequency of the ultrasonic vibration is from 10 to 50 kHz, more preferably from 15 to 40 kHz.

{41}

The method for manufacturing a fine hollow protruding article having a through hole as set forth in clause {39} or {40}, wherein the amplitude of the ultrasonic vibration is from 1 to 60 μm, more preferably from 5 to 50 μm.

{42}

The method for manufacturing a fine hollow protruding article having a through hole as set forth in any one of clauses {31} to {38}, wherein: the heating means of the projecting mold part is a heater; and the contact section is softened by heating the projecting mold part by the heater device.

{43}

The method for manufacturing a fine hollow protruding article having a through hole as set forth in any one of clauses {31} to {42}, wherein: the protrusion precursor forming step and the protrusion elongating step are performed by using the projecting mold part that includes a plurality of projecting molds; and a plurality of fine hollow protruding articles each having a through hole are formed in an array.

{44}

The method for manufacturing a fine hollow protruding article having a through hole as set forth in any one of clauses {31} to {43}, wherein: the protrusion forming step is performed by using a support that supports the base sheet when the projecting mold part is inserted into the base sheet; the support is arranged on the other-surface side of the base sheet; and the protrusion is formed by bringing the projecting mold part into contact from the one-surface side in a section, of the base sheet, that is not supported by the support.

{45}
The method for manufacturing a fine hollow protruding article as set forth in clause {44}, wherein an opening plate having an opening into which a projecting mold of the projecting mold part can be inserted is used as the support.

{46}
The method for manufacturing a fine hollow protruding article as set forth in clause {45}, wherein the opening plate has a plurality of the openings.

{47}
The method for manufacturing a fine hollow protruding article as set forth in clause {45} or {46}, wherein one projecting mold is inserted into the respective opening of the opening plate.

{48}
The method for manufacturing a fine hollow protruding article as set forth in any one of clauses {44} to {46}, wherein a plurality of the projecting molds are inserted into the opening of the opening plate.

{49}
The method for manufacturing a fine hollow protruding article having a through hole as set forth in any one of clauses {31} to {48}, wherein: a continuous base sheet is used as the base sheet; and the fine hollow protruding articles are formed continuously on the other-surface side of the continuous base sheet.

{50}
The method for manufacturing a fine hollow protruding article having a through hole as set forth in any one of clauses {31} to {49}, wherein the heating temperature of the base sheet due to heating with the projecting mold part is equal to or higher than the glass transition temperature of the base sheet to below the melting temperature thereof.

{51}
The method for manufacturing a fine hollow protruding article having a through hole as set forth in any one of clauses {31} to {49}, wherein the heating temperature of the base sheet due to heating with the projecting mold part is equal to or higher than the softening temperature of the base sheet to below the melting temperature thereof.

{52}
The method for manufacturing a fine hollow protruding article having a through hole as set forth in clause {50} or {51}, wherein the heating temperature is from 30 to 300° C.

{53}
The method for manufacturing a fine hollow protruding article having a through hole as set forth in any one of clauses {31} to {52}, wherein, in the protrusion forming step, no other heating means is provided except for the heating means of the projecting mold part.

{54}
The method for manufacturing a fine hollow protruding article having a through hole as set forth in any one of clauses {31} to {53}, wherein: a temperature equal to or above the softening temperature of the base sheet is applied only to a section of the base sheet where the projecting mold part is inserted, and a region in the vicinity thereof; and in other regions of the base sheet, temperature rise is left only to natural progression.

{55}
The method for manufacturing a fine hollow protruding article having a through hole as set forth in any one of clauses {31} to {54}, wherein the height of the projecting mold part is equal to or slightly higher than the height of the fine hollow protruding article being manufactured.

{56}
The method for manufacturing a fine hollow protruding article having a through hole as set forth in any one of clauses {31} to {55}, wherein the height of the projecting mold part is from 0.01 to 30 mm, more preferably from 0.02 to 20 mm.

{57}
The method for manufacturing a fine hollow protruding article having a through hole as set forth in any one of clauses {31} to {56}, wherein the tip end diameter of the projecting mold part is from 0.001 to 1 mm, more preferably from 0.005 to 0.5 mm.

{58}
The method for manufacturing a fine hollow protruding article having a through hole as set forth in any one of clauses {31} to {57}, wherein the base diameter of the projecting mold part is from 0.1 to 5 mm, more preferably from 0.2 to 3 mm.

{59}
The method for manufacturing a fine hollow protruding article having a through hole as set forth in any one of clauses {31} to {58}, wherein the tip end angle of the projecting mold part is from 1 to 60 degrees, more preferably from 5 to 45 degrees.

{60}
The method for manufacturing a fine hollow protruding article as set forth in any one of clauses {31} to {59}, wherein, in the cooling step, cooling is applied by a cold air blowing device in a state where the projecting mold part is inserted in the interior of the protrusion.

{61}
The method for manufacturing a fine hollow protruding article having a through hole as set forth in clause {60}, wherein the temperature of the cold air is from −50 to 26° C., preferably from −40 to 10° C.

{62}
The method for manufacturing a fine hollow protruding article having a through hole as set forth in clause {60} or {61}, wherein the cooling time for cooling by blowing the cold air is from 0 to 60 seconds, more preferably from 0.5 to 30 seconds.

{63}
The method for manufacturing a fine hollow protruding article having a through hole as set forth in any one of clauses {31} to {62}, wherein, in the cooling step, cooling is performed naturally without cooling with a cold air blowing device.

{64}
The method for manufacturing a fine hollow protruding article having a through hole as set forth in any one of clauses {31} to {63}, wherein the protrusion is a microneedle.

{65}
The method for manufacturing a fine hollow protruding article as set forth in any one of clauses {1} to {30}, the method comprising:
a protrusion forming step of
bringing the projecting mold part that includes the heating means into contact from the one-surface side of the thermoplastic-resin-including base sheet, and,
while softening, with heat, the contact section in the base sheet, inserting the projecting mold part into the base sheet toward the other-surface side of the base sheet, to form a protrusion that protrudes from the other-surface side of the base sheet;

a cooling step of cooling the protrusion in a state where the projecting mold part is inserted in the interior of the protrusion; and a release step of withdrawing the projecting mold part from the interior of the protrusion after the cooling step, to form the fine hollow protruding article, wherein:

the protrusion forming step employs a receiving member arranged at a distance from the other surface of the base sheet; and in the protrusion forming step, a through hole is formed in the protrusion by the projecting mold part coming into contact with the receiving member.

{66}

The method for manufacturing a fine hollow protruding article as set forth in clause {65}, wherein: the receiving member has a depression; the shape of an opening peripheral edge of the depression matches a shape of an outer periphery of the peripheral wall of the projecting mold part at a position where the peripheral wall comes into contact with the receiving member; and in the protrusion forming step, the projecting mold part is inserted into the base sheet until the peripheral wall of the projecting mold part comes into contact with the opening peripheral edge of the depression of the receiving member and the projecting mold part penetrates the base sheet.

{67}

The method for manufacturing a fine hollow protruding article as set forth in clause {66}, wherein the tip end of the projecting mold part does not contact the receiving member.

{68}

The method for manufacturing a fine hollow protruding article as set forth in clause {65}, wherein: the receiving member's surface that comes into contact with the projecting mold part is a flat surface; and in the protrusion forming step, the projecting mold part is inserted into the base sheet until the tip end of the projecting mold part comes into contact with the flat surface of the receiving member and the projecting mold part penetrates the base sheet.

{69}

The method for manufacturing a fine hollow protruding article as set forth in any one of clauses {65} to {68}, wherein the shape of the fine hollow protruding article having a through hole is controlled by controlling at least one condition selected from a condition of the heating means of the projecting mold part in the protrusion forming step, the insertion height of the projecting mold part into the base sheet in the protrusion forming step, the softening time of the contact section of the base sheet in the protrusion forming step, the insertion speed of the projecting mold part into the base sheet in the protrusion forming step, a cooling condition in the cooling step, and the shape of the projecting mold part.

{70}

The method for manufacturing a fine hollow protruding article as set forth in any one of clauses {65} to {69}, wherein the heating means of the projecting mold part is an ultrasonic vibration device; and the contact section is softened by causing ultrasonic vibration of the projecting mold part by the ultrasonic vibration device and generating heat in the contact section by friction.

{71}

The method for manufacturing a fine hollow protruding article as set forth in clause {70}, wherein the frequency of the ultrasonic vibration is from 10 to 50 kHz, more preferably from 15 to 40 kHz.

{72}

The method for manufacturing a fine hollow protruding article as set forth in clause {70} or {71}, wherein the amplitude of the ultrasonic vibration is from 1 to 60 μm, more preferably from 5 to 50 μm.

{73}

The method for manufacturing a fine hollow protruding article as set forth in any one of clauses {65} to {69}, wherein: the heating means of the projecting mold part is a heater; and the contact section is softened by heating the projecting mold part by the heater device.

{74}

The method for manufacturing a fine hollow protruding article as set forth in any one of clauses {65} to {73}, wherein: the protrusion forming step is performed by using the projecting mold part that includes a plurality of projecting molds; and a plurality of fine hollow protruding articles are formed in an array.

{75}

The method for manufacturing a fine hollow protruding article having a through hole as set forth in any one of clauses {65} to {74}, wherein the protrusion forming step is performed by using a support that supports the base sheet when the projecting mold part is inserted into the base sheet; the support is arranged on the other-surface side of the base sheet; and the protrusion is formed by bringing the projecting mold part into contact from the one-surface side in a section, of the base sheet, that is not supported by the support.

{76}

The method for manufacturing a fine hollow protruding article as set forth in clause {75}, wherein an opening plate having an opening into which a projecting mold of the projecting mold part can be inserted is used as the support.

{77}

The method for manufacturing a fine hollow protruding article as set forth in clause {76}, wherein the opening plate has a plurality of the openings.

{78}

The method for manufacturing a fine hollow protruding article as set forth in clause {76} or {77}, wherein one projecting mold is inserted into the respective opening of the opening plate.

{79}

The method for manufacturing a fine hollow protruding article as set forth in clause {76} or {77}, wherein a plurality of the projecting molds are inserted into the opening of the opening plate.

{80}

The method for manufacturing a fine hollow protruding article as set forth in any one of clauses {65} to {79}, wherein: a continuous base sheet is used as the base sheet; and the fine hollow protruding articles are formed continuously on the other-surface side of the continuous base sheet.

{81}

The method for manufacturing a fine hollow protruding article as set forth in any one of clauses {65} to {80}, wherein the heating temperature of the base sheet due to heating with the projecting mold part is equal to or higher than the glass transition temperature of the base sheet to below the melting temperature thereof.

{82}

The method for manufacturing a fine hollow protruding article as set forth in any one of clauses {65} to {81}, wherein the heating temperature of the base sheet due to heating with the projecting mold part is equal to or higher than the softening temperature of the base sheet to below the melting temperature thereof.

{83}

The method for manufacturing a fine hollow protruding article as set forth in clause {81} or {82}, wherein the heating temperature is from 30 to 300° C.

{84}

The method for manufacturing a fine hollow protruding article as set forth in any one of clauses {65} to {83}, wherein, in the protrusion forming step, no other heating means is provided except for the heating means of the projecting mold part.

{85}

The method for manufacturing a fine hollow protruding article as set forth in any one of clauses {65} to {84}, wherein: a temperature equal to or above the softening temperature of the base sheet is applied only to a section of the base sheet where the projecting mold part is inserted, and a region in the vicinity thereof; and in other regions of the base sheet, temperature rise is left only to natural progression.

{86}

The method for manufacturing a fine hollow protruding article as set forth in any one of clauses {65} to {85}, wherein the height of the projecting mold part is equal to or slightly higher than the height of the fine hollow protruding article being manufactured.

{87}

The method for manufacturing a fine hollow protruding article as set forth in any one of clauses {65} to {86}, wherein the height of the projecting mold part is from 0.01 to 30 mm, more preferably from 0.02 to 20 mm.

{88}

The method for manufacturing a fine hollow protruding article as set forth in any one of clauses {65} to {87}, wherein the tip end diameter of the projecting mold part is from 0.001 to 1 mm, more preferably from 0.005 to 0.5 mm.

{89}

The method for manufacturing a fine hollow protruding article as set forth in any one of clauses {65} to {88}, wherein the base diameter of the projecting mold part is from 0.1 to 5 mm, more preferably from 0.2 to 3 mm.

{90}

The method for manufacturing a fine hollow protruding article as set forth in any one of clauses {65} to {89}, wherein the tip end angle of the projecting mold part is from 1 to 60 degrees, more preferably from 5 to 45 degrees.

{91}

The method for manufacturing a fine hollow protruding article as set forth in any one of clauses {65} to {90}, wherein, in the cooling step, cooling is applied by a cold air blowing device in a state where the projecting mold part is inserted in the interior of the protrusion.

{92}

The method for manufacturing a fine hollow protruding article as set forth in clause {91}, wherein the temperature of the cold air is from −50 to 26° C., preferably from −40 to 10° C.

{93}

The method for manufacturing a fine hollow protruding article as set forth in clause {91} or {92}, wherein the cooling time for cooling by blowing the cold air is from 0 to 60 seconds, more preferably from 0.5 to 30 seconds.

{94}

The method for manufacturing a fine hollow protruding article as set forth in any one of clauses {65} to {90}, wherein, in the cooling step, cooling is performed naturally without cooling with a cold air blowing device.

{95}

The method for manufacturing a fine hollow protruding article as set forth in any one of clauses {65} to {94}, wherein the projecting mold part includes a plurality of projections for forming a plurality of protrusions by inserting the projecting mold part into different positions of the base sheet in the protrusion forming step.

{96}

The method for manufacturing a fine hollow protruding article as set forth in any one of clauses {65} to {95}, wherein the protrusion is a microneedle.

{97}

The method for manufacturing a fine hollow protruding article as set forth in clause {96}, wherein the fine hollow protruding article is a microneedle array in which a plurality of the protrusions are arranged on the base sheet.

EXAMPLES

The inventions (first to third inventions) are described in further detail below according to Examples. The scope of the inventions (first to third inventions), however, are not limited to the following Examples.

Preparation of Projecting Mold Part 11 of Manufacturing Device:

A projecting mold part made of SUS304, which is a type of stainless steel, and having a circular-conic tip end portion was prepared as the projecting mold part 11. The height H2 (height of the tapered portion) of the projecting mold part 11 was 2.5 mm, the tip end diameter D1 was 15 μm, and the base diameter D2 was 0.5 mm.

Preparation of Base Sheet 2A:

A continuous sheet made of polylactic acid (PLA) and having a thickness of 0.3 mm was prepared as the base sheet 2A.

Example 1A

A fine hollow protruding article 1 was manufactured according to the procedure of FIG. 6. More specifically, the heating means of the projecting mold part 11 was a heating heater device. As shown in Table 1, the manufacturing conditions were as follows: heating temperature: 140° C.; insertion height: 1.0 mm; insertion speed: 1 mm/s; softening time: 10 seconds; cooling time: 10 seconds.

Example 2A

A fine hollow protruding article 1 was manufactured according to the procedure of FIG. 7. More specifically, the heating means of the projecting mold part 11 was an ultrasonic vibration device. As shown in Table 1, the manufacturing conditions were as follows: frequency of ultrasonic vibration: 20 kHz; amplitude of ultrasonic vibration: 40 μm; insertion height: 1.0 mm; insertion speed: 10 mm/s; softening time: 0.5 seconds; cooling time: 2 seconds.

{Performance Evaluation}

For each of the fine hollow protruding articles of Examples 1A and 2A, the tip end diameter of the fine hollow protruding article and the base diameter of the fine hollow protruding article were measured according to the methods described above. The results are shown in Table 1 below.

Figure 32:
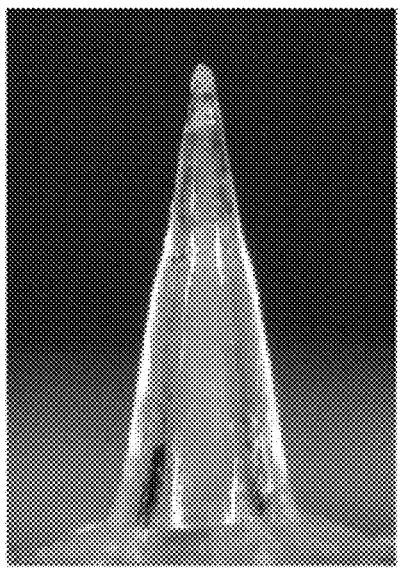
FIG. 32 is a photograph of the manufactured fine hollow protruding articles of Example 1A.
Figure 33:
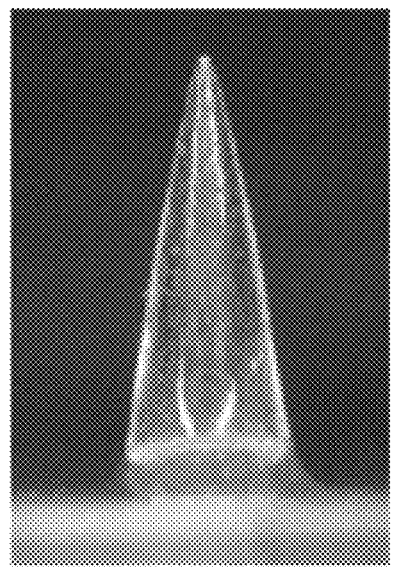
FIG. 33 is a photograph of the manufactured fine hollow protruding articles of Example 2A.

FIG. 32 is a photograph of the manufactured fine hollow protruding articles of Example 1 A; and FIG. 33 is a photograph of the manufactured fine hollow protruding articles of Example 2A.

TABLE 1

| | Embodiment | Unit | Example 1A | Example 2A |
|---|---|---|---|---|
| Manufacturing conditions | Heating temperature | ° C. | 140 | — |
| | Frequency of ultrasonic vibration | kHz | — | 20 |
| | Amplitude of ultrasonic vibration | μm | — | 40 |
| | Insertion height | mm | 1.0 | 1.0 |
| | Insertion speed | mm/s | 1 | 10 |
| | Softening time | s | 10 | 0.5 |
| | Cooling time | s | 10 | 2 |
| Fine hollow protruding article | Tip end diameter | μm | 42 | 35 |
| | Base diameter | μm | 380 | 380 |

As is clear from the results of Table 1, the fine hollow protruding articles of Examples 1A and 2A had excellent precision in shape. Thus, the manufacturing methods for manufacturing the respective fine hollow protruding articles of Examples 1A and 2A can be expected to efficiently and continuously manufacture fine hollow protruding articles with excellent precision in shape.

(1) Preparation of Projecting Mold Part 11 of Manufacturing Device:

A projecting mold part made of SUS304, which is a type of stainless steel, was prepared as the projecting mold part 11. The projecting mold part 11 had one circular-conic projecting mold 110. The height H2 (height of the tapered portion) of the projecting mold 110 was 2.5 mm, the tip end diameter D1 was 15 μm, the base diameter D2 was 0.5 mm, and the tip end angle was 11 degrees.

(2) Preparation of Base Sheet 2A:

A continuous sheet made of polylactic acid (PLA; Tg: 55.8° C.) and having a thickness of 0.3 mm was prepared as the base sheet 2A.

Example 1B

A microneedle array 1M, as a fine hollow protruding article 1, was manufactured according to the procedure of FIG. 16. More specifically, the heating means of the projecting mold part 11 was an ultrasonic vibration device. The manufacturing conditions were as shown in Table 2. That is, the frequency of the ultrasonic vibration was 20 kHz and the amplitude of the ultrasonic vibration was 40 μm in both the protrusion precursor forming section 10A and the protrusion elongating section 10B. In the protrusion precursor forming section 10A, the insertion height was 0.1 mm and the insertion speed was 30 mm/s. On the other hand, in the protrusion elongating section 10B, the insertion height was 1.0 mm and the insertion speed was 5 mm/s. That is, the insertion speed in the protrusion elongating section 10B was made slower than the insertion speed in the protrusion precursor forming section 10A. Further, the softening time was 0.5 seconds and the cooling time was 1 second. A fine hollow protruding article of Example 1B was manufactured according to the aforementioned manufacturing conditions. Note that the temperature of the base sheet upon insertion was 85° C., and the base sheet was softened.

Comparative Example 1B

A fine hollow protruding article of Comparative Example 1B was manufactured according to the same manufacturing conditions as in Example 1B, except that the insertion speed was 5 mm/s in the protrusion precursor forming section 10A.

{Performance Evaluation}

For each of the fine hollow protruding articles of Example 1B and Comparative Example 1B, whether or not a through hole was formed was observed with a microscope. If the fine hollow protruding article had a through hole, the tip end diameter L of the fine hollow protruding article was measured according to the method described above. The results are shown in Table 2 below.

Figure 34:
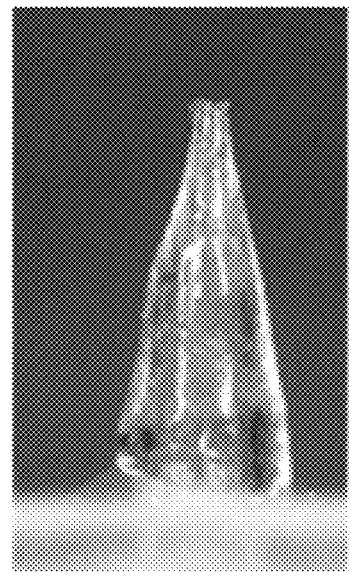
FIG. 34 is a photograph of the manufactured fine hollow protruding articles of Example 1B.
Figure 35:
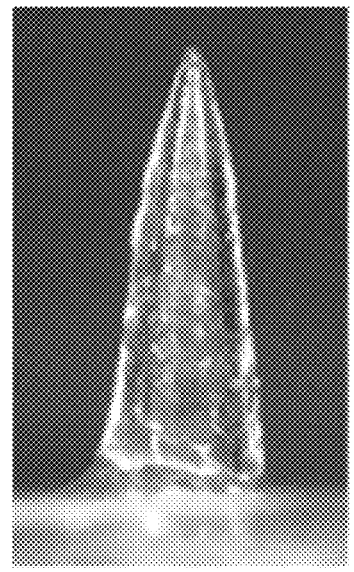
FIG. 35 is a photograph of the manufactured fine hollow protruding articles of Comparative Example 1B.

FIG. 34 is a photograph of the manufactured fine hollow protruding articles of Example 1B; and FIG. 35 is a photograph of the manufactured fine hollow protruding articles of Comparative Example 1B.

TABLE 2

| | Embodiment | Unit | Example 1B | Comp. Example 1B |
|---|---|---|---|---|
| Manufacturing conditions for protrusion precursor forming section | Insertion speed | mm/s | 30 | 5 |
| | Insertion height | mm | 0.1 | 0.1 |
| Manufacturing conditions for protrusion forming section | Insertion speed | mm/s | 5 | 5 |
| | Insertion height | mm | 1.0 | 1.0 |
| Manufacturing conditions (common) | Frequency of ultrasonic vibration | kHz | 20 | 20 |
| | Amplitude of ultrasonic vibration | μm | 40 | 40 |
| | Softening time | s | 0.5 | 0.5 |
| | Cooling time | s | 1 | 1 |
| Fine hollow protruding article | Presence/absence of through hole | — | Present | Absent |
| | Tip end diameter | μm | 41 | — |

As is clear from the results of Table 2, the fine hollow protruding article of Example 1B has a through hole formed in the protrusion, and the precision in the height of the protrusion and the size of the through hole was excellent, compared to the fine hollow protruding article of Comparative Example 1B. The reason why such a result was obtained is thought to be that, in the protrusion precursor forming section 10A, the condition of the insertion height in both Example 1B and Comparative Example 1B was set to 0.1 mm, whereas the condition of the insertion speed in Example 1B (30 mm/s) was set faster than the condition of the insertion speed in Comparative Example 1B (5 mm/s), and thus, a protrusion precursor 3b having a through hole 3h was formed in Example 1B whereas no through hole 3h was formed in Comparative Example 1B. Stated differently, it is considered that, in the process for manufacturing the fine hollow protruding article of Comparative Example 1B, the protruding article did not undergo a protrusion precursor forming step, and thus, no through hole was formed in the protrusion. Thus, the manufacturing method for manufacturing the fine hollow protruding article of Example 1B can be expected to efficiently and continuously manufacture fine hollow protruding articles with excellent precision in the height of the protrusion and the size of the through hole.

(1) Preparation of Projecting Mold Part 11 of Manufacturing Device:

A projecting mold part made of SUS304, which is a type of stainless steel, was prepared as the projecting mold part 11. The projecting mold part 11 had one circular-conic projecting mold 110. The height H2 (height of the tapered portion) of the projecting mold 110 was 2.5 mm, the tip end diameter D1 was 15 µm, the base diameter D2 was 0.5 mm, and the tip end angle was 11 degrees.

(2) Preparation of Base Sheet 2A:

A continuous sheet made of polylactic acid (PLA; Tg: 55.8° C.) and having a thickness of 0.3 mm was prepared as the base sheet 2A.

Example 1C

A microneedle array 1M, as a fine hollow protruding article 1, was manufactured according to the procedure of FIG. 25. More specifically, the heating means of the projecting mold part 11 was an ultrasonic vibration device. A receiving member made of a polyacetal synthetic resin was prepared as the receiving member 13. The receiving member 13 had one circular-conic depression 131. The shape of the opening peripheral edge 131a of the depression 131 matched the shape of the outer periphery 11c at a position where the peripheral wall 11W of the peripheral wall 11W of the projecting mold part 11 came into contact with the receiving member 13. Stated differently, the diameter of the opening peripheral edge 131a was the same as the diameter of the projecting mold 110 at the aforementioned contact position. Note that the position of the projecting mold 110 at the aforementioned contact position was in a section between the tip-end portion and the base portion. The manufacturing conditions were as shown in Table 3. That is, the frequency of the ultrasonic vibration was 20 kHz and the amplitude of the ultrasonic vibration was 40 µm. The insertion height was 0.5 mm and the insertion speed was 10 mm/s. Further, the softening time was 0.5 seconds and the cooling time was 1 second. A fine hollow protruding article of Example 1C was manufactured according to the aforementioned manufacturing conditions. Note that the temperature of the base sheet upon insertion was 85° C., and the base sheet was softened.

Comparative Example 1C

A fine hollow protruding article of Comparative Example 1C was manufactured according to the same manufacturing conditions as in Example 1C, except that a receiving member having a penetrating depression was used. Note that, the diameter of the opening peripheral edge of the depression 131 was larger than the base diameter D2 of the projecting mold 110.

{Performance Evaluation}

For each of the fine hollow protruding articles of Example 1C and Comparative Example 1C, whether or not a through hole was formed was observed with a microscope. If the fine hollow protruding article had a through hole, the tip end diameter L of the fine hollow protruding article was measured according to the method described above. The results are shown in Table 3 below.

Figure 36:
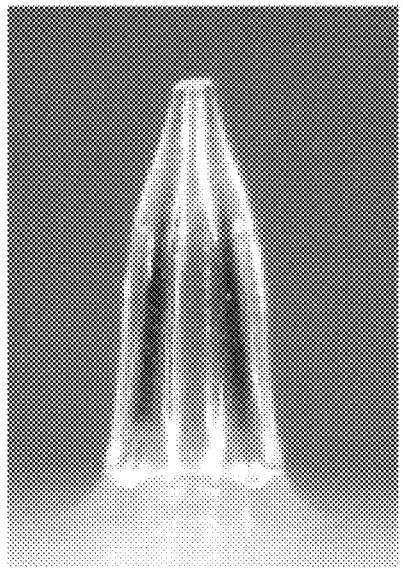
FIG. 36 is a photograph of the manufactured fine hollow protruding articles of Example 1C.
Figure 37:
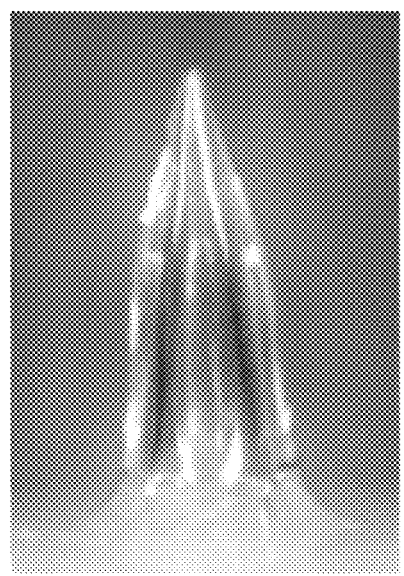
FIG. 37 is a photograph of the manufactured fine hollow protruding articles of Comparative Example 1C.

FIG. 36 is a photograph of the manufactured fine hollow protruding articles of Example 1C; and FIG. 37 is a photograph of the manufactured fine hollow protruding articles of Comparative Example 1C.

TABLE 3

| Embodiment | | Unit | Example 1C | Comp. Example 1C |
|---|---|---|---|---|
| Manufacturing conditions | Relationship between diameter (1) at opening peripheral edge and diameter (2) at position contacting projecting mold part | — | (1) = (2) | (1) > (2) |
| Manufacturing conditions (common) | Frequency of ultrasonic vibration | kHz | 20 | 20 |
| | Amplitude of ultrasonic vibration | µm | 40 | 40 |
| | Insertion height | mm | 0.5 | 0.5 |
| | Insertion speed | mm/s | 10 | 10 |
| | Softening time | s | 0.5 | 0.5 |
| | Cooling time | s | 1 | 1 |
| Fine hollow protruding article | Presence/absence of through hole | — | Present | Absent |
| | Tip end diameter | µm | 47 | — |

As is clear from the results of Table 3, the fine hollow protruding article of Example 1C has a through hole formed therein, and the precision in the height of the protrusion and the size of the through hole was excellent, compared to the fine hollow protruding article of Comparative Example 1C. Thus, the manufacturing method for manufacturing the fine hollow protruding article of Example 1C can be expected to efficiently and continuously manufacture fine hollow protruding articles with excellent precision in the height of the protrusion and the size of the through hole.

INDUSTRIAL APPLICABILITY

According to the invention (first invention), fine hollow protruding articles can be manufactured continuously and efficiently while suppressing an increase in cost.

According to the invention (second and third inventions), high-quality through-hole-including fine hollow protruding articles having high precision in the height of the fine hollow protruding article and the size of the through hole can be mass-produced stably at low cost.

The invention claimed is:

1. A method for manufacturing a fine hollow protruding article having a hollow interior, the method comprising:
    a protrusion forming step of
        bringing a projecting mold part that includes a heating means into contact from one-surface side of a base sheet including a thermoplastic resin, and,
        while softening, with heat, a contact section in the base sheet where the projecting mold part contacts the base sheet, inserting the projecting mold part into the base sheet, to form a protrusion that protrudes from other-surface side of the base sheet;
    a cooling step of cooling the protrusion in a state where the projecting mold part is inserted in an interior of the protrusion; and
    a release step of withdrawing the projecting mold part from the interior of the protrusion after the cooling step, to form the fine hollow protruding article.

2. The method for manufacturing a fine hollow protruding article according to claim 1, wherein:
    the other-surface side corresponding to the contact section of the base sheet in contact with the projecting mold part has no depression into which the projecting mold part is fitted.

3. The method for manufacturing a fine hollow protruding article according to claim 1, wherein:

the protrusion forming step is performed by using a support that supports a region, of the base sheet, other than a region where the protrusion is formed when the projecting mold part is inserted into the base sheet;

the support is arranged on the other-surface side of the base sheet; and the protrusion is formed by bringing the projecting mold part into contact from the one-surface side in a section, of the base sheet, that is not supported by the support.

4. The method for manufacturing a fine hollow protruding article according to claim 3, wherein an opening plate having an opening into which a projecting mold of the projecting mold part can be inserted is used as the support.

5. The method for manufacturing a fine hollow protruding article according to claim 4, wherein the opening plate has a plurality of the openings.

6. The method for manufacturing a fine hollow protruding article according to claim 4, wherein one projecting mold is inserted into the respective opening of the opening plate.

7. The method for manufacturing a fine hollow protruding article according to claim 1, wherein the shape of the fine hollow protruding article is controlled by controlling at least one condition selected from a condition of the heating means of the projecting mold part in the protrusion forming step, an insertion height of the projecting mold part into the base sheet in the protrusion forming step, a softening time of the contact section of the base sheet in the protrusion forming step, an insertion speed of the projecting mold part into the base sheet in the protrusion forming step, the shape of the projecting mold part, and a cooling condition in the cooling step.

8. The method for manufacturing a fine hollow protruding article according to claim 1, wherein:

a continuous base sheet is used as the base sheet; and the fine hollow protruding articles are formed continuously on the other surface side of the continuous base sheet.

9. The method for manufacturing a fine hollow protruding article according to claim 1, wherein the heating temperature of the base sheet due to heating with the projecting mold part is equal to or higher than the glass transition temperature of the base sheet to below the melting temperature thereof.

10. The method for manufacturing a fine hollow protruding article according to claim 1, wherein the heating temperature of the base sheet due to heating with the projecting mold part is equal to or higher than the softening point of the base sheet to below the melting temperature thereof.

11. The method for manufacturing a fine hollow protruding article according to claim 1, wherein, in the protrusion forming step, no other heating means is provided except for the heating means of the projecting mold part.

12. The method for manufacturing a fine hollow protruding article according to claim 1, wherein:

the heating means of the projecting mold part is an ultrasonic vibration device; and the contact section is softened by causing ultrasonic vibration of the projecting mold part by the ultrasonic vibration device and generating heat in the contact section by friction.

13. The method for manufacturing a fine hollow protruding article according to claim 1, wherein:

the heating means of the projecting mold part is a heater device; and the contact section is softened by heating the projecting mold part by the heater device.

14. The method for manufacturing a fine hollow protruding article according to claim 1, wherein, in the protrusion forming step, a fine hollow protruding article including a plurality of protrusions arranged in an array is formed by using a plurality of the projecting mold parts.

15. The method for manufacturing a fine hollow protruding article according to claim 1, wherein the protrusion forming step comprises:

a protrusion precursor forming step of bringing the projecting mold part that includes the heating means into contact from the one-surface side of the thermoplastic-resin-including base sheet, and, while softening, with heat, the contact section in the base sheet, inserting the projecting mold part into the base sheet, to form a hollow protrusion precursor that protrudes from the other-surface side of the base sheet and that has a through hole that penetrates the tip end on the other-surface side of the base sheet; and a protrusion elongating step of further inserting the projecting mold part into the base sheet in a state where the projecting mold part is inserted in the interior of the protrusion precursor while softening, with heat, the contact section in the base sheet, to form a protrusion that further protrudes from the other surface of the base sheet.

16. The method for manufacturing a fine hollow protruding article according to claim 15, wherein the heat quantity applied from the projecting mold part to the base sheet in the protrusion elongating step is greater than the heat quantity applied from the projecting mold part to the base sheet in the protrusion precursor forming step.

17. The method for manufacturing a fine hollow protruding article according to claim 15, wherein the heat quantity per unit insertion height applied from the projecting mold part to the base sheet in the protrusion precursor forming step and the heat quantity per unit insertion height applied from the projecting mold part to the base sheet in the protrusion elongating step continuously change from the protrusion precursor forming step to the protrusion elongating step.

18. The method for manufacturing a fine hollow protruding article according to claim 15, wherein:

the condition of the heating means of the projecting mold part in the protrusion precursor forming step is the same as the condition of the heating means of the projecting mold part in the protrusion elongating step; and the insertion speed for further inserting the projecting mold part into the base sheet in the protrusion elongating step is slower than the insertion speed for inserting the projecting mold part into the base sheet in the protrusion precursor forming step.

19. The method for manufacturing a fine hollow protruding article according to claim 15, wherein:

the insertion speed for inserting the projecting mold part into the base sheet in the protrusion precursor forming step is the same as the insertion speed for further inserting the projecting mold part into the base sheet in the protrusion elongating step; and the heat quantity applied to the base sheet under the condition of the heating means of the projecting mold part in the protrusion elongating step is greater than the heat quantity applied to the base sheet under the condition of the heating means of the projecting mold part in the protrusion precursor forming step.

20. The method for manufacturing a fine hollow protruding article according to claim 1, wherein:

the method is for manufacturing a fine hollow protruding article having a through hole, and comprises:

a protrusion forming step of bringing the projecting mold part that includes the heating means into contact from the one-surface side of the thermoplastic-resin-including base sheet, and, while softening, with heat, the contact section in the base sheet, inserting the projecting mold part into the base sheet toward the other-surface side of the base sheet, to form a protrusion that protrudes from the other-surface side of the base sheet, a cooling step of cooling the protrusion in a state where the projecting mold part is inserted in the interior of the protrusion; and a release step of withdrawing the projecting mold part from the interior of the protrusion after the cooling step, to form the fine hollow protruding article;

the protrusion forming step employs a receiving member arranged at a distance from the other surface of the base sheet; and in the protrusion forming step, a through hole is formed in the protrusion by the projecting mold part coming into contact with the receiving member.

21. The method for manufacturing a fine hollow protruding article according to claim 20, wherein:

the receiving member has a depression;

the shape of an opening peripheral edge of the depression matches a shape of an outer periphery of the peripheral wall of the projecting mold part at a position where the peripheral wall comes into contact with the receiving member; and in the protrusion forming step, the projecting mold part is inserted into the base sheet until the peripheral wall of the projecting mold part comes into contact with the opening peripheral edge of the depression of the receiving member and the projecting mold part penetrates the base sheet.

22. The method for manufacturing a fine hollow protruding article according to claim 20, wherein:

the receiving member's surface that comes into contact with the projecting mold part is a flat surface; and in the protrusion forming step, the projecting mold part is inserted into the base sheet until the tip end of the projecting mold part comes into contact with the flat surface of the receiving member and the projecting mold part penetrates the base sheet.

* * * * *